US012685743B2

(12) United States Patent
Miller et al.

(10) Patent No.: US 12,685,743 B2
(45) Date of Patent: Jul. 21, 2026

(54) METHODS AND COMPOSITIONS FOR TREATING AND DIAGNOSING PANCREATIC CANCERS

(71) Applicant: New York University, New York, NY (US)

(72) Inventors: George Miller, Englewood, NJ (US); Berk Aykut, Brooklyn, NY (US); Deepak Saxena, New York, NY (US); Smruti Pushalkar, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 17/038,813

(22) Filed: Sep. 30, 2020

(65) Prior Publication Data

US 2021/0260092 A1     Aug. 26, 2021

Related U.S. Application Data

(60) Provisional application No. 62/909,037, filed on Oct. 1, 2019.

(51) Int. Cl.
| | |
|---|---|
| *A61K 31/7048* | (2006.01) |
| *A61K 45/06* | (2006.01) |
| *A61P 31/10* | (2006.01) |
| *A61P 35/00* | (2006.01) |

(52) U.S. Cl.
CPC .......... *A61K 31/7048* (2013.01); *A61K 45/06* (2013.01); *A61P 31/10* (2018.01); *A61P 35/00* (2018.01)

(58) Field of Classification Search
CPC ..... A61K 31/7048; A61K 45/06; A61P 31/10; A61P 35/00
See application file for complete search history.

(56) References Cited

U.S. PATENT DOCUMENTS

| | | |
|---|---|---|
| 10,632,160 B2 | 4/2020 | Lu |
| 10,869,923 B2 | 12/2020 | Chen et al. |
| 11,096,971 B2 | 8/2021 | Possemiers |
| 11,213,552 B2 | 1/2022 | Kovarik |
| 2014/0378531 A1 | 12/2014 | Miller et al. |
| 2016/0120915 A1 | 5/2016 | Blaser et al. |
| 2016/0354416 A1 | 12/2016 | Gajewski et al. |
| 2019/0290707 A1 | 9/2019 | Chen et al. |
| 2020/0113951 A1 | 4/2020 | Miller et al. |
| 2021/0069327 A1 | 3/2021 | Lu |
| 2021/0213073 A1 | 7/2021 | Zeng |
| 2021/0260092 A1 | 8/2021 | Miller |
| 2021/0315947 A1 | 10/2021 | Lynch |
| 2021/0346438 A1 | 11/2021 | Zitvogel |
| 2021/0353694 A1 | 11/2021 | Possemiers |
| 2022/0016188 A1 | 1/2022 | Wargo |

FOREIGN PATENT DOCUMENTS

| | | | | |
|---|---|---|---|---|
| WO | WO-2006089406 A1 * | 8/2006 | .......... | C07D 303/32 |
| WO | 2015075688 A1 | 5/2015 | | |
| WO | 2016172657 | 10/2016 | | |
| WO | 2018145082 | 8/2018 | | |
| WO | 2020243705 A1 | 12/2020 | | |
| WO | 2020243731 | 12/2020 | | |

OTHER PUBLICATIONS

Luo et al. (Pancreas vol. 48 No. 6, pp. 817-822, Jul. 2019).*
Chiorean et al. (Drug Design, Development and Therapy, vol. 5 No. 9, pp. 3529-3545, 2016).*
Akshintala, V. et al., "The Gut Microbiome in Pancreatic Disease" Clinical Gastroenterology and Hepatology (2019) Abstract, vol. 17, No. 2, 2 pages total.
Chen, S-M. et al., "The Synergistic Tumor Growth-Inhibitory Effect of Probiotic Lactobacillus on Transgenic Mouse Model of Pancreatic Cancer Treated with Gemcitabine" Scientific Reports (2020) vol. 10, No. 20319, 12 pages total.
Gopalakrishnan, V. et al., "Intervention Strategies for Microbial Terapeutics in Cancer Immunotherapy" Immuno-Oncology Technology (2020) vol. 6, Issue C. pp. 9-17.
Highlander, S.K. et al., "Gastrointestinal Microbiome Changes in Stage IV Pancreatic Cancer Patients Treated with Pembrolizumab With or Without Paricalcitol on the Stand Up to Cancer (SU2C) Pancreas Catalyst Trial" American Association for Cancer Research Inc. (2019) Abstract, vol. 79, No. 24, 3 pages total.
Thomas, R. M. et al., "Microbiota in Pancreatic Health and Disease: The Next Frontier in Microbiome Research" Castroentrology & Hepatology (2020) vol. 17, pp. 53-64.
Zhou, W. et al., "The Fecal Microbiota of Patients with Pancreatic Ductal Adenocarcinoma and Autoimmune Pancreatitis Characterized by Metagenomic Sequencing" Journal of Translational Medicine (2021) vol. 19, No. 215, 12 pages total.
Afshar-Kharghan, V. The role of the complement system in cancer. J. Clin. Invest. 127, 780-789 (2017).
Brown, J.H., Whitham, T.G., Morgan Ernest, S.K. & Gehring, C.A. Complex Species Interactions and the Dynamics of Ecological Systems: Long-Term Experiments. Science 293, 643-650 (2001).
Caporaso, J. G. et al. QIIME allows analysis of high-throughput community sequencing data. Nat. Methods 7, 335-336 (2010).
Caporaso, J.G., et al. Ultra-high-throughput microbial community analysis on the Illumina HiSeq and MiSeq platforms. The ISME Journal 6, 1621-1624 (2012).

(Continued)

*Primary Examiner* — Robert A Zeman
(74) *Attorney, Agent, or Firm* — Troutman Pepper Locke LLP

(57) ABSTRACT

The application relates to methods based on modulating pancreatic and/or gastrointestinal microbiota and related antifungal compositions. Specifically, the application relates to the use of microbiome for prevention, treatment and diagnosis of pancreatic cancers or tumors, such as pancreatic ductal adenocarcinoma.

7 Claims, 34 Drawing Sheets

(34 of 34 Drawing Sheet(s) Filed in Color)

Specification includes a Sequence Listing.

(56) References Cited

OTHER PUBLICATIONS

Cho, M. S. et al. Autocrine effects of tumor-derived complement. Cell Reports 6, 1085-1095 (2014).

Communication (International Preliminary Report on Patentability) issued by the International Searching Authority in International Application No. PCT/US2018/017052 dated Aug. 6, 2019, 13 pages total.

Communication (International Search Report) issued by the International Searching Authority in International Application No. PCT/US2018/017052 dated May 8, 2018, 4 pages total.

Communication (Written Opinion) issued by the International Searching Authority in International Application No. PCT/US2018/017052 dated May 8, 2018, 12 pages total.

Edgar, R.C. Search and clustering orders of magnitude faster than BLAST. Bioinformatics 26, 2460-2461 (2010).

Farrell, J.J., et al. Variations of oral microbiota are associated with pancreatic diseases including pancreatic cancer. Gut 61, 582-588 (2012).

Haas, B.J., et al. Chimeric 16S rRNA sequence formation and detection in Sanger and 454-pyrosequenced PCR amplicons. Genome Research 21, 494-504 (2011).

Hamada, S. et al., "Differences in Gut Microbiota Profiles between Autoimmune Pancreatitis and Chronic Pancreatitis" Tohoku Journal of Experimental Medicine (2018) vol. 244, No. 2, pp. 113-117.

Herlemann, D.P.R., et al. Transitions in bacterial communities along the 2000km salinity gradient of the Baltic Sea. ISME J 5, 1571-1579 (2011).

Hingorani, S. R. et al. Preinvasive and invasive ductal pancreatic cancer and its early detection in the mouse. Cancer Cell 4, 437-450 (2003).

Hingorani, S. R. et al. Trp53R172H and KrasG12D cooperate to promote chromosomal instability and widely metastatic pancreatic ductal adenocarcinoma in mice. Cancer Cell 7, 469-483 (2005).

Hruban. R. H. et al. Pancreatic intraepithelial neoplasia: a new nomenclature and classification system for pancreatic duct lesions. Am. J. Surg. Pathol. 25, 579-586 (2001).

Ino, Y., et al. Immune cell infiltration as an indicator of the immune microenvironment of pancreatic cancer. British journal of cancer 108, 914-923 (2013).

Ishikawa, T. et al. Identification of distinct ligands for the C-type lectin receptors mincle and dectin-2 in the pathogenic fungus Malassezia. Cell Host Microbe 13, 477-488 (2013).

Kamada, N., Seo, S.-U., Chen, G.Y. & Nunez, G. Role of the gut microbiota in immunity and inflammatory disease. Nat Rev Immunol 13, 321-335 (2013).

Klindworth, A., et al. Evaluation of general 16S ribosomal RNA gene PCR primers for classical and next-generation sequencing-based diversity studies. Nucleic Acids Research 41, e1-e1 (2013).

Leal-Lopes, C. et al., "Roles of Commensal Microbiota in Pancreas Homeostasis and Pancreatic Pathologies" Hindawi Publishing Corporation (2015) vol. 2015m Article ID 284680, 20 pages total.

Masella, A.P., Bartram, A.K., Truszkowski, J.M., Brown, D.G. & Neufeld, J.D. PANDAseq; paired-end assembler for Illumina sequences. BMC Bioinformatics 13, 31-31 (2012).

Mi, H., Muruganujan, A., Casagrande, J.T. & Thomas, P.D. Large-scale gene function analysis with the PANTHER classification system. Nature protocols 8, 1551-1566 (2013).

Michaud, D.S., Joshipura, K., Giovannucci, E. & Fuchs, C.S. A Prospective Study of Periodontal Disease and Pancreatic Cancer in US Male Health Professionals, Journal of the National Cancer Institute 99, 171-175 (2007).

Mitsuhashi, K., et al. Association of Fusobacterium species in pancreatic cancer tissues with molecular features and prognosis. Oncotarget; vol. 6, No. 9 (2015).

Navas-Molina, J.A., et al. Advancing our understanding of the human microbiome using QIIME. Methods in Enzymology 531, 371-444 (2013).

Plottel, C.S. & Blaser, M.J. Microbiome and Malignancy. Cell host & microbe 10, 324-335 (2011).

Price, M.N., Dehal, P.S. & Arkin, A.P. FastTree: Computing Large Minimum Evolution Trees with Profiles instead of a Distance Matrix. Molecular Biology and Evolution 26, 1641-1650 (2009).

Pushalkar, S. et al., "The Pancreatic Cancer Microbiome Promotes Oncogenesis by Induction of Innate and Adaptive Immune Suppression" Cancer Discovery (2018) vol. 8. No. 4, pp. 403-416.

Pushalkar, S., et al. Comparison of oral microbiota in tumor and non-tumor tissues of patients with oral squamous cell carcinoma. BMC Microbiology 12, 144-144 (2012).

Pushalkar, S., et al. Oral microbiota and host innate immune response in bisphosphonate-related osteonecrosis of the jaw. In J Oral Sci 6, 219-226 (2014).

Reikvam, D. H. et al. Depletion of murine intestinal microbiota: effects on gut mucosa and epithelial gene expression. PLoS One 6, e17996 (2011).

Rutkowski, M.R., et al. Microbially driven TLR5-dependent signaling governs distal malignant progression through tumor-promoting inflammation. Cancer cell 27, 27-40 (2015).

Sam, Q. H., Chang, M. W. & Chai, L. Y. The fungal mycobiome and its interaction with gut bacteria in the host. Int. J. Mol. Sci. 18, 330 (2017).

Schwabe, R.F. & Jobin, C. The microbiome and cancer. Nature reviews. Cancer 13, 800-812 (2013).

Segata, N., et al. Metagenomic biomarker discovery and explanation. Genome Biology 12, R60-R60 (2011).

Seifert, L. et al. The necrosome promotes pancreatic oncogenesis via CXCL1 and Mincle-induced immune suppression. Nature 532, 245-249 (2016).

Seifert. L., et al. Radiation Therapy Induces Macrophages to Suppress Immune Responses Against Pancreatic Tumors in Mice. Gastroenterology (2016).

Skalski, J. H. et al. Expansion of commensal fungus Wallemia mellicola in the gastrointestinal mycobiota enhances the severity of allergic airway disease in mice. PLoS Pathog. 14, e1007260 (2018).

Van Asbeck, et al., "Mannose binding lectin plays a crucial role in innate immunity against yeast by enhanced complement activation and enhanced uptake of polymorphonuclear cells" BMC Microbiol. 8, 229 (2008).

Walters, W. et al. Improved bacterial 16S rRNA gene (V4 and V4-5) and fungal internal transcribed spacer marker gene primers for microbial community surveys. mSystems 1, e00009-15 (2015).

Zambirinis, C.P., et al. TLR9 ligation in pancreatic stellate cells promotes tumorigenesis. The Journal of Experimental Medicine 212, 2077-2094 (2015).

Office Action issued Aug. 5, 2021 in connection with U.S. Appl. No. 16/484,080.

Office Action issued Mar. 17, 2022 in connection with U.S. Appl. No. 16/484,080.

Shah et al., "Trends in Food Science & Technology," 102 (2020) 178-192. available online Jun. 23, 2020 (Year: 2020).

Routy et al., European Urology 74 (2018) 521-526 (Year: 2018).

Routy et al., Nature Reviews, Clinical Oncology. Jun. 2018, 15:385-396. published online: Apr. 10, 2018 (Year: 2018).

Messaoudene et al., Cancer Research (Aug. 2020) vol. 80, No. 16 Suppl. Abstract No. 5730 (Year: 2020).

Office Action issued Nov. 1, 2022 in connection with U.S. Appl. No. 16/484,080.

Janda et al., "16S rRNA Gene Sequencing for Bacterial Identification in the Diagnostic Laboratory: Pluses, Perils, and Pitfalls", Sep. 2007, Journal of Clinical Microbiology, vol. 45, No. 9, p. 2761-2764, (Year: 2007).

Jiang et al., "Targeting focal adhesion kinase renders pancreatic cancers responsive to checkpoint immunotherapy", Aug. 2016, Nature Medicine, vol. 22, No. 8, p. 851-860. (Year: 2016).

Dingemanse et al., "Akkermansia muciniphila and Helicobacter typhlonius modulate intestinal tumor development in mice", 2015, Carcinogenesis, vol. 36, No. 11, p. 1388-1396 (Year: 2015).

Aykut et al., "The Fungal Mycobiome Promotes Pancreatic Oncogenesis via Activation of MBL" Nature 2019 vol. 574:264-267.

* cited by examiner

Sequence match of *Malassezia globosa* from human samples and ATTC strain used in repopulation experiments

SH184033.07FU_GU291271_refs
Malassezia globosa strain 149.1 18S ribosomal RNA gene, partial sequence; internal transcribed spacer 1, 5.8S ribosomal RNA gene, and internal transcribed spacer 2, complete sequence; and 28S ribosomal RNA gene, partial sequence
Sequence ID: KM454161.1Length: 813Number of Matches: 1
Range 1: 9 to 283GenBankGraphicsNext MatchPrevious Match

| Score | Expect | Identities | Gaps | Strand |
|---|---|---|---|---|
| 508 bits(275) | 2e-141 | 275/275(100%) | 0/275(0%) | Plus/Plus |

```
Query   1    AAGTCGTAACAAGGTTTCTGTAGGTGAACCTGCAGAAGGATCATTAGTGAAGATTCAAGG   60
             ||||||||||||||||||||||||||||||||||||||||||||||||||||||||||||
Sbjct   9    AAGTCGTAACAAGGTTTCTGTAGGTGAACCTGCAGAAGGATCATTAGTGAAGATTCAAGG   68

Query   61   GCCAGCCATACAGACGTACAATAAGTGTGTCTCTGGCGGCTCGTATCCACTATACATCCA   120
             ||||||||||||||||||||||||||||||||||||||||||||||||||||||||||||
Sbjct   69   GCCAGCCATACAGACGTACAATAAGTGTGTCTCTGGCGGCTCGTATCCACTATACATCCA   128

Query   121  TAAACCCGTGTGCACTGTTAAGGAGTAAGAAAGAAGGGGAGGGAGAGAGTGCATGTGCTT   180
             ||||||||||||||||||||||||||||||||||||||||||||||||||||||||||||
Sbjct   129  TAAACCCGTGTGCACTGTTAAGGAGTAAGAAAGAAGGGGAGGGAGAGAGTGCATGTGCTT   188

Query   181  TGCATATAActctctctctttctcttcctttctctctctGGTTAATTACACAAACTCGTA   240
             ||||||||||||||||||||||||||||||||||||||||||||||||||||||||||||
Sbjct   189  TGCATATAACTCTCTCTCTTTCTCTTCCTTTCTCTCTCTGGTTAATTACACAAACTCGTA   248

Query   241  TGGATTTGTATGAACGTGAGATATATCGTTGGACC   275
             |||||||||||||||||||||||||||||||||||
Sbjct   249  TGGATTTGTATGAACGTGAGATATATCGTTGGACC   283
```

Figure 9B

SH184035.07FU_KM269167_reps
Malassezia globosa strain 160.5 18S ribosomal RNA gene, partial sequence; internal
transcribed spacer 1, 5.8S ribosomal RNA gene, and internal transcribed spacer 2,
complete sequence; and 28S ribosomal RNA gene, partial sequence
Sequence ID: KM370119.1Length: 1490Number of Matches: 1
Range 1: 121 to 398GenBankGraphicsNext MatchPrevious Match

| Score | Expect | Identities | Gaps | Strand |
|---|---|---|---|---|
| 514 bits(278) | 3e-143 | 278/278(100%) | 0/278(0%) | Plus/Plus |

```
Query    1    AAGTCGTAACAAGGTTTCTGTAGGTGAACCTGCAGAAGGATCATTAGTGAAGATTCAAGG   60
              ||||||||||||||||||||||||||||||||||||||||||||||||||||||||||||
Sbjct   121    AAGTCGTAACAAGGTTTCTGTAGGTGAACCTGCAGAAGGATCATTAGTGAAGATTCAAGG   180

Query   61    GCCAGCCATACAGACGTACAACAAGTGTGTCTCTGGCGGCTCGCATCCCACTATACATCC   120
              ||||||||||||||||||||||||||||||||||||||||||||||||||||||||||||
Sbjct   181    GCCAGCCATACAGACGTACAACAAGTGTGTCTCTGGCGGCTCGCATCCCACTATACATCC   240

Query   121   ATAAACCCGTGTGCACAGTTGTAGGAGTGAGAAAGAAGGGAGAGAGTGCGTGTGTTTTGC   180
              ||||||||||||||||||||||||||||||||||||||||||||||||||||||||||||
Sbjct   241   ATAAACCCGTGTGCACAGTTGTAGGAGTGAGAAAGAAGGGAGAGAGTGCGTGTGTTTTGC   300

Query   181   ATAACTCTCTCTCGCTTTCTCTCTCCGATTCATTACAAACTCGTATGGATTTGTATGAAC   240
              ||||||||||||||||||||||||||||||||||||||||||||||||||||||||||||
Sbjct   301   ATAACTCTCTCTCGCTTTCTCTCTCCGATTCATTACAAACTCGTATGGATTTGTATGAAC   360

Query   241   GTGAGATATATCGTTGGACCGTCACTGGCCAACAAATG    278
              ||||||||||||||||||||||||||||||||||||||
Sbjct   361   GTGAGATATATCGTTGGACCGTCACTGGCCAACAAATG    398
```

Figure 9C

Sequence match of *Malassezia globosa* from mice samples and ATTC strain used in repopulation experiments (represent sequences shown)

SH184033.07FU_GU291271_refs

Malassezia globosa strain 149.1 18S ribosomal RNA gene, partial sequence; internal transcribed spacer 1, 5.8S ribosomal RNA gene, and internal transcribed spacer 2, complete sequence; and 28S ribosomal RNA gene, partial sequence
Sequence ID: KM454161.1Length: 813Number of Matches: 1
Range 1: 9 to 286GenBankGraphicsNext MatchPrevious Match

| Score | Expect | Identities | Gaps | Strand |
|---|---|---|---|---|
| 514 bits(278) | 3e-143 | 278/278(100%) | 0/278(0%) | Plus/Plus |

```
Query  1    AAGTCGTAACAAGGTTTCTGTAGGTGAACCTGCAGAAGGATCATTAGTGAAGATTCAAGG  60
            ||||||||||||||||||||||||||||||||||||||||||||||||||||||||||||
Sbjct  9    AAGTCGTAACAAGGTTTCTGTAGGTGAACCTGCAGAAGGATCATTAGTGAAGATTCAAGG  68

Query  61   GCCAGCCATACAGACGTACAATAAGTGTGTCTCTGGCGGCTCGTATCCACTATACATCCA  120
            ||||||||||||||||||||||||||||||||||||||||||||||||||||||||||||
Sbjct  69   GCCAGCCATACAGACGTACAATAAGTGTGTCTCTGGCGGCTCGTATCCACTATACATCCA  128

Query  121  TAAACCCGTGTGCACTGTTAAGGAGTAAGAAAGAAGGGGAGGGAGAGAGTGCATGTGCTT  180
            ||||||||||||||||||||||||||||||||||||||||||||||||||||||||||||
Sbjct  129  TAAACCCGTGTGCACTGTTAAGGAGTAAGAAAGAAGGGGAGGGAGAGAGTGCATGTGCTT  188

Query  181  TGCATATAActctctctctttctcttcctttctctctctGGTTAATTACACAAACTCGTA  240
            ||||||||||||||||||||||||||||||||||||||||||||||||||||||||||||
Sbjct  189  TGCATATAACTCTCTCTCTTTCTCTTCCTTTCTCTCTCTGGTTAATTACACAAACTCGTA  248

Query  241  TGGATTTGTATGAACGTGAGATATATCGTTGGACCGTC  278
            ||||||||||||||||||||||||||||||||||||||
Sbjct  249  TGGATTTGTATGAACGTGAGATATATCGTTGGACCGTC  286
```

Figure 9D

SH184034.07FU_KP825445_reps
Malassezia globosa strain 146.1 18S ribosomal RNA gene, partial sequence; internal transcribed spacer 1, 5.8S ribosomal RNA gene, and internal transcribed spacer 2, complete sequence; and 28S ribosomal RNA gene, partial sequence
Sequence ID: KM269155.1Length: 1417Number of Matches: 1
Range 1: 151 to 429GenBankGraphicsNext MatchPrevious Match

| Score | Expect | Identities | Gaps | Strand |
|---|---|---|---|---|
| 516 bits(279) | 9e-144 | 279/279(100%) | 0/279(0%) | Plus/Plus |

```
Query    1    AAGTCGTAACAAGGTTTCTGTAGGTGAACCTGCAGAAGGATCATTAGTGAAGATTCAAGG    60
              ||||||||||||||||||||||||||||||||||||||||||||||||||||||||||||
Sbjct   151   AAGTCGTAACAAGGTTTCTGTAGGTGAACCTGCAGAAGGATCATTAGTGAAGATTCAAGG    210

Query   61    GCCAGCCATACAGACGTACAATAAGTGTGTCTCTGGCGGCTCGCATCCACTATACATCCA    120
              ||||||||||||||||||||||||||||||||||||||||||||||||||||||||||||
Sbjct   211   GCCAGCCATACAGACGTACAATAAGTGTGTCTCTGGCGGCTCGCATCCACTATACATCCA    270

Query   121   TAAACCCGTGTGCACTGTTCTAAGGAGTAAGAAAGAAGAAGAGAGAGTGCATGTGCTTTG    180
              ||||||||||||||||||||||||||||||||||||||||||||||||||||||||||||
Sbjct   271   TAAACCCGTGTGCACTGTTCTAAGGAGTAAGAAAGAAGAAGAGAGAGTGCATGTGCTTTG    330

Query   181   CATATAActctctcactctctttctctctcCGGTTAATTACAAACTCGTATGGATTTGTA    240
              ||||||||||||||||||||||||||||||||||||||||||||||||||||||||||||
Sbjct   331   CATATAACTCTCTCACTCTCTTTCTCTCTCCGGTTAATTACAAACTCGTATGGATTTGTA    390

Query   241   TGAACGTGAGATATATCGTTGGACCGTCACTGGCCAACA    279
              |||||||||||||||||||||||||||||||||||||||
Sbjct   391   TGAACGTGAGATATATCGTTGGACCGTCACTGGCCAACA    429
```

METHODS AND COMPOSITIONS FOR TREATING AND DIAGNOSING PANCREATIC CANCERS

CROSS-REFERENCE TO RELATED APPLICATIONS

This application claims priority to U.S. Provisional Applications Ser. No. 62/909,037, filed on Oct. 1, 2019, the contents of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 28, 2020, is named 243735_000217_SL.txt and is 3,497 bytes in size.

FIELD

The application relates to methods based on modulating mammalian pancreatic and gastrointestinal (GI) microbiota and related antifungal compositions. Specifically, the application relates to the use of antifungal compositions, for modulating the pancreatic and gastrointestinal (GI) microbiota, as well as for treatment, prevention and diagnosis of pancreatic ductal adenocarcinoma (PDA) at both early and advanced stages.

BACKGROUND

Pancreatic ductal adenocarcinoma (PDA) is the fifth leading cancer diagnosis in the USA and is highly lethal, with ~95% of patients dying within 5 years of diagnosis. PDA is the third most lethal cancer in the United States and accounts for 85% of all pancreatic malignancies. There are no effective means to prevent or delay cancer onset and few effective treatment options exist once transformation has occurred.

The average human body, consisting of about $10^{13}$ cells, has about ten times that number of microorganisms. The ~$10^{14}$ microbes that live in and on each of our bodies belong to all three domains of life on earth—bacteria, archaea and eukarya including fungi. The major sites for our indigenous microbiota are the intestinal tract, skin and mucosal surfaces such as nasal mucosa and vagina as well as the oropharynx. The gut microbiorne has emerged as an important regulator in the balance between health and disease, including oncogenesis[17,18]. Flowever, the role of microbiome in disease states in non-GI organs such as the pancreas has not been clearly understood or appreciated. In particular, the fungal microbiome or mycobiome in such organs has been poorly studied. Thus, there remains a need for methods for diagnosing, treating and preventing conditions such as PDA based on the gut microbiome.

SUMMARY OF THE INVENTION

As specified in the Background section above, there is a great need in the art for diagnosing, preventing and/or treating pancreatic ductal adenocarcinoma (PDA). The present application addresses these and other needs.

In one aspect, provided herein is a method for preventing or treating a pancreatic cancer or tumor in a subject in need thereof, said method comprising administering to the subject an effective amount of a compound or composition, wherein the compound or composition inhibits growth and/or activity of one or more strains of fungi from the genus *Malassezia* in the pancreatic and/or gastrointestinal microbiota of the subject. In certain embodiments, the compound or composition inhibits growth and/or activity of one or more strains of fungi from the species *Malassezia globosa* in the pancreatic and/or gastrointestinal microbiota of the subject. In certain embodiments, the pancreatic cancer is pancreatic ductal adenocarcinoma (PDA).

In certain embodiments, the subject has a functional mannose-binding lectin (MBL)-C3 convertase complement axis.

In certain embodiments, compound or composition comprises an antifungal compound or a natural product that inhibits fungal growth.

In certain embodiments, the antifungal compound is selected from an echocandin compound, a triazole compound, a polyene compound, and any combinations thereof. In certain embodiments, the antifungal compound is amphotericin B or fluconazole.

In certain embodiments, said compound or composition is administered directly to the pancreas and/or gastrointestinal tract. In certain embodiments, said compound or composition is administered by a route selected from oral, rectal, sublingual, topical, intravenous, and via naso/oro-gastric gavage.

In certain embodiments of the methods described above, the method further comprises inhibiting the function of mannose-binding lectin (MBL)-C3 convertase complement axis systemically or in the pancreas of the subject. In certain embodiments, the function of mannose-binding lectin (MBL)-C3 convertase complement axis is inhibited using a small molecule inhibitor or an antibody.

In certain embodiments of the methods described above, the method further comprises administering a compound or composition that stimulates growth and/or activity of one or more strains of fungi from the genera *Saccharomyces* and *Candida* in the pancreatic and/or gastrointestinal microbiota of the subject. In certain embodiments, the method comprises administering to the subject a composition comprising one or more strains of fungi from the genera *Saccharomyces* and *Candida*.

In certain embodiments of the methods described above, the method further comprises administering to the subject one or more of the following (i) a probiotic and/or a prebiotic composition that stimulates growth and/or activity of one or more strains of bacteria from one or more genera selected from *Bifidobacterium, Faecalibacterium, Propionibacterium, Pseudoxanthomonas, Streptomyces*, Saccharopolyspora in the pancreatic microbiota of the subject;

(ii) a probiotic and/or a prebiotic composition that stimulates growth and/or activity of one or more strains of bacteria from one or more genera selected from *Akkermansia, Bacteroides, Bifidobacterium, Blautia, Brachyspira, Candidatus arthromitus, Dorea, Eubacterium, Faecalibacterium, Gallicola, Lactobacillus, Megamonas*, Mollicutes RF39, *Mycoplasma, Parabacteroides, Prevotella, Ruminococcus*, Tenericutes ML615J-28, and *Ureaplasma* in the gastrointestinal (GI) microbiota of the subject;

(iii) a probiotic and/or a prebiotic composition that stimulates growth and/or activity of one or more strains of bacteria from one or more species selected from *Bifidobacterium pseudolongum, Faecalibacterium prausnitzii, Bacillus clausii*, and *Propionibacterium acnes* in the pancreatic microbiota of the subject;

3

(iv) a probiotic and/or a prebiotic composition that stimulates growth and/or activity of one or more strains of bacteria from one or more species selected from *Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus*, and TM7 in the gastrointestinal (GI) microbiota of the subject;

(v) a probiotic composition comprising one or more strains of bacteria from one or more genera selected from *Bifidobacterium, Faecalibacterium, Propionibacterium, Pseudoxanthomonas, Streptomyces, Saccharopolyspora, Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus,* TenericutesML615J-28, and *Ureaplasma;*

(vi) a probiotic composition comprising one or more strains of bacteria from one or more species selected from *Bifidobacterium pseudolongum, Faecalibacterium prausnitzii*, and *Propionibacterium acnes, Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus, Bacillus clausii*, and TM7;

(vii) a compound or composition which inhibits growth and/or activity of one or more strains of bacteria from one or more genera selected from *Bacteroides, Bifidobacterium, Chryseobacterium, Delftia, Elizabethkingia, Lactobacillus, Mucispirillum, Pseudomonas, Streptococcus, Fusobacterium*, and *Viellonella* in the pancreatic microbiota of the subject;

(viii) a compound or composition which inhibits growth and/or activity of one or more strains of bacteria from one or more genera selected from *Akkermansia, Bacteroides, Bifidobacterium, Desulfovibrio, Elizabethkingia, Escherichia, Lactobacillus, Mucispirillum, Oxalobacter, Parabacteroides, Peptostreptococcus, Prevotella, Pyramidobacter, Rothia, Streptococcus*, and *Viellonella* in the gastrointestinal (GI) microbiota of the subject;

(ix) a compound or composition which inhibits growth and/or activity of one or more strains of bacteria from one or more species selected from *Bacteroides acidifaciens, Bifidobacterium pseudolongum, Elizabethkingia meningoseptica, Lactobacillus reuteri, Mucispirillum schaedleri, Streptococcus anginosus, Porphyromonas gingivalis, Streptococcus mitis, Neisseria elongata, Helicobacter pylori*, and *Veillonella dispar* in the pancreatic microbiota of the subject; or (x) a compound or composition which inhibits growth and/or activity of one or more strains of bacteria from one or more species selected from *Akkermansia muciniphila, Bacteroides acidifaciens, Bifidobacterium animalis, Bifidobacterium pseudolongum, Desulfovibrio* D168, *Elizabethkingia meningoseptica, Escherichia coli, Lactobacillus reuteri, Mucispirillium schaedleri, Oxalobacter formigenes, Parabacteroides distasoni, Peptostreptococcus anaerobius, Prevotella melaninogenica, Prevotella stercorea, Pyramidobacter piscol-*

4

*ens, Rothia mucilaginosa, Streptococcus anginosus*, and *Veillonella dispar* in the gastrointestinal (GI) microbiota of the subject.

In certain embodiments of the methods described above, the method further comprises administering an additional cancer therapy. In certain embodiments, the additional cancer therapy is selected from surgery, radiotherapy, chemotherapy, immunotherapy, and any combinations thereof.

In certain embodiments, the chemotherapy is selected from FOLFIRINOX (folinic acid, 5-fluorouracil, irinotecan, oxaliplatin), gemcitabine, ABRAXANE (protein-bound paclitaxel), capecitabine, 5-fluorouracil, and any combinations thereof.

In certain embodiments, the immunotherapy comprises administering an immune checkpoint inhibitor. In certain embodiments, the immune checkpoint inhibitor is a programmed cell death protein 1 (PD-1) inhibitor, a programmed death-ligand 1 (PD-L1) inhibitor or a cytotoxic T-lymphocyte-associated antigen 4 (CTLA-4) inhibitor. In certain embodiments, the PD-1 inhibitor is an antibody. In certain embodiments, the antibody is pembrolizumab or nivolumab.

In various embodiments of the methods described above, the subject is human.

In another aspect, provided herein is a method for enhancing efficacy of a treatment for a pancreatic cancer or tumor in a subject in need thereof, said method comprising (i) administering said treatment to the subject and further (ii) administering to the subject an effective amount of a first compound or composition, wherein said first compound or composition inhibits growth and/or activity of one or more strains of fungi from the genus *Malassezia* in the pancreatic and/or gastrointestinal microbiota of the subject. In certain embodiments, said first compound or composition inhibits growth and/or activity of one or more strains of fungi from the species *Malassezia globosa* in the pancreatic and/or gastrointestinal microbiota of the subject. In certain embodiments, the pancreatic cancer is pancreatic ductal adenocarcinoma (PDA).

In certain embodiments of the method for enhancing efficacy of a treatment, the subject has a functional mannose-binding lectin (MBL)-C3 convertase complement axis.

In certain embodiments of the method for enhancing efficacy of a treatment, said first compound or composition comprises an antifungal compound or a natural product that inhibits fungal growth. In certain embodiments, the antifungal compound is selected from an echocandin compound, a triazole compound, and a polyene compound, and any combinations thereof. In certain embodiments. In certain embodiments, the antifungal compound is amphotericin B or fluconazole.

In certain embodiments of the method for enhancing efficacy of a treatment, said first compound or composition is administered directly to the pancreas and/or gastrointestinal tract. In certain embodiments, said first compound or composition is administered by a route selected from oral, rectal, sublingual, topical, intravenous, and via naso/orogastric gavage.

In certain embodiments of the method for enhancing efficacy of a treatment, the method further comprises inhibiting the function of mannose-binding lectin (MBL)-C3 convertase complement axis systemically or in the pancreas of the subject. In certain embodiments, the function of mannose-binding lectin (MBL)-C3 convertase complement axis is inhibited using a small molecule inhibitor or an antibody.

In certain embodiments of the method for enhancing efficacy of a treatment, the method further comprises administering a second compound or composition that stimulates growth and/or activity of one or more strains of fungi from the genera *Saccharomyces* and *Candida* in the pancreatic and/or gastrointestinal microbiota of the subject. In certain embodiments, the method further comprises administering to the subject a composition comprising one or more strains of fungi from the genera *Saccharomyces* and *Candida*.

In certain embodiments of the method for enhancing efficacy of a treatment, the method further comprises administering to the subject one or more of the following (i) a probiotic and/or a prebiotic composition that stimulates growth and/or activity of one or more strains of bacteria from one or more genera selected from *Bifidobacterium*, *Faecalibacterium*, *Propionibacterium*, *Pseudoxanthomonas*, *Streptomyces*, *Saccharopolyspora* in the pancreatic microbiota of the subject;

(ii) a probiotic and/or a prebiotic composition that stimulates growth and/or activity of one or more strains of bacteria from one or more genera selected from *Akkermansia*, *Bacteroides*, *Bifidobacterium*, *Blautia*, *Brachyspira*, *Candidatus arthromitus*, *Dorea*, *Eubacterium*, *Faecalibacterium*, *Gallicola*, *Lactobacillus*, *Megamonas*, *Mollicutes* RF39, *Mycoplasma*, *Parabacteroides*, *Prevotella*, *Ruminococcus*, Tenericutes ML615J-28, and *Ureaplasma* in the gastrointestinal (GI) microbiota of the subject;

(iii) a probiotic and/or a prebiotic composition that stimulates growth and/or activity of one or more strains of bacteria from one or more species selected from *Bifidobacterium pseudolongum*, *Faecalibacterium prausnitzii*, *Bacillus clausii*, and *Propionibacterium acnes* in the pancreatic microbiota of the subject;

(iv) a probiotic and/or a prebiotic composition that stimulates growth and/or activity of one or more strains of bacteria from one or more species selected from *Akkermansia* muciniphila, *Bacteroides eggerthii*, *Bacteroides fragilis*, *Bifidobacterium adolescentis*, *Blautia producta*, *Candidatus Arthromitus*, *Eubacterium biforme*, *Faecalibacterium prausnitzii*, *Lactobacillus reuteri*, *Lactobacillus ruminis*, *Parabacteroides distasonis*, *Prevotella copri*, *Ruminococcus gnavus*, and TM7 in the gastrointestinal (GI) microbiota of the subject;

(v) a probiotic composition comprising one or more strains of bacteria from one or more genera selected from *Bifidobacterium*, *Faecalibacterium*, *Propionibacterium*, *Pseudoxanthomonas*, *Streptomyces*, *Saccharopolyspora*, *Akkermansia*, *Bacteroides*, *Bifidobacterium*, *Blautia*, *Brachyspira*, *Candidatus arthromitus*, *Dorea*, *Eubacterium*, *Faecalibacterium*, *Gallicola*, *Lactobacillus*, *Megamonas*, *Mollicutes* RF39, *Mycoplasma*, *Parabacteroides*, *Prevotella*, *Ruminococcus*, TenericutesML615J-28, and *Ureaplasma;*

(vi) a probiotic composition comprising one or more strains of bacteria from one or more species selected from *Bifidobacterium pseudolongum*, *Faecalibacterium prausnitzii*, and *Propionibacterium acnes*, *Akkermansia muciniphila*, *Bacteroides eggerthii*, *Bacteroides fragilis*, *Bifidobacterium adolescentis*, *Blautia producta*, *Candidatus Arthromitus*, *Eubacterium biforme*, *Faecalibacterium prausnitzii*, *Lactobacillus reuteri*, *Lactobacillus ruminis*, *Parabacteroides distasonis*, *Prevotella copri*, *Ruminococcus gnavus*, *Bacillus clausii*, and TM7;

(vii) a compound or composition which inhibits growth and/or activity of one or more strains of bacteria from one or more genera selected from *Bacteroides*, *Bifidobacterium*, *Chryseobacterium*, *Delftia*, *Elizabethkingia*, *Lactobacillus*, *Mucispirillum*, *Pseudomonas*, *Streptococcus*, *Fusobacterium*, and *Viellonella* in the pancreatic microbiota of the subject;

(viii) a compound or composition which inhibits growth and/or activity of one or more strains of bacteria from one or more genera selected from *Akkermansia*, *Bacteroides*, *Bifidobacterium*, *Desulfovibrio*, *Elizabethkingia*, *Escherichia*, *Lactobacillus*, *Mucispirillum*, *Oxalobacter*, *Parabacteroides*, *Peptostreptococcus*, *Prevotella*, *Pyramidobacter*, *Rothia*, *Streptococcus*, and *Viellonella* in the gastrointestinal (GI) microbiota of the subject;

(ix) a compound or composition which inhibits growth and/or activity of one or more strains of bacteria from one or more species selected from *Bacteroides acidifaciens*, *Bifidobacterium pseudolongum*, *Elizabethkingia meningoseptica*, *Lactobacillus reuteri*, *Mucispirillum schaedleri*, *Streptococcus anginosus*, *Porphyromonas gingivalis*, *Streptococcus mitis*, *Neisseria elongata*, *Helicobacter pylori*, and *Veillonella dispar* in the pancreatic microbiota of the subject; or (x) a compound or composition which inhibits growth and/or activity of one or more strains of bacteria from one or more species selected from *Akkermansia muciniphila*, *Bacteroides acidifaciens*, *Bifidobacterium animalis*, *Bifidobacterium pseudolongum*, *Desulfovibrio* D168, *Elizabethkingia meningoseptica*, *Escherichia coli*, *Lactobacillus reuteri*, *Mucispirillium schaedleri*, *Oxalobacter formigenes*, *Parabacteroides distasoni*, *Peptostreptococcus anaerobius*, *Prevotella melaninogenica*, *Prevotella stercorea*, *Pyramidobacter piscolens*, *Rothia mucilaginosa*, *Streptococcus anginosus*, and *Veillonella dispar* in the gastrointestinal (GI) microbiota of the subject.

In certain embodiments of the method for enhancing efficacy of a treatment, the treatment (i) and the first compound or composition (ii) are administered simultaneously. In certain embodiments, the treatment (i) and the first compound or composition (ii) are administered in one composition. In certain embodiments, the treatment (i) and the first compound or composition (ii) are administered simultaneously in different compositions. In certain embodiments, the treatment (i) and the first compound or composition (ii) are administered sequentially.

In certain embodiments of the method for enhancing efficacy of a treatment, the treatment (i) is selected from surgery, radiotherapy, chemotherapy, immunotherapy, and any combinations thereof. In certain embodiments, the chemotherapy is selected from FOLFIRINOX (folinic acid, 5-fluorouracil, irinotecan, oxaliplatin), gemcitabine, ABRAXANE (protein-bound paclitaxel), capecitabine, 5-fluorouracil, and any combination thereof. In certain embodiments, the immunotherapy comprises administering an immune checkpoint inhibitor. In certain embodiments, the immune checkpoint inhibitor is a programmed cell death protein 1 (PD-1) inhibitor, a programmed death-ligand 1 (PD-L1) inhibitor or a cytotoxic T-lymphocyte-associated antigen 4 (CTLA-4) inhibitor. In certain embodiments, the PD-1 inhibitor is an antibody. In certain embodiments, the antibody is pembrolizumab or nivolumab.

In various embodiments of the method for enhancing efficacy of a treatment, the subject is human.

In another aspect, provided herein is a pharmaceutical composition comprising (i) a first compound or composition which can inhibit growth and/or activity of one or more strains of fungi from the genus *Malassezia* in the pancreatic and/or gastrointestinal microbiota of a subject, and (ii) a chemotherapeutic and/or immunotherapeutic agent. In certain embodiments, said first compound or composition can inhibit growth and/or activity of one or more strains of fungi from the species *Malassezia globosa*.

In certain embodiments of the pharmaceutical composition described above, said first compound or composition comprises an antifungal compound or a natural product that inhibits fungal growth. In certain embodiments, the antifungal compound is selected from an echocandin compound, a triazole compound, and a polyene compound, and any combinations thereof. In certain embodiments, the antifungal compound is amphotericin B or fluconazole.

In certain embodiments of the pharmaceutical composition described above, the chemotherapeutic agent is selected from FOLFIRINOX (folinic acid, 5-fluorouracil, irinotecan, oxaliplatin), gemcitabine, ABRAXANE (protein-bound paclitaxel), capecitabine, 5-fluorouracil, and any combinations thereof.

In certain embodiments of the pharmaceutical composition described above, the immunotherapeutic comprises an immune checkpoint inhibitor. In certain embodiments, the immune checkpoint inhibitor is a programmed cell death protein 1 (PD-1) inhibitor, a programmed death-ligand 1 (PD-L1) inhibitor or a cytotoxic T-lymphocyte-associated antigen 4 (CTLA-4) inhibitor. In certain embodiments, the PD-1 inhibitor is an antibody. In certain embodiments, the antibody is pembrolizumab or nivolumab.

In certain embodiments of the pharmaceutical composition described above, the pharmaceutical composition further comprises a small molecule inhibitor or an antibody that inhibits the function of mannose-binding lectin (MBL)-C3 convertase complement axis selected from APL-2, compstatin Cp40, POT-4, MAb 3F8, and hMBL 1.2, and any combinations thereof.

In certain embodiments of the pharmaceutical composition described above, the pharmaceutical composition further comprises a second compound or composition that stimulates growth and/or activity of one or more strains of fungi from the genera *Saccharomyces* and *Candida* in the pancreatic and/or gastrointestinal microbiota of the subject. In certain embodiments, the pharmaceutical composition comprises one or more strains of fungi from the genera *Saccharomyces* and *Candida*.

In certain embodiments of the pharmaceutical composition described above, the pharmaceutical composition further comprises one or more of the following (i) a probiotic and/or a prebiotic composition that stimulates growth and/or activity of one or more strains of bacteria from one or more genera selected from *Bifidobacterium, Faecalibacterium, Propionibacterium, Pseudoxanthomonas, Streptomyces, Saccharopolyspora* in the pancreatic microbiota of the subject;

(ii) a probiotic and/or a prebiotic composition that stimulates growth and/or activity of one or more strains of bacteria from one or more genera selected from *Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus*, Tenericutes ML615J-28, and *Ureaplasma* in the gastrointestinal (GI) microbiota of the subject;

(iii) a probiotic and/or a prebiotic composition that stimulates growth and/or activity of one or more strains of bacteria from one or more species selected from *Bifi-*

*dobacterium pseudolongum, Faecalibacterium prausnitzii, Bacillus clausii*, and *Propionibacterium acnes* in the pancreatic microbiota of the subject;

(iv) a probiotic and/or a prebiotic composition that stimulates growth and/or activity of one or more strains of bacteria from one or more species selected from *Akkermansia* muciniphila, *Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus*, and TM7 in the gastrointestinal (GI) microbiota of the subject;

(v) a probiotic composition comprising one or more strains of bacteria from one or more genera selected from *Bifidobacterium, Faecalibacterium, Propionibacterium, Pseudoxanthomonas, Streptomyces, Saccharopolyspora, Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus*, TenericutesML615J-28, and *Ureaplasma;*

(vi) a probiotic composition comprising one or more strains of bacteria from one or more species selected from *Bifidobacterium pseudolongum, Faecalibacterium prausnitzii*, and *Propionibacterium acnes, Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus, Bacillus clausii*, and TM7;

(vii) a compound or composition which inhibits growth and/or activity of one or more strains of bacteria from one or more genera selected from *Bacteroides, Bifidobacterium, Chryseobacterium, Delftia, Elizabethkingia, Lactobacillus, Mucispirillum, Pseudomonas, Streptococcus, Fusobacterium*, and *Viellonella* in the pancreatic microbiota of the subject;

(viii) a compound or composition which inhibits growth and/or activity of one or more strains of bacteria from one or more genera selected from *Akkermansia, Bacteroides, Bifidobacterium, Desulfovibrio, Elizabethkingia, Escherichia, Lactobacillus, Mucispirillum, Oxalobacter, Parabacteroides, Peptostreptococcus, Prevotella, Pyramidobacter, Rothia, Streptococcus*, and *Viellonella* in the gastrointestinal (GI) microbiota of the subject;

(ix) a compound or composition which inhibits growth and/or activity of one or more strains of bacteria from one or more species selected from *Bacteroides acidifaciens, Bifidobacterium pseudolongum, Elizabethkingia meningoseptica, Lactobacillus reuteri, Mucispirillum schaedleri, Streptococcus anginosus, Porphyromonas gingivalis, Streptococcus mitis, Neisseria elongata, Helicobacter pylori*, and *Veillonella dispar* in the pancreatic microbiota of the subject; or (x) a compound or composition which inhibits growth and/or activity of one or more strains of bacteria from one or more species selected from *Akkermansia muciniphila, Bacteroides acidifaciens, Bifidobacterium animalis, Bifidobacterium pseudolongum, Desulfovibrio* D168, *Elizabethkingia meningoseptica, Escherichia coli, Lactobacillus reuteri, Mucispirillium schaedleri, Oxalobacter formigenes, Parabacteroides distasoni,*

*Peptostreptococcus anaerobius, Prevotella melaninogenica, Prevotella stercorea, Pyramidobacter piscolens, Rothia mucilaginosa, Streptococcus anginosus,* and *Veillonella dispar* in the gastrointestinal (GI) microbiota of the subject.

In another aspect, provided herein is a pharmaceutical dosage form comprising (i) a first compound or composition which can inhibit growth and/or activity of one or more strains of fungi from the genus *Malassezia* in the pancreatic and/or gastrointestinal microbiota of a subject, and (ii) a chemotherapeutic and/or immunotherapeutic agent. In certain embodiments, said first compound or composition can inhibit growth and/or activity of one or more strains of fungi from the species *Malassezia globosa.*

In certain embodiments of the pharmaceutical dosage form described above, said first compound or composition comprises an antifungal compound or a natural product that inhibits fungal growth. In certain embodiments, the antifungal compound is selected from an echocandin compound, a triazole compound, and a polyene compound, and any combinations thereof. In certain embodiments, the antifungal compound is amphotericin B or fluconazole.

In certain embodiments of the pharmaceutical dosage form described above, the chemotherapeutic agent is selected from FOLFIRINOX (folinic acid, 5-fluorouracil, irinotecan, oxaliplatin), gemcitabine, ABRAXANE (protein-bound paclitaxel), capecitabine, 5-fluorouracil, and any combinations thereof.

In certain embodiments of the pharmaceutical dosage form described above, the immunotherapeutic agent comprises an immune checkpoint inhibitor. In certain embodiments, the immune checkpoint inhibitor is a programmed cell death protein 1 (PD-1) inhibitor, a programmed death-ligand 1 (PD-L1) inhibitor or a cytotoxic T-lymphocyte-associated antigen 4 (CTLA-4) inhibitor. In certain embodiments, the PD-1 inhibitor is an antibody. In certain embodiments, the antibody is pembrolizumab or nivolumab.

In certain embodiments of the pharmaceutical dosage form described above, the pharmaceutical dosage form further comprises a small molecule inhibitor or an antibody that inhibits the function of mannose-binding lectin (MBL)-C3 convertase complement axis selected from APL-2, compstatin Cp40, POT-4 and/or MAb 3F8 and/or hMBL 1.2, and any combinations thereof.

In certain embodiments of the pharmaceutical dosage form described above, the pharmaceutical dosage form further comprises a second compound or composition that stimulates growth and/or activity of one or more strains of fungi from the genera *Saccharomyces* and *Candida* in the pancreatic and/or gastrointestinal microbiota of the subject. In certain embodiments, one or more strains of fungi from the genera *Saccharomyces* and *Candida.*

In certain embodiments of the pharmaceutical dosage form described above, the pharmaceutical dosage form further comprises one or more of the following (i) a probiotic and/or a prebiotic composition that stimulates growth and/or activity of one or more strains of bacteria from one or more genera selected from *Bifidobacterium, Faecalibacterium, Propionibacterium, Pseudoxanthomonas, Streptomyces, Saccharopolyspora* in the pancreatic microbiota of the subject;

(ii) a probiotic and/or a prebiotic composition that stimulates growth and/or activity of one or more strains of bacteria from one or more genera selected from *Akkermansia, Bacteroides, Bifidobacterium, Blautia, Brachyspira, Candidatus arthromitus, Dorea, Eubacterium, Faecalibacterium, Gallicola, Lactobacillus,*

*Megamonas, Mollicutes* RF39, *Mycoplasma, Parabacteroides, Prevotella, Ruminococcus,* Tenericutes ML615J-28, and *Ureaplasma* in the gastrointestinal (GI) microbiota of the subject;

(iii) a probiotic and/or a prebiotic composition that stimulates growth and/or activity of one or more strains of bacteria from one or more species selected from *Bifidobacterium pseudolongum, Faecalibacterium prausnitzii, Bacillus clausii,* and *Propionibacterium acnes* in the pancreatic microbiota of the subject;

(iv) a probiotic and/or a prebiotic composition that stimulates growth and/or activity of one or more strains of bacteria from one or more species selected from *Akkermansia* muciniphila, *Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus,* and TM7 in the gastrointestinal (GI) microbiota of the subject;

(v) a probiotic composition comprising one or more strains of bacteria from one or more genera selected from *Bifidobacterium, Faecalibacterium, Propionibacterium, Pseudoxanthomonas, Streptomyces, Saccharopolyspora, Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus,* TenericutesML615J-28, and *Ureaplasma;*

(vi) a probiotic composition comprising one or more strains of bacteria from one or more species selected from *Bifidobacterium pseudolongum, Faecalibacterium prausnitzii,* and *Propionibacterium acnes, Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus, Bacillus clausii,* and TM7;

(vii) a compound or composition which inhibits growth and/or activity of one or more strains of bacteria from one or more genera selected from *Bacteroides, Bifidobacterium, Chryseobacterium, Delftia, Elizabethkingia, Lactobacillus, Mucispirillum, Pseudomonas, Streptococcus, Fusobacterium,* and *Viellonella* in the pancreatic microbiota of the subject;

(viii) a compound or composition which inhibits growth and/or activity of one or more strains of bacteria from one or more genera selected from *Akkermansia, Bacteroides, Bifidobacterium, Desulfovibrio, Elizabethkingia, Escherichia, Lactobacillus, Mucispirillum, Oxalobacter, Parabacteroides, Peptostreptococcus, Prevotella, Pyramidobacter, Rothia, Streptococcus,* and *Viellonella* in the gastrointestinal (GI) microbiota of the subject;

(ix) a compound or composition which inhibits growth and/or activity of one or more strains of bacteria from one or more species selected from *Bacteroides acidifaciens, Bifidobacterium pseudolongum, Elizabethkingia meningoseptica, Lactobacillus reuteri, Mucispirillum schaedleri, Streptococcus anginosus, Porphyromonas gingivalis, Streptococcus mitis, Neisseria elongata, Helicobacter pylori,* and *Veillonella dispar* in the pancreatic microbiota of the subject; or (x) a compound or composition which inhibits growth and/or activity of one or more strains of bacteria from one or more species selected from *Akkermansia muciniphila, Bacteroides acidifaciens, Bifidobacterium animalis, Bifidobacterium pseudolongum, Desulfovibrio D168, Elizabethkingia meningoseptica, Escherichia coli, Lactobacillus reuteri, Mucispirillium schaedleri, Oxalobacter formigenes, Parabacteroides distasoni, Peptostreptococcus anaerobius, Prevotella melaninogenica, Prevotella stercorea, Pyramidobacter piscolens, Rothia mucilaginosa, Streptococcus anginosus,* and *Veillonella dispar* in the gastrointestinal (GI) microbiota of the subject.

In another aspect, provided herein is a method for treating a pancreatic cancer or tumor in a subject in need thereof, said method comprising administering to the subject an effective amount of the pharmaceutical composition described above.

In another aspect, provided herein is a method for treating a pancreatic cancer or tumor in a subject in need thereof, said method comprising administering to the subject the dosage form described above.

In certain embodiments of the therapeutic methods described above, said composition or dosage form is administered directly to the pancreas and/or gastrointestinal tract. In certain embodiments, said composition or dosage form is administered by a route selected from oral, rectal, sublingual, topical, intravenous, and via naso/oro-gastric gavage.

In certain embodiments of the therapeutic methods described above, wherein the subject has a functional mannose-binding lectin (MBL)-C3 convertase complement axis.

In various embodiments of the therapeutic methods described above, the subject is human.

In certain embodiments of the therapeutic methods described above, the method further comprises (a) determining the level of at least one strain of fungi from the genus *Malassezia* in the pancreatic and/or gastrointestinal microbiota of the subject, and (b) comparing the level determined in step (a) to the level of the same fungi in the control pancreatic and/or gastrointestinal microbiota. In certain embodiments, the method comprises determining the level of at least one strain of fungi from the species *Malassezia globosa*. In certain embodiments, wherein the control microbiota is microbiota of age- and/or sex- and/or ethnicity-matched healthy subjects. In certain embodiments, wherein the level of fungi is determined by a method selected from quantitative PCR (qPCR), high-throughput sequencing, transcriptomic analysis, bacterial genotype pattern based fingerprinting (DNA fingerprinting), and proteomic analysis.

In one aspect, provided herein is a method for diagnosing predisposition or determining the likelihood of development of pancreatic cancer or tumor in a subject, said method comprising (a) determining the level of at least one strain of fungi from the genus *Malassezia* in the pancreatic and/or gastrointestinal microbiota of the subject, and (b) comparing the level determined in step (a) to the level of the same fungi in the control pancreatic and/or gastrointestinal microbiota, and (c) identifying that the subject is predisposed to a pancreatic cancer or tumor, wherein the level of at least one of the strains measured in step (a) is at least 1000-fold higher than in the control.

In one aspect, provided herein is a method for determining whether a subject diagnosed with pancreatic cancer is at a high risk for cancer progression, said method comprising (a) determining the level of at least one strain of fungi from the genus *Malassezia* in the pancreatic and/or gastrointestinal microbiota of the subject, and (b) comparing the level determined in step (a) to the level of the same fungi in the control pancreatic and/or gastrointestinal microbiota, and (c) identifying that the subject is at a high risk for cancer progression, wherein the level of at least one of the strains measured in step (a) is at least 1000-fold higher than in the control.

In certain embodiments of the diagnostic methods described above, the method comprises determining the level of at least one strain of fungi from the species *Malassezia globosa*.

In certain embodiments of the diagnostic methods described above, the method further comprises (a) determining the level of at least one strain of bacteria from one or more genera selected from *Bifidobacterium, Faecalibacterium, Propionibacterium, Pseudoxanthomonas, Streptomyces, Saccharopolyspora* in the pancreatic microbiota or from one or more species selected from *Bifidobacterium pseudolongum, Faecalibacterium prausnitzii, Bacillus clausii,* and *Propionibacterium acnes* or a closely related OTU within the same genus which has at least 90% sequence identity to 16S rRNA of said species over its entire length or has at least 90% sequence identity to any single V region of 16S rRNA of said species in the pancreatic microbiota of the subject, and (b) comparing the level determined in step (a) to the level of the same bacteria in the pancreatic microbiota of healthy controls, and (c) identifying that the subject is predisposed to a pancreatic cancer or tumor wherein the level of at least one of the strains measured in step (a) is at least 35% lower than in healthy controls. In certain embodiments, the method further comprises (a) determining the level of at least one strain of bacteria from one or more genera selected from *Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes RF39, Mycoplasma, Parabacteroides, Prevotella, Ruminococcus,* Tenericutes ML615J-28, and *Ureaplasma* or one or more species selected from *Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus,* and TM7 or a closely related OTU within the same genus which has at least 90% sequence identity to 16S rRNA of said species over its entire length or has at least 90% sequence identity to any single V region of 16S rRNA of said species in the gastrointestinal (GI) microbiota of the subject, and (b) comparing the level determined in step (a) to the level of the same bacteria in the gastrointestinal (GI) microbiota of healthy controls, and (c) identifying that the subject is predisposed to a pancreatic cancer or tumor wherein the level of at least one of the strains measured in step (a) is at least 35% lower than in healthy controls. In certain embodiments, in step (c) the subject is identified as predisposed to a pancreatic cancer or tumor wherein the level of at least one of the strains measured in step (a) is at least 50% lower than in healthy controls.

In certain embodiments of the diagnostic methods described above, the method further comprises (d) determining the level of at least one strain of bacteria from one or more genera selected from *Bacteroides, Bifidobacterium, Chryseobacterium, Delftia, Elizabethkingia, Lactobacillus, Mucispirillum, Pseudomonas, Streptococcus, Fusobacterium,* and *Viellonella* or from one or more species selected from *Bacteroides acidifaciens, Bifidobacterium pseudolongum, Elizabethkingia meningoseptica, Lactobacillus reuteri, Mucispirillum schaedleri, Streptococcus anginosus,*

*Porphyromonas gingivalis, Streptococcus mitis, Neisseria elongata, Helicobacter pylori,* and *Veillonella dispar* or a closely related OTU within the same genus which has at least 90% sequence identity to 16S rRNA of said species over its entire length or has at least 90% sequence identity to any single V region of 16S rRNA of said species in the pancreatic microbiota of the subject, and (e) comparing the level determined in step (d) to the level of the same bacteria in the pancreatic microbiota of healthy controls, and (f) identifying that the subject is predisposed to a pancreatic cancer or tumor wherein the level of at least one of the strains measured in step (d) is at least 35% higher than in healthy controls. In certain embodiments, the method further comprises (d) determining the level of at least one strain of bacteria from one or more genera selected from *Akkermansia, Bacteroides, Bifidobacterium, Desulfovibrio, Elizabethkingia, Escherichia, Lactobacillus, Mucispirillum, Oxalobacter, Parabacteroides, Peptostreptococcus, Prevotella, Pyramidobacter, Rothia, Streptococcus,* and *Viellonella* or from one or more species selected from *Akkermansia muciniphila, Bacteroides acidifaciens, Bifidobacterium animalis, Bifidobacterium pseudolongum, Desulfovibrio* D168, *Elizabethkingia* meningoseptica, *Escherichia coli, Lactobacillus reuteri, Mucispirillium schaedleri, Oxalobacter* formigenes, *Parabacteroides distasoni, Peptostreptococcus anaerobius, Prevotella melaninogenica, Prevotella stercorea, Pyramidobacter piscolens, Rothia mucilaginosa, Streptococcus anginosus,* and *Veillonella dispar* or a closely related OTU within the same genus which has at least 90% sequence identity to 16S rRNA of said species over its entire length or has at least 90% sequence identity to any single V region of 16S rRNA of said species in the gastrointestinal (GI) microbiota of the subject, and (e) comparing the level determined in step (d) to the level of the same bacteria in the gastrointestinal (GI) microbiota of healthy controls, and (f) identifying that the subject is predisposed to a pancreatic cancer or tumor wherein the level of at least one of the strains measured in step (d) is at least 35% higher than in healthy controls. In certain embodiments, in step (f) the subject is identified as predisposed to a pancreatic cancer or tumor wherein the level of at least one of the strains measured in step (d) is at least 50% higher than in healthy controls.

In certain embodiments, the species has at least 95% sequence identity to the 16S rRNA over its entire length or at least 95% sequence identity to any single V region of the 16S rRNA. In certain embodiments, the species has at least 97% sequence identity to the 16S rRNA over its entire length or at least 97% sequence identity to any single V region of the 16S rRNA. In certain embodiments, the species has at least 99% sequence identity to the 16S rRNA over its entire length or at least 99% sequence identity to any single V region of the 16S rRNA. In certain embodiments, the V region of 16S rRNA is the V4 region.

In certain embodiments of the diagnostic methods described above, the control microbiota is microbiota of age- and/or sex- and/or ethnicity-matched healthy subjects.

In certain embodiments of the diagnostic methods described above, the pancreatic cancer is pancreatic ductal adenocarcinoma (PDA).

In certain embodiments of the diagnostic methods described above, the subject has a functional mannose-binding lectin (MBL)-C3 convertase complement axis.

In certain embodiments of the diagnostic methods described above, the level of fungi and/or bacteria is determined by a method selected from quantitative PCR (qPCR), high-throughput sequencing, transcriptomic analysis, bacterial genotype pattern based fingerprinting (DNA fingerprinting), and proteomic analysis.

In certain embodiments of the diagnostic methods described above, the method further comprises recruiting the subject in a clinical trial.

In certain embodiments of the diagnostic methods described above, the method further comprises administering a pancreatic cancer or tumor treatment to the subject. In certain embodiments, the treatment comprises any of the treatment methods described herein.

In various embodiments of the diagnostic methods described above, the subject is human.

These and other aspects of the present invention will be apparent to those of ordinary skill in the art in the following description, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A, The abundance of intrapancreatic fungi was compared between healthy individuals (healthy) and patients with PDA who were matched for age, gender and body mass index, using fluorescent in situ hybridization (FISH). n=3 individuals per group. Representative images are shown. Scale bar, 20 μm. FIG. 1B, The abundance of intrapancreatic fungi was compared in three-month-old, littermate wild-type (WT) and p48$^{cre}$;LSL-Kras$^{G12D}$ (p48 is also known as Ptf1a) mice (hereafter referred to as KC mice) by FISH. Representative images are shown. n=3 mice per group. Scale bar, 20 μm. FIG. 1C, Fungal DNA content was compared in the pancreata of healthy individuals and patients with PDA who were matched for age, gender and body mass index, using quantitative PCR (qPCR). Data are mean±s.e.m. Two-tailed Student's t-test. FIG. 1D, Fungal DNA content was compared in the pancreata of three-month-old wild-type and KC mice, using qPCR. Data are mean±s.e.m. Two-tailed Student's t-test. FIG. 1E, GFP-labeled *S. cerevisiae* was administered to wild-type (n=15) and KC (n=9) mice via oral gavage. Pancreata were collected at 30 min, and the number of GFP$^+$ foci was determined by flow cytometry in comparison to mock-treated mice (control, n=6 mice). This experiment was repeated twice. Data are mean±s.e.m. Two-tailed Student's t-test. FIGS. 1F-1I, The gut (n=14 biologically independent samples) and intrapancreatic (n=11 biologically independent samples) mycobiomes of 30-week-old KC mice were analyzed by 18S internal transcribed space (ITS) sequencing. FIG. 1F, PCoA plots based on a Bray-Curtis dissimilarity matrix. Each symbol represents a sample from the gut (red) or pancreas (blue). Clusters were determined by pairwise permutational analysis of variance (PERMANOVA). The x and y axes indicate percent variation, and the ellipses indicate the 95% confidence interval. FIG. 1G, The gut and intrapancreatic mycobiomes in 30-week-old KC mice were analyzed for alpha-diversity measures, including observed operational taxonomic units (OTUs) and Shannon indices. Two-sided Wilcoxon rank-sum test. Box plots show median, 25th and 75th percentiles, and whiskers that extend to 1.5× the interquartile range. FIG. 1H, Taxonomic composition of mycobiota assigned to the phylum level, on the basis of their average percent relative abundance. NS, not significant. Data are mean±s.e.m. Two-tailed Student's t-test. FIG. 1I, Heat map showing log 2-transformed relative abundancies of the top 20 fungal genera in the gut and pancreata. FIGS. 1J-1L, PCoA plots of fungal communities in feces of 6-week-old (FIG. 1J), 18-week-old (FIG. 1K) and 30-week-old (FIG. 1L) wild-type and KC mice, based on a Bray-Curtis dissimilarity matrix. Clusters were determined by pairwise PERMANOVA. The x andy axes indicate percent variation, and the ellipses indicate the 95% confidence interval.

FIGS. 2A-2D, Gut (n=18) and tumor (n=13) specimens from patients with PDA were analyzed by 18S ITS sequencing. FIG. 2A, Taxonomic composition of mycobiota assigned to the phylum level, on the basis of their average percent relative abundance. Data are mean±s.e.m. Two-tailed Student's t-test. FIG. 2B, Hierarchical tree cladogram, depicting differences between the gut and tumors in terms of the taxonomic composition of mycobiota assigned to the genus level (on the basis of their average percent relative abundance). FIG. 2C, The gut and tumor mycobiomes of patients with PDA were tested for alpha-diversity measures, including observed OTUs, abundance-based coverage estimates (ACE), and the Chao1, Shannon and Simpson indices. Two-sided Wilcoxon rank-sum test. Box plots show median, 25th and 75th percentiles, and whiskers that extend to the maximum and minimum data points. FIG. 2D, PCoA plots of gut (n=18) and intratumoral (n=13) fungal communities in patients with PDA, based on a Bray-Curtis dissimilarity matrix. FIG. 2E, PCoA plots of fungal communities in pancreata of patients with PDA (n=13) and healthy individuals (n=5), based on a Bray-Curtis dissimilarity matrix. Analyses were determined by pairwise PERMANOVA. The x and y axes indicate percent variation, and the ellipses indicate the 95% confidence interval.

FIGS. 3A-3D. Fungal dysbiosis promotes pancreatic oncogenesis. FIG. 3A, KC mice treated with amphotericin B (ampho.) or vehicle were killed at three months old. Pancreatic weights (of n=5 mice treated with amphotericin B and 11 mice treated with vehicle) were recorded. Representative sections stained with hematoxylin and eosin (H & E), or using trichrome staining, are shown. The percentage of preserved acinar area, and the fraction of normal ducts, acinoductal metaplasia (ADM) and graded (I and II) pancreatic intra-epithelial neoplasia (PanIN) lesions were determined on the basis of H & E staining. Scale bar, 200 μm. The fraction of fibrotic area per pancreas was calculated on the basis of trichrome staining. Scale bar, 200 μm. Data are mean±s.e.m. Two-tailed Student's t-test. FIG. 3B, Wild-type mice that bear orthotopic PDA tumors were treated with vehicle or amphotericin B (n=16 mice per group, data pooled from 3 independent experiments) and killed three weeks later. Tumors were collected and weighed. Data are representative of experiments repeated more than five times. Scale bar, 1 cm. Data are mean±s.e.m. Two-tailed Student's t-test. FIG. 3C, Wild-type mice that bear orthotopic PDA tumors were treated with vehicle (n=9 mice), amphotericin B (n=6 mice), gemcitabine (gem.) (n=8 mice) or amphotericin B and gemcitabine (ampho.+gem.) (n=6 mice). Tumor weight was recorded after three weeks of treatment. Scale bar, 1 cm. Data are mean±s.e.m. Two-tailed Student's t-test. FIG. 3D, Wild-type mice treated with amphotericin B were repopulated with *M. globosa* (n=8 mice), *S. cerevisiae* (n=9 mice), *Candida* sp. (n=8 mice), *Aspergillus* sp. (n=10 mice) or vehicle (n=8 mice), and killed three weeks later. Tumors were collected and weighed. Data are representative of experiments that were repeated twice. Scale bar, 1 cm. Data are mean±s.e.m. Two-tailed Student's t-test.

FIGS. 4A-4L. Fungi promote progression of PDA via the MBL-C3 axis. FIG. 4A, KC (KC; Mbl$^{+/+}$, n=11; used as control) and KC, MBL-null (KC; Mbl$^{-/-}$, n=7) mice were killed at three months old. Tumors were weighed and stained using H & E, or trichrome staining, and analyzed for pancreatic dysplasia and fibrosis as in FIG. 3A. Data for control KC mice are the same those shown for the vehicle treatment in FIG. 3. Data are mean±s.e.m. Two-tailed Student's t-test. Scale bars, 200 μm. FIGS. 4B, 4C, Wild-type and MBL-null mice were administered orthotopic tumor cells from a KPC mouse, and analyzed for tumor growth at three weeks (n=22 cells per arm; data represent mean±s.e.m., two-tailed Student's t-test) (FIG. 4B) and survival (n=8 wild-type and 5 MBL-null mice; log-rank test) (FIG. 4C). Data are representative of experiments repeated more than five times. FIG. 4D, Mb/host mice were administered orthotopic tumors from Pdx1$^{cre}$;Kras$^{G12D}$;Tp53$^{R172H}$ (Tp53 is also known as Trp53) mice (hereafter, KPC mice), received intratumoral injections of recombinant C3a (rC3a) (n=6 mice) or vehicle (n=6 mice) on day 14 via laparotomy, and then volumes were measured. Tumors were collected on day 21, and the change in tumor volume since the injection was calculated. This experiment was repeated twice. Data are mean±s.e.m. Two-tailed Student's t-test. FIG. 4E, Wild-type (n=10) and C3$^{-/-}$ (n=9) mice were administered orthotopic tumors from KPC mice, and analyzed for tumor growth at three weeks. Data are representative of experiments that were repeated three times. Data are mean±s.e.m. Two-tailed Student's t-test.

FIG. 4F, 4G, Wild-type mice were orthotopically implanted with tumor cells from KPC mice, treated with short hairpin (sh)RNA directed against C3aR (also known as C3ar1) or with control scrambled shRNA. Separate shRNA vectors were used for each treatment. FIG. 4F, The efficacy of C3aR knockdown was measured by qPCR (n=3 mice per group). Data are mean±s.e.m. Two-tailed Student's t-test. FIG. 4G, Quantitative analysis of tumor weights at day 21 is shown (n=9 mice for treatment with scrambled shRNA, and n=5 mice from treatment with C3aR shRNA no. 1 and C3aR shRNA no. 2). Data are mean±s.e.m. Two-tailed Student's t-test. FIG. 4H, Wild-type and C3$^{-/-}$ mice treated with vehicle (n=3 wild-type mice, 4 C3$^{-/-}$ mice) or amphotericin B (n=4 mice of each background) were administered orthotopic tumors from KPC mice, and killed three weeks later. Tumors were collected and weighed. Data are representative of experiments that were repeated twice. Data are mean±s.e.m. Two-tailed Student's t-test. FIG. 4I, Schematic depicts the mycobiome-MBL axis in pancreatic oncogenesis.

FIGS. 7A-7F. Efficacy of antifungal treatments in pancreatic disease. FIG. 7A, Wild-type mice that bear orthotopic PDA tumors were treated with vehicle (n=7 mice) or fluconazole (n=8 mice), and killed three weeks later. Tumors were collected and weighed. Data are representative of experiments that were performed twice. Scale bar, 1 cm. Data are mean±s.e.m. Two-tailed Student's t-test. FIG. 7B, Germ-free wild-type mice were treated with amphotericin B (n=6 mice) or vehicle (n=10 mice), and orthotopic tumors from KPC mice were administered to them. Mice were killed three weeks later, and tumors were collected and weighed. Scale bar, 1 cm. Data are mean±s.e.m. Two-tailed Student's t-test. FIGS. 7C-7E, Wild-type mice induced to develop cerulein-induced pancreatitis were serially treated with amphotericin B (n=5 mice) or vehicle (n=3 mice). FIG. 7C, Representative H & E-stained sections of pancreata are shown, and pancreatic oedema was quantified by measuring the percentage of the area that was white space. Scale bar, 100 μm. FIG. 7D, CD45⁺ inflammatory-cell infiltration was determined by immunohistochemistry. Scale bar, 20 μm. FIG. 7E, Serum amylase was measured. n=5 mice treated with amphotericin B, n=3 mice treated with vehicle and n=3 mock-treated (control) mice. Data are mean±s.e.m. Two-tailed Student's t-test. FIG. 7F, Wild-type mice treated with amphotericin B were repopulated with *C. tropicalis* (n=4 mice) or vehicle (n=4 mice), and killed three weeks later. Tumors were collected and weighed. Scale bar, 1 cm. Data are mean±s.e.m. Two-tailed Student's t-test.

FIGS. 8A-8F. Fungal dysbiosis drives the progression of PDA via the lectin pathway. FIG. 8A, Kaplan-Meier survival curve of patients with PDA, stratified by high (n=16 patients), medium-high (n=24 patients), medium-low (n=26 patients) and low (n=17 patients) expression of MBL on the basis of data from TCGA. Two-tailed log-rank test. FIG. 8B, Orthotopic tumors from KPC mice were administered to MBL-null mice treated with vehicle (n=3 mice) or amphotericin B (n=4 mice), and killed three weeks later. Tumors were collected and weighed. Data are representative of three separate experiments. Data are mean±s.e.m. Two-tailed Student's t-test. FIG. 8C, MBL-null mice treated with amphotericin B were repopulated with *M. globosa* (n=5 mice) or sham-repopulated (n=4 mice), and killed three weeks later. Tumors were collected and weighed. Data are representative of experiments that were repeated twice. Data are mean±s.e.m. Two-tailed Student's t-test. FIG. 8D, Kaplan-Meier survival curve of patients with PDA, stratified by high (n=18) versus low (n=15) expression of C3, on the basis of data from TCGA. Two-tailed log-rank test. FIG. 8E, Pancreata from three-month-old wild-type, KC and KC; MbI- mice were stained using a monoclonal antibody against C3a. Representative images from two experiments are shown. Scale bar, 20 μm. FIG. 8F, KPC tumor cells were seeded in 96-well plates with vehicle or recombinant mouse C3a. n=5 cells per group for each time point. Cellular proliferation was measured at serial time points using the XTT assay. Data are mean±s.e.m. Two-tailed Student's t-test. Data are representative of experiments that were repeated three times.

FIGS. 9A-9D. Sequence match of *Malassezia globosa* from human samples (FIGS. 9A-9B) or mice samples (FIGS. 9C-9D) and ATTC strain used in repopulation experiments. FIGS. 9A-9D disclose SEQ ID NOS 7, 7, 8, 8, 9, 9, 10 and 10, respectively, in order of appearance.

DETAILED DESCRIPTION

Figure 1A:
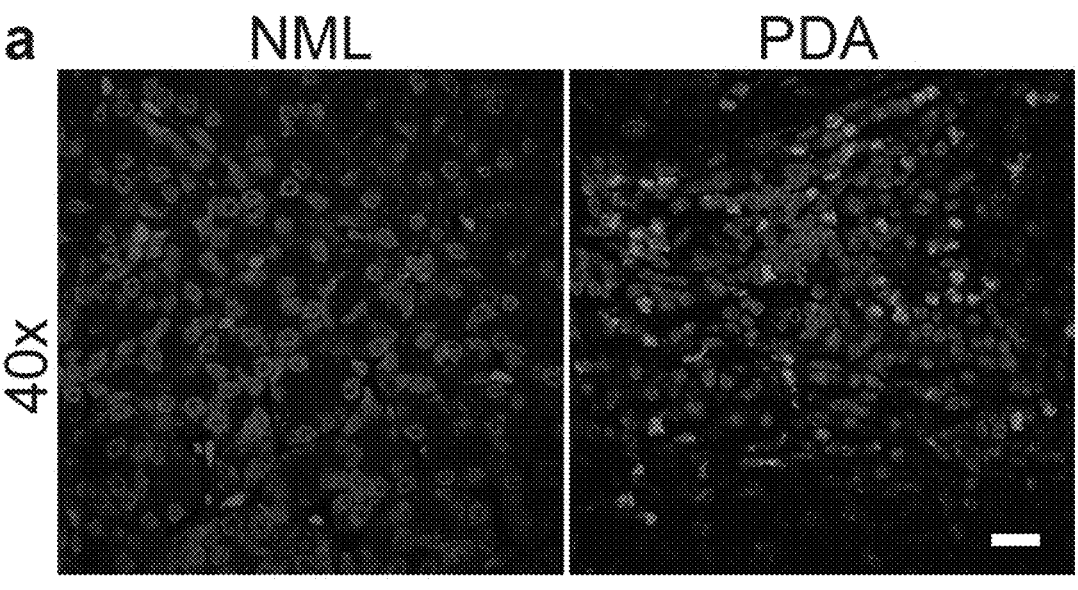
FIGS. 1A-1L. PDA is characterized by a distinctive intratumoral and gut mycobiome.
Figure 1B:
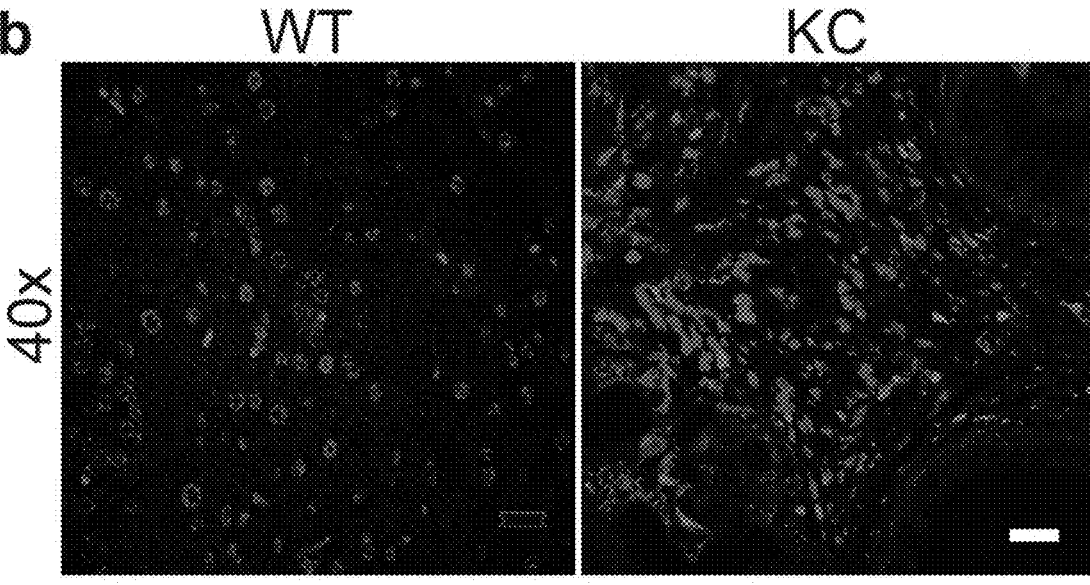
Figure 1C:
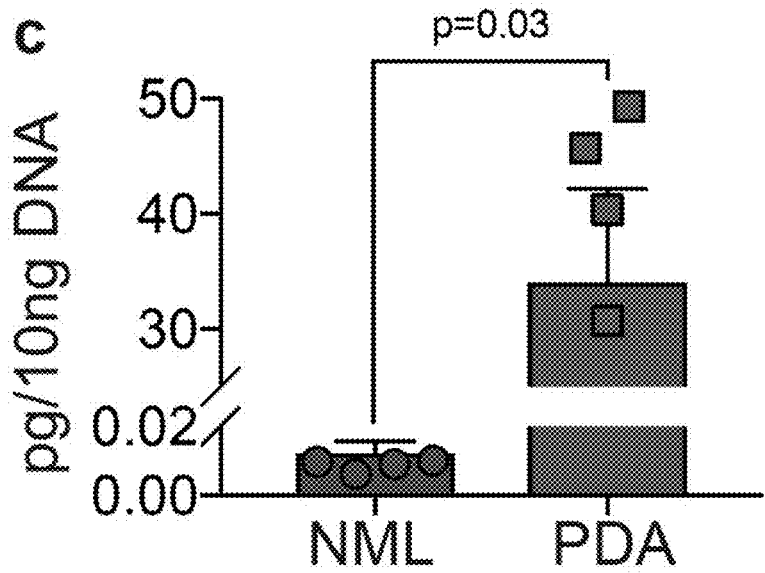
Figure 1D:
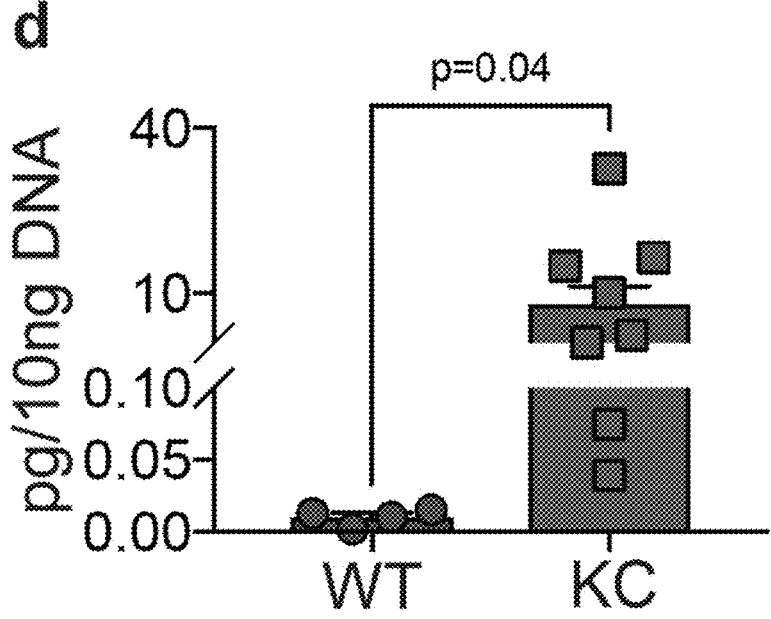

The present disclosure provides methods and compositions for diagnosing and treating (including preventing) pancreatic cancers such as pancreatic ductal adenocarcinoma (PDA).

The present disclosure is based on an unexpected discovery that fungi migrate from the gut lumen to the pancreas, and that this is implicated in the pathogenesis of PDA. Data in support of each of these findings is presented in the Examples section, below. For instance, PDA tumors in humans—and tumors in mouse models of this cancer—displayed an increase in fungi of about 3,000-fold compared to normal pancreatic tissue. The Example below demonstrates that the composition of the mycobiome of PDA tumors was distinct from that of the gut or normal pancreas on the basis of alpha- and beta-diversity indices. Specifically, the fungal community that infiltrated PDA tumors was markedly enriched for species of *Malassezia* in both mice and humans. It was discovered that, for example, ablation of the mycobiome was protective against tumor growth in slowly progressive and invasive models of PDA, and repopulation with *Malassezia* species—but not species in the genera *Candida, Saccharomyces* or *Aspergillus*—accelerated oncogenesis. It was also discovered that ligation of mannose-binding lectin (MBL), which binds to glycans of the fungal wall to activate the complement cascade, was required for oncogenic progression, whereas deletion of MBL or C3 in the extratumoral compartment—or knockdown of C3aR in tumor cells—were both protective against tumor growth. In addition, reprogramming of the mycobiome did not alter the progression of PDA in Mbl- or C3-deficient mice. The Example disclosed herein shows that pathogenic fungi promote PDA by driving the complement cascade through the activation of MBL.

Definitions

As used herein, the terms "microbe" or "microorganism" encompass both prokaryotic organisms including bacteria and archaea, and eukaryotic organisms, including fungi, present in mammalian microbiota, and viruses.

As used herein, the terms "mycobiome", "mycobiota", and "fungal microbiome" are used interchangeably and refer to the fungal community in and on an organism.

The terms "gastrointestinal microbiota", "GI microbiota", "intestinal microbiota", "intestinal flora", "intestinal microbiome", and "gut microbiome", are used interchangeably and refer to the microorganisms that colonize the intestines.

The terms "pancreatic microbiota", "pancreatic flora", and "pancreatic microbiome" are used interchangeably and refer to the microorganisms that colonize the pancreas.

The terms "gut mycobiome" and "gut fungal microbiome" are used interchangeably and refer to the fungal community that colonize the intestines.

The terms "pancreatic mycobiome" and "pancreatic fungal microbiome" are used interchangeably and refer to the fungal community that colonize the pancreas.

As used herein, the term "dysbiosis" refers to a microbial imbalance on or inside the body. Dysbiosis can result from, e.g., antibiotic exposure, cancer, as well as other causes, e.g., infections with pathogens including viruses, bacteria and eukaryotic parasites, e.g., inflammation including inflammation in cancer.

Specific taxa and changes in pancreatic microbiota discussed herein can be detected using various methods, including without limitation quantitative PCR or high-throughput sequencing methods which detect over- and under-represented genes in the total bacterial population (e.g., 454-sequencing for community analysis; screening of microbial 16S ribosomal RNAs (16S rRNA) or 28S rRNA, etc.), or transcriptomic or proteomic studies that identify lost or gained microbial transcripts or proteins within total microbial populations. See, e.g., U.S. Patent Publication No. 2010/0074872; Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703, each of which is herein incorporated by reference in its entirety for all intended purposes.

As used herein, the term "16S rRNA sequencing" refers to the sequencing of 16S ribosomal RNA (rRNA) gene sequences by using primers such as universal primers and/or species-specific primers to identify the bacteria present in a sample. 16S rRNA genes contain both highly conserved sites and hypervariable regions that can provide species-specific signature sequences useful for identification of bacteria. Such universal primers are well known in the art.

As used herein, the term "operational taxonomic unit" or "OTU" refers to group of bacterial sequences that differ among each other in <97% identity. A "type" or a plurality of "types" of bacteria includes an OTU or a plurality of different OTUs, and also encompasses differences in species, genus, family or order of bacteria. The specific genetic sequence may be the 16S rRNA sequence or a portion of the 16S rRNA sequence or it may be a functionally conserved housekeeping gene found broadly across the eubacterial kingdom.

As used herein, the term "probiotic" refers to a substantially pure bacteria (i.e., a single isolate, of, e.g., live bacterial cells, conditionally lethal bacterial cells, inactivated bacterial cells, killed bacterial cells, spores, recombinant carrier strains), or a mixture of desired bacteria, bacteria components or bacterial extract, or bacterially-derived products (natural or synthetic bacterially-derived products such as, e.g., bacterial antigens or metabolic products) and may also include any additional components that can be administered to a mammal. Such compositions are also referred to herein as bacterial inoculants" or "microbiota inoculants". Probiotics or bacterial inoculant compositions of the invention may be administered with a buffering agent to allow the bacteria to survive in the acidic environment of the stomach, i.e., to resist low pH and to grow in the intestinal environment. Such buffering agents include sodium bicarbonate, juice, milk, yogurt, infant formula, and other dairy products.

As used herein, the term "prebiotic" refers to an agent that simulates the growth (e.g., increases the number) and/or activity of one or more desired bacteria. Non-limiting examples of prebiotics useful in the methods of the present invention include fructooligosaccharides (e.g., oligofructose, inulin, inulin-type fructans), galactooligosaccharides, human milk oligosaccharides (HMO), Lacto-N-neotetraose, D-Tagatose, xylo-oligosaccharides (XOS), arabinoxylan-oligosaccharides (AXOS), N-acetylglucosamine, N-acetyl-galactosamine, glucose, other five- and six-carbon sugars (such as arabinose, maltose, lactose, sucrose, cellobiose, etc.), amino acids, alcohols, resistant starch (RS), water-soluble cellulose derivatives (most preferably, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose), water-insoluble cellulose derivatives (most preferably, ethyl cellulose), and mixtures thereof. See, e.g., Ramirez-Farias et al., Br J Nutr (2008) 4:1-10; Pool-Zobel and Sauer, J Nutr (2007), 137:2580S-2584S, each of which is herein incorporated by reference in its entirety for all intended purposes.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "therapeutically effective amount" refers to the amount of a compound (e.g., an antifungal compound) or a composition that, when administered to a subject for treating (e.g., preventing or ameliorating) a state, disorder or condition, is sufficient to effect such treatment. The "therapeutically effective amount" will vary depending, e.g., on the compound, or analogues administered as well as the disease, its severity, and physical conditions and responsiveness of the subject to be treated.

As used herein, the phrase "pharmaceutically acceptable" refers to molecular entities and compositions that are generally regarded as physiologically tolerable.

As used herein, the term "combination" of a compound (e.g., an antifungal compound) and at least a second pharmaceutically active ingredient means at least two, but any desired combination of compounds can be delivered simultaneously or sequentially (e.g., within a 24 hour period).

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

As used herein, the term "stimulate" when used in connection with growth and/or activity of microorganisms (e.g., fungi or bacteria) encompasses the term "enhance".

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The terms "a," "an," and "the" do not denote a limitation of quantity, but rather denote the presence of "at least one" of the referenced item.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ. Additional techniques are explained, e.g., in U.S. Pat. No. 7,912,698 and U.S. Patent Appl. Pub. Nos. 2011/0202322 and 2011/0307437, each of which is herein incorporated by reference in its entirety for all intended purposes.

Therapeutic Methods of the Invention

In one aspect, the disclosure provides a method for treating (including preventing) pancreatic cancer or tumors in a subject in need thereof, said method comprising administering to the subject an effective amount of a compound or composition, wherein the compound or composition inhibits growth and/or activity of one or more strains of fungi from the genus *Malassezia* in the pancreatic and/or gastrointestinal microbiota of the subject. In certain embodiments, the compound or composition inhibits growth and/or activity of at least 2, 3, 4, 5, 6, 7, 8, 9, 10, 20, 50 or more strains of fungi from the genus *Malassezia*. In certain embodiments, the compound or composition inhibits growth and/or activity of one or more strains of fungi from the species *Malassezia globose*. In certain embodiments, the pancreatic cancer is pancreatic ductal adenocarcinoma (PDA).

In certain embodiment, the growth is inhibited to the extent that the fungal strains are removed from the pancreatic and/or gastrointestinal microbiota (i.e., reduced or ablated).

In certain embodiments, the compound or composition comprises an antifungal compound or a natural product that inhibits fungal growth.

In certain embodiments, inhibiting growth and/or activity of at least one fungi species in the pancreatic and/or gastrointestinal microbiota according to any of the above methods involving such inhibition can be achieved, e.g., by administering an antifungal compound. In certain embodiments, the antifungal compound is administered in a therapeutic dose. In certain embodiment, the antifungal compound is administered in a sub-therapeutic dose.

Antifungal compounds useful in the methods and/or compositions of the invention include, but are not limited to, echocandin compounds (e.g., micafungin, caspofungin, cilofungin, and anidulafungin), triazole compounds (e.g., fluconazole, itraconazole, voriconazole, hexaconazole, isavuconazole, posaconazole, and ketoconazole), polyene compounds (e.g., amphotericin B, nystatin, and natamycin), and any combinations thereof.

Additional non-limiting examples of antifungal compound useful in the methods and/or compositions of the invention include flucytosine, azoles and echinocandins, and include specific compounds voriconazole, fluconazole, terbinafine, caspofungin, natamycin, amphotericin (e.g., amphotericin B), 5-FC, micafungin, anidulafungin, clotrimazole, isavuconazonium, itraconazole, flucytosine, griseofulvin, posaconazole, APX001, AR-12, ASP2397, efungumab, F901318, MGCD290, and T-2307.

Natural products that inhibit fungal growth useful in the methods and/or compositions of the invention include, but are not limited to, citronella, naftifine and terbinafine.

In certain embodiments, the antifungal compound is amphotericin B or fluconazole. In certain embodiments, the antifungal compound is administered from about 0.05 mg/ml to about 10 mg/ml per day. In certain embodiments, the antifungal compound is administered from about 0.075 mg/ml to about 8 mg/ml per day, about 0.1 mg/ml to about 6 mg/ml per day, about 0.25 mg/ml to about 5 mg/ml per day, about 0.5 mg/ml to about 4 mg/ml per day, about 0.75 mg/ml to about 3 mg/ml per day, or about 1 mg/ml to about 2 mg/ml per day. In certain embodiments, the antifungal compound is administered from about 0.5 mg/ml to about 1 mg/ml per day. In certain embodiments, the antifungal compound is administered at about 0.05 mg/ml, about 0.075 mg/ml, about 0.1 mg/ml, about 0.25 mg/ml, about 0.5 mg/ml, about 0.6 mg/ml, about 0.75 mg/ml, about 0.8 mg/ml, about 1.0 mg/ml, about 1.25 mg/ml, about 1.5 mg/ml, about 1.75 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, or about 10 mg/ml per day. In certain embodiments, the antifungal compound is administered for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, or about 28 days. In certain embodiments, the antifungal compound is administered consecutive days, every other day, every third day, every fourth day, or once a week. In one specific embodiment, the method comprises administering amphotericin B at 1 mg/ml per day for five consecutive days. In another specific embodiment, the method comprises administering fluconazole at 0.5 mg/ml per day for three weeks.

In one embodiment of any of the above methods of the invention, the compound or composition is administered directly to the pancreas. In certain embodiments, the compound or composition is administered to the subject by a route selected from the group consisting of oral, rectal (e.g., by enema), mucosal, topical, sublingual, intravenous and via naso/oro-gastric gavage.

In certain embodiments, the subject has a functional mannose-binding lectin (MBL)-C3 convertase complement axis. Without wishing to be bound by theory, the administered compound or composition may inhibit the function of mannose-binding lectin (MBL)-C3 convertase complement axis systemically or in the pancreas of the subject. In certain embodiments, the function of mannose-binding lectin (MBL)-C3 convertase complement axis is inhibited using a small molecule inhibitor or an antibody. Such small molecule inhibitors or antibodies may include APL-2 (see e.g., ClinicalTrials U.S. government website Identifier: NCT03500549), compstatin Cp40 (see e.g., ClinicalTrials U.S. government website Identifier: NCT03316521), POT-4 (see e.g., ClinicalTrials U.S. government website Identifier: NCT00473928; all small molecule inhibitors of C3), MAb 3F8 (see e.g., ClinicalTrials U.S. government website Identifier: 01419834), and/or hMBL 1.2 (see e.g., U.S. Pat. No. 7,273,925, which is hereby incorporated by reference in its entirety) or any combinations thereof.

In certain embodiments, the method described herein encompasses administering two or more compounds or compositions that inhibit growth and/or activity of one or more strains of fungi to the same subject. Such compounds or compositions can be administered simultaneously or sequentially.

In one embodiment of any of the above methods of the invention, the compound or composition that inhibit growth and/or activity of one or more strains of fungi is administered in a therapeutically effective amount. The dosages of the compound or composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semiweekly, etc., to maintain an effective dosage level. It is contemplated that a variety of doses will be effective to reduce or eradicate colonization.

In one embodiment of any of the above methods of the invention, the compound or composition is delivered to the subject in a form of a composition which comprises a carrier and/or excipient.

In certain embodiments of any of the above methods of the invention, the method further comprises administering a compound or composition that stimulates growth and/or activity of one or more strains of fungi from the genera *Saccharomyces* and *Candida* in the pancreatic and/or gastrointestinal microbiota of the subject. In certain embodiments, the method comprises administering to the subject a composition comprising one or more strains of fungi from the genera *Saccharomyces* and *Candida*.

In certain embodiments of any of the above methods of the invention, the method further comprises administering a probiotic and/or a prebiotic composition, wherein the composition(s) stimulate growth and/or activity of one or more strains of bacteria in the pancreatic and/or gastrointestinal microbiota, or a compound or composition, wherein the compound or composition inhibits growth and/or activity of one or more strains of bacteria in the pancreatic and/or gastrointestinal microbiota.

Probiotic and/or prebiotic compositions useful in the methods and/or compositions of the invention include those described in the International Application PCT/US18/17052, which is incorporated herein by reference in its entirety for all purposes.

Compound or compositions that inhibit growth and/or activity of one or more strains of bacteria in the pancreatic and/or gastrointestinal microbiota include those described in the International Application PCT/U18/17052, which is incorporated herein by reference in its entirety for all purposes.

In certain embodiments of any of the above methods involving administration of a probiotic composition, the probiotic comprises one or more strains of bacteria from the taxa listed in Table 1. In certain embodiments, the probiotic comprises at least 2, 3, 4, 5, 6, 7, 8, 9, 10, 20, 50 or more strains from the taxa listed in Table 1. In some embodiments, the probiotic composition comprises one or more OTUs which are independently characterized by, i.e., at least 95%, 96%, 97%, 98%, 99% or including 10000 sequence identity to 16S rRNA sequences of the bacteria recited in Table 1.

TABLE 1

| Taxa for Inclusion in Compositions and Methods for Treating (Including Preventing) PDA | | |
|---|---|---|
| Phylum | | |
| Actinobacteria | Bacteroidetes | Firmicutes |
| Spirochaetes | Tenericutes | TM7 |
| Verrucomicrobia | | |
| Class | | |
| Actinobacteria | Bacteroidia | Bacilli |
| Brachyspirae | Clostridia | Erysipelotrichi |
| Mollicutes | RF3 | TM7-3 |
| Verrucomicrobiae | | |
| Order | | |
| Actinomycetales | Bacteroidales | Bifidobacteriales |
| Brachyspirales | Clostridiales | Erysipelotrichales |
| Lactobacilluses | ML615J-28 | Mycoplasmatales |
| RF39 | TM7 CW040 | Verrucomicrobiales |
| Family | | |
| Bifidobacteriaceae | Bacteroidaceae | Brachyspiraceae |
| Clostridiaceae | Erysipelotrichaceae | Lachnospiraceae |
| Lactobacilluseae | Mycoplasmataceae | Peptoniphilaceae |
| Porphyromonadaceae | Prevotellaceae | Propionibacteriaceae |
| Ruminococcaceae | Selenomonadaceae (Veillonellaceae) | TM7 F16 |
| Verrucomicrobiaceae | | |
| Genera | | |
| Akkermansia | Bacteroides | Bifidobacterium |
| Blautia | Brachyspira | Candidatus arthromitus |
| Dorea | Eubacterium | Faecalibacterium |
| Gallicola | Lactobacillus | Megamonas |
| Mollicutes RF39 | Mycoplasma | Parabacteroides |
| Prevotella | Propionibacterium | Ruminococcus |
| Tenericutes | ML615J-28 | Ureaplasma |
| Species | | |
| Akkermansia muciniphila | Bacteroides eggerthii | Bacteroides fragilis |
| Bifidobacterium adolescentis | Bifidobacterium pseudolongum | Blautia producta |
| Candidatus arthromitus | Eubacterium biforme | Faecalibacterium prausnitzii |
| Lactobacillus reuteri | Lactobacillus ruminis | Parabacteroides distasonis |
| Prevotella copri | Propionibacterium acnes | Ruminococcus gnavus |
| TM7 | | |

In certain embodiments of any of the above methods involving administration of a compound or composition that inhibits growth and/or activity of one or more strains of bacteria, the compound or composition inhibits growth and/or activity of one or more strains of bacteria from the taxa listed in Table 2. In certain embodiments, the compound or composition inhibits growth and/or activity of at least 2, 3, 4, 5, 6, 7, 8, 9, 10, 20, 50 or more strains from the taxa listed in Table 2. In certain embodiments, the compound or composition inhibits growth and/or activity of one or more strains of bacteria of Table 2 or a closely related OTUs which are independently characterized by, i.e., at least 9500, 9600, 9700 980%, 9900 or including 10000 sequence identity to 16S rRNA sequences of the bacteria recited in Table 2.

TABLE 2

Taxa for Ablation or Anti-Bacterial Treatment to Treat and/or
Prevent Pancreatic Cancer (e.g., PDA)

| Phylum | | |
| --- | --- | --- |
| Actinobacteria | Bacteroidetes | Deferribacteres |
| Euryarchaeota | Firmicutes | Fusobacteria |
| Proteobacteria | Synergistetes | TM7 |
| Verrucomicrobia | | |

| Class | | |
| --- | --- | --- |
| Actinobacteria | Bacilli | Bacteroidia |
| Betaproteobacteria | Clostridia | Deferribacteres |
| Deltaproteobacteria | Flavobacteria | Gammaproteobacteria |
| Synergistia | Verrucomicrobiae | |

| Order | | |
| --- | --- | --- |
| Actinomycetales | Bacteroidales | Bifidobacteriales |
| Burkholderiales | Clostridiales | Deferribacterales |
| Desulfovibrionales | Enterobacteriales | Flavobacteriales |
| Lactobacillus | Pseudomonadales | Synergistales |
| Verrucomicrobiales | | |

| Family | | |
| --- | --- | --- |
| Bacteroidaceae | Bifidobacteriaceae | Deferribacteraceae |
| Desulfovibrionaceae | Dethiosulfovibrionaceae | Enterobacteriaceae |
| Enterococcaceae | Helicobacteraceae | Lactobacilluseae |
| Micrococcaceae | Mogibacteriaceae | Mycoplasmataceae |
| Oxalobacteraceae | Peptostreptococcaceae | Porphyromonadaceae |
| Prevotellaceae | Pseudomonadaceae | Streptococcaceae |
| Veillonellaceae | Verrucomicrobiaceae | Weeksellaceae |

| Genera | | |
| --- | --- | --- |
| Akkermansia | Bacteroides | Bifidobacterium |
| Chryseobacterium | Delftia | Desulfovibrio |
| Elizabethkingia | Escherichia | Lactobacillus |
| Mucispirillum | Oxalobacter | Parabacteroides |
| Peptostreptococcus | Prevotella | Pseudomonas |
| Pyramidobacter | Rothia | Streptococcus |
| Viellonella | | |

| Species | | |
| --- | --- | --- |
| Akkermansia muciniphila | Bacteroides acidifaciens | Bifidobacterium animalis |
| Bifidobacterium pseudolongum | Desulfovibrio D168 | Elizabethkingia meningoseptica |
| Escherichia coli | Lactobacillus reuteri | Mucispirillum schaedleri |
| Oxalobacter formigenes | Parabacteroides distasonis | Peptostreptococcus anaerobius |
| Prevotella melaninogenica | Prevotella stercorea | Pseudomonas spp. |
| Pyramidobacter piscolens | Rothia mucilaginosa | Streptococcus anginosus |
| Veillonella dispar | | |

In certain embodiments, the method comprises administering to the subject one or more of the following (i) a probiotic and/or a prebiotic composition that stimulates growth and/or activity of one or more strains of bacteria from one or more genera selected from *Bifidobacterium, Faecalibacterium, Propionibacterium, Pseudoxanthomonas, Streptomyces, Saccharopolyspora* in the pancreatic microbiota of the subject; (ii) a probiotic and/or a prebiotic composition that stimulates growth and/or activity of one or more strains of bacteria from one or more genera selected from *Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus,* Tenericutes ML615J-28, and *Ureaplasma* in the gastrointestinal (GI) microbiota of the subject; (iii) a probiotic and/or a prebiotic composition that stimulates growth and/or activity of one or more strains of bacteria from one or more species selected from *Bifidobac-*

*terium pseudolongum, Faecalibacterium prausnitzii, Bacillus clausii,* and *Propionibacterium acnes* in the pancreatic microbiota of the subject; (iv) a probiotic and/or a prebiotic composition that stimulates growth and/or activity of one or more strains of bacteria from one or more species selected from *Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus,* and TM7 in the gastrointestinal (GI) microbiota of the subject; (v) a probiotic composition comprising one or more strains of bacteria from one or more genera selected from *Bifidobacterium, Faecalibacterium, Propionibacterium, Pseudoxanthomonas, Streptomyces, Saccharopolyspora, Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus,* Tenericutes ML615J-28, and *Ureaplasma*; (vi) a probiotic composition comprising one or more strains of bacteria from one or more species selected from *Bifidobacterium pseudolongum, Faecalibacterium prausnitzii,* and *Propionibacterium acnes, Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus, Bacillus clausii,* and TM7; (vii) a compound or composition which inhibits growth and/or activity of one or more strains of bacteria from one or more genera selected from *Bacteroides, Bifidobacterium, Chryseobacterium, Delftia, Elizabethkingia, Lactobacillus, Mucispirillum, Pseudomonas, Streptococcus, Fusobacterium,* and *Viellonella* in the pancreatic microbiota of the subject; (viii) a compound or composition which inhibits growth and/or activity of one or more strains of bacteria from one or more genera selected from *Akkermansia, Bacteroides, Bifidobacterium, Desulfovibrio, Elizabethkingia, Escherichia, Lactobacillus, Mucispirillum, Oxalobacter, Parabacteroides, Peptostreptococcus, Prevotella, Pyramidobacter, Rothia, Streptococcus,* and *Viellonella* in the gastrointestinal (GI) microbiota of the subject; (ix) a compound or composition which inhibits growth and/or activity of one or more strains of bacteria from one or more species selected from *Bacteroides acidifaciens, Bifidobacterium pseudolongum, Elizabethkingia meningoseptica, Lactobacillus reuteri, Mucispirillum schaedleri, Streptococcus anginosus, Porphyromonas gingivalis, Streptococcus mitis, Neisseria elongata, Helicobacter pylori,* and *Veillonella dispar* in the pancreatic microbiota of the subject; or (x) a compound or composition which inhibits growth and/or activity of one or more strains of bacteria from one or more species selected from *Akkermansia muciniphila, Bacteroides acidifaciens, Bifidobacterium animalis, Bifidobacterium pseudolongum, Desulfovibrio* D168, *Elizabethkingia meningoseptica, Escherichia coli, Lactobacillus reuteri, Mucispirillium schaedleri, Oxalobacter formigenes, Parabacteroides distasoni, Peptostreptococcus anaerobius, Prevotella melaninogenica, Prevotella stercorea, Pyramidobacter piscolens, Rothia mucilaginosa, Streptococcus anginosus,* and *Veillonella dispar* in the gastrointestinal (GI) microbiota of the subject.

In one embodiment of any of the above methods, the method further comprises monitoring the subject's pancreatic and/or gastrointestinal microbiota after the administration of the compound or composition by: (a) determining the level of at least one strain of fungi from the genus *Malassezia* in the pancreatic and/or gastrointestinal microbiota of the subject, and (b) comparing the level determined in step (a) to the level of the same fungi in the control pancreatic and/or gastrointestinal microbiota. In certain embodiments, the method comprises determining the level of at least one strain of fungi from the species *Malassezia globosa*. In certain embodiments, the control microbiota is microbiota of age- and/or sex, and/or ethnicity matched healthy subjects.

Non-limiting examples of the methods which can be used for determining the level of fungi include, e.g., quantitative PCR (qPCR), high-throughput sequencing, transcriptomic analysis, bacterial genotype pattern based fingerprinting (DNA fingerprinting), and proteomic analysis.

Pharmaceutical Compositions, Formulations and Combination Treatments

In one aspect, the present disclosure provides a pharmaceutical composition comprising (i) a compound or composition which can inhibit growth and/or activity of one or more strains of fungi from the genus *Malassezia* in the pancreatic and/or gastrointestinal microbiota of a subject, and (ii) a chemotherapeutic and/or immunotherapeutic agent. In certain embodiments, the compound or composition can inhibit growth and/or activity of one or more strains of fungi from the species *Malassezia globosa*.

In one aspect, the present disclosure provides a pharmaceutical dosage form comprising (i) a compound or composition which can inhibit growth and/or activity of one or more strains of fungi from the genus *Malassezia* in the pancreatic and/or gastrointestinal microbiota of a subject, and (ii) a chemotherapeutic and/or immunotherapeutic agent. In certain embodiments, the compound or composition can inhibit growth and/or activity of one or more strains of fungi from the species *Malassezia globosa*.

In certain embodiments of the pharmaceutical composition or pharmaceutical dosage form, the compound or composition that inhibits growth and/or activity of one or more strains of fungi from the genus *Malassezia* in the pancreatic and/or gastrointestinal microbiota comprises an antifungal compound or a natural product that inhibits fungal growth. The antifungal compound may be selected from an echocandin compound, a triazole compound, and a polyene compound, and any combinations thereof. In certain embodiments, the antifungal compound is amphotericin B or fluconazole.

In certain embodiments, the pharmaceutical composition or pharmaceutical dosage form further comprises a small molecule inhibitor or an antibody that inhibits the function of mannose-binding lectin (MBL)-C3 convertase complement axis. In certain embodiments, the small molecule inhibitor or an antibody is selected from APL-2, compstatin Cp40, POT-4 and/or MAb 3F8 and/or hMBL 1.2, and any combinations thereof.

In certain embodiments, the pharmaceutical composition or pharmaceutical dosage form further comprises a second compound or composition that stimulates growth and/or activity of one or more strains of fungi from the genera *Saccharomyces* and *Candida* in the pancreatic and/or gastrointestinal microbiota of the subject. In certain embodiments, the composition comprises one or more strains of fungi from the genera *Saccharomyces* and *Candida*.

In certain embodiments, the pharmaceutical composition or pharmaceutical dosage form further comprises one or more of the following (i) a probiotic and/or a prebiotic composition that stimulates growth and/or activity of one or more strains of bacteria from one or more genera selected from *Bifidobacterium*, *Faecalibacterium*, *Propionibacterium*, *Pseudoxanthomonas*, *Streptomyces*, *Saccharopolyspora* in the pancreatic microbiota of the subject; (ii) a probiotic and/or a prebiotic composition that stimulates growth and/or activity of one or more strains of bacteria from one or more genera selected from *Akkermansia*, *Bacteroides*, *Bifidobacterium*, *Blautia*, *Brachyspira*, *Candidatus arthromitus*, *Dorea*, *Eubacterium*, *Faecalibacterium*, *Gallicola*, *Lactobacillus*, *Megamonas*, *Mollicutes* RF39, *Mycoplasma*, *Parabacteroides*, *Prevotella*, *Ruminococcus*, Tenericutes ML615J-28, and *Ureaplasma* in the gastrointestinal (GI) microbiota of the subject; (iii) a probiotic and/or a prebiotic composition that stimulates growth and/or activity of one or more strains of bacteria from one or more species selected from *Bifidobacterium pseudolongum*, *Faecalibacterium prausnitzii*, *Bacillus clausii*, and *Propionibacterium acnes* in the pancreatic microbiota of the subject; (iv) a probiotic and/or a prebiotic composition that stimulates growth and/or activity of one or more strains of bacteria from one or more species selected from *Akkermansia muciniphila*, *Bacteroides eggerthii*, *Bacteroides fragilis*, *Bifidobacterium adolescentis*, *Blautia producta*, *Candidatus Arthromitus*, *Eubacterium* biforme, *Faecalibacterium prausnitzii*, *Lactobacillus reuteri*, *Lactobacillus* ruminis, *Parabacteroides distasonis*, *Prevotella copri*, *Ruminococcus gnavus*, and TM7 in the gastrointestinal (GI) microbiota of the subject; (v) a probiotic composition comprising one or more strains of bacteria from one or more genera selected from *Bifidobacterium*, *Faecalibacterium*, *Propionibacterium*, *Pseudoxanthomonas*, *Streptomyces*, *Saccharopolyspora*, *Akkermansia*, *Bacteroides*, *Bifidobacterium*, *Blautia*, *Brachyspira*, *Candidatus arthromitus*, *Dorea*, *Eubacterium*, *Faecalibacterium*, *Gallicola*, *Lactobacillus*, *Megamonas*, *Mollicutes* RF39, *Mycoplasma*, *Parabacteroides*, *Prevotella*, *Ruminococcus*, Tenericutes ML615J-28, and *Ureaplasma*; (vi) a probiotic composition comprising one or more strains of bacteria from one or more species selected from *Bifidobacterium pseudolongum*, *Faecalibacterium prausnitzii*, and *Propionibacterium acnes*, *Akkermansia muciniphila*, *Bacteroides eggerthii*, *Bacteroides fragilis*, *Bifidobacterium adolescentis*, *Blautia producta*, *Candidatus Arthromitus*, *Eubacterium* biforme, *Faecalibacterium prausnitzii*, *Lactobacillus reuteri*, *Lactobacillus ruminis*, *Parabacteroides distasonis*, *Prevotella copri*, *Ruminococcus gnavus*, *Bacillus clausii*, and TM7; (vii) a compound or composition which inhibits growth and/or activity of one or more strains of bacteria from one or more genera selected from *Bacteroides*, *Bifidobacterium*, *Chryseobacterium*, *Delftia*, *Elizabethkingia*, *Lactobacillus*, *Mucispirillum*, *Pseudomonas*, *Streptococcus*, *Fusobacterium*, and *Viellonella* in the pancreatic microbiota of the subject; (viii) a compound or composition which inhibits growth and/or activity of one or more strains of bacteria from one or more genera selected from *Akkermansia*, *Bacteroides*, *Bifidobacterium*, *Desulfovibrio*, *Elizabethkingia*, *Escherichia*, *Lactobacillus*, *Mucispirillum*, *Oxalobacter*, *Parabacteroides*, *Peptostreptococcus*, *Prevotella*, *Pyramidobacter*, *Rothia*, *Streptococcus*, and *Viellonella* in the gastrointestinal (GI) microbiota of the subject; (ix) a compound or composition which inhibits growth and/or activity of one or more strains of bacteria from one or more species selected from *Bacteroides acidifaciens*, *Bifidobacterium pseudolongum*, *Elizabethkingia meningoseptica*, *Lactobacillus reuteri*, *Mucispirillum* schaedleri, *Streptococcus* anginosus, *Porphyromonas gingivalis*, *Streptococcus mitis*, *Neisseria*

*elongata, Helicobacter pylori*, and *Veillonella dispar* in the pancreatic microbiota of the subject; or (x) a compound or composition which inhibits growth and/or activity of one or more strains of bacteria from one or more species selected from *Akkermansia* muciniphila, *Bacteroides acidifaciens, Bifidobacterium animalis, Bifidobacterium pseudolongum, Desulfovibrio* D168, *Elizabethkingia meningoseptica, Escherichia coli, Lactobacillus reuteri, Mucispirillium schaedleri, Oxalobacter formigenes, Parabacteroides* distasoni, *Peptostreptococcus anaerobius, Prevotella melaninogenica, Prevotella stercorea, Pyramidobacter piscolens, Rothia mucilaginosa, Streptococcus anginosus*, and *Veillonella dispar* in the gastrointestinal (GI) microbiota of the subject.

In certain embodiments, the compound or composition of the invention can be delivered directly to the pancreas. In certain embodiments, administration can be a single, discontinuous administration or continuous administration (i.e., perfusion). In some embodiments, the compound of composition can be introduced into the pancreas in vivo via the duct system. Intraductal administration can be accomplished by cannulation by, for example, insertion of the cannula through a lumen of the gastrointestinal tract, by insertion of the cannula through an external orifice, or insertion of the cannula through the common bile duct. Retrograde ductal administration (i.e., administration into the fluid contents of the duct system of an exocrine gland in a direction opposite to the normal flow of that fluid, e.g., at the external orifice of the duct system or through its wall) may be accomplished in the pancreas by endoscopic retrograde chalangio-pancreatography (ECRP). In certain embodiments, the compound or composition can be administered directly to the pancreas by percutaneously isolating the pancreatic portion of the celiac axis via an endovascular catheter, and then exogenously introducing the compound or composition into the isolated area, via an infusion port of the catheter. In some embodiments, a balloon catheter, a filter basket or element can be used to isolate the proximal and distal end of a pancreatic portion of the splenic artery. The isolated area can then be perfused with the compound or composition via an infusion port disposed between two balloon catheters, filter baskets or elements. In some embodiments, it may be desirable to temporarily isolate the two ends of the pancreatic section of the splenic artery by other mechanisms including, for example, micro-filters configured to prevent passage of materials (e.g., fungi), but enabling passage of other fluids. Exemplary methods for accomplishing delivery to the pancreas are described in U.S. Pat. Nos. 6,004,944 and 8,821,476 and U.S. Pub. No. US20090088676, which are incorporated herein by reference in their entirety for all purposes.

Oral delivery may also include the use of nanoparticles that can be targeted, e.g., to the GI tract and/or pancreas of the subject, such as those described in Yun et al., Adv Drug Deliv Rev. 2013, 65(6):822-832 (e.g., mucoadhesive nanoparticles, negatively charged carboxylate- or sulfate-modified particles, etc.). Non-limiting examples of other methods of targeting delivery of compositions to the GI tract are discussed in U.S. Pat. Appl. Pub. No. 2013/0149339 and references cited therein (e.g., pH sensitive compositions [such as, e.g., enteric polymers which release their contents when the pH becomes alkaline after the enteric polymers pass through the stomach], compositions for delaying the release [e.g., compositions which use hydrogel as a shell or a material which coats the active substance with, e.g., in vivo degradable polymers, gradually hydrolyzable polymers, gradually water-soluble polymers, and/or enzyme degradable polymers], bioadhesive compositions which specifically adhere to the colonic mucosal membrane, compositions into which a protease inhibitor is incorporated, a carrier system being specifically decomposed by an enzyme present in the colon).

For oral administration, the active ingredient(s) can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

It is also contemplated that when used to treat various pancreatic cancers or tumors, the compositions and methods of the present invention can be utilized with other therapeutic methods/agents suitable for the same or similar cancers or tumors. Such other therapeutic methods/agents can be co-administered (simultaneously or sequentially) to generate additive or synergistic effects. Suitable therapeutically effective dosages for each agent may be lowered due to the additive action or synergy.

In one aspect, the present invention provides a method for enhancing efficacy of a treatment for a pancreatic cancer or tumor in a subject in need thereof, said method comprising (i) administering said treatment to the subject and further (ii) administering to the subject an effective amount of a compound or composition, wherein the compound or composition inhibits growth and/or activity of one or more strains of fungi from the genus *Malassezia* in the pancreatic and/or gastrointestinal microbiota of the subject.

In certain embodiments, the compound or composition that inhibit growth and/or activity of one or more strains of fungi and the therapeutic methods/agents can be administered in one composition. In certain embodiments, the compound or composition that inhibit growth and/or activity of one or more strains of fungi and the therapeutic methods/agents can be administered in different compositions.

In one embodiment of any of the above methods of the invention, the method further comprises administering to the subject one or more additional cancer therapy selected from surgery, radiotherapy, chemotherapy, immunotherapy, and any combinations thereof.

In one embodiment of any of the above methods of the invention, the method further comprises administering to the subject one or more additional compounds selected from immuno-suppressives, biologicals, probiotics, prebiotics, and cytokines (e.g., IFN or IL-22), and any combinations thereof.

In certain embodiments, the compositions can be administered with a chemotherapy. In certain embodiments, the compositions can be administered with an effective amount of FOLFIRINOX (folinic acid, 5-fluorouracil, irinotecan, oxaliplatin), gemcitabine, ABRAXANE (protein-bound paclitaxel), capecitabine, 5-fluorouracil, or any combinations thereof.

In certain embodiments, the compositions can be administered with an effective amount of at least one programmed cell death protein 1 (PD-1) inhibitor, programmed death-ligand 1 (PD-L1) inhibitor or cytotoxic T-lymphocyte-associated antigen 4 (CTLA-4) inhibitor. In certain embodiments, co-administration with a PD-1 inhibitor results in synergistic results (e.g., treatment of pancreatic cancer). In certain embodiments, the PD-1 inhibitor is an antibody. In certain embodiments, the PD-1 inhibitor antibody can be pembrolizumab or nivolumab. In certain embodiments, the PD-L1 inhibitor is atezolizumab, avelumab or durvalumab. In certain embodiments, the CTLA-4 inhibitor is ipilimumab.

As a non-limiting example, the invention can be combined with other therapies that block inflammation (e.g., via blockage of IL1, INFα/β, IL6, TNF, IL23, etc.).

The methods and compositions of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The methods of the invention can be also combined with other treatments that possess the ability to modulate NKT function or stability, including but not limited to CD1d, CD1d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e).

Therapeutic methods of the invention can be combined with additional immunotherapies and therapies. For example, when used for treating cancer, the compositions of the invention can be used in combination with conventional cancer therapies, such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the compositions of the invention can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present invention include, for example, ABRAXANE (protein-bound paclitaxel), aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, FOLFIRINOX (folinic acid, 5-fluorouracil, irinotecan, oxaliplatin), gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine. In certain embodiments, the chemotherapeutic can be FOLFIRINOX (folinic acid, 5-fluorouracil, irinotecan, oxaliplatin), gemcitabine, ABRAXANE (protein-bound paclitaxel), or a combination thereof.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and NAVELBINE (vinorelbine), epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, TAXOL (paclitaxel), TAXOTERE (docetaxel), teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

The compositions of the invention can comprise a carrier and/or excipient. While it is possible to use a compound or a composition of the present invention for therapy as is, it may be preferable to administer it in a pharmaceutical formulation, e.g., in admixture with a suitable pharmaceutical excipient and/or carrier selected with regard to the intended route of administration and standard pharmaceutical practice. The excipient and/or carrier must be "acceptable" in the sense of being compatible with the other ingredients of the formulation and not deleterious to the recipient thereof. Acceptable excipients and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient and carrier can be selected with regard to the intended route of administration and standard pharmaceutical practice. Oral formulations readily accommodate additional mixtures, such as, e.g., milk, yogurt, and infant formula. Solid dosage forms for oral administration can also be used and can include, e.g., capsules, tablets, caplets, pills, troches, lozenges, powders, and granules. Non-limiting examples of suitable excipients include, e.g., diluents, buffering agents (e.g., sodium bicarbonate, infant formula, or other agents which allow bacteria to survive and grow [e.g., survive in the acidic environment of the stomach and to grow in the intestinal environment]), preservatives, stabilizers, binders, compaction agents, lubricants, dispersion enhancers, disintegration agents, antioxidants, flavoring agents, sweeteners, and coloring agents. Additional specific examples of suitable carriers and/or excipients include, e.g., vegetable cellulose, vegetable stearic acid, vegetable magnesium stearate, and/or silica. Those of relevant skill in the art are well able to prepare suitable solutions.

Diagnostic Methods of the Invention

In one aspect, the present disclosure provides a method for diagnosing predisposition or determining the likelihood of development of pancreatic cancer or tumor in a subject, said method comprising (a) determining the level of at least one strain of fungi from the genus *Malassezia* in the pancreatic and/or gastrointestinal microbiota of the subject, and (b) comparing the level determined in step (a) to the level of the same fungi in the control pancreatic and/or gastrointestinal microbiota, and (c) identifying that the subject is predisposed to a pancreatic cancer or tumor wherein the level of at least one of the strains measured in step (a) is at least 1000-fold higher than in the control.

In another aspect, the present disclosure provides a method for determining whether a subject diagnosed with pancreatic cancer is at a high risk for cancer progression, said method comprising (a) determining the level of at least one strain of fungi from the genus *Malassezia* in the pancreatic and/or gastrointestinal microbiota of the subject, and (b) comparing the level determined in step (a) to the level of the same fungi in the control pancreatic and/or gastrointestinal microbiota, and (c) identifying that the subject is at a high risk for cancer progression, wherein the level of at least one of the strains measured in step (a) is at least 1000-fold higher than in the control.

In certain embodiments, the pancreatic cancer is pancreatic ductal adenocarcinoma (PDA).

In certain embodiments, the method comprises determining the level of at least one strain of fungi from the species *Malassezia globosa.*

In certain embodiments, the control microbiota is microbiota of age- and/or sex- and/or ethnicity-matched healthy subjects. In certain embodiments, the subject has a functional mannose-binding lectin (MBL)-C3 convertase complement axis.

In certain embodiments, rather than comparing with a healthy subject, the fungi level is compared to an earlier sample taken from the same subject. The sample could be taken before or after treatment. The sample could be taken before or after symptoms of a disease or cancer.

Non-limiting examples of the methods which can be used for determining the level of the fungi strains include, e.g., quantitative PCR (qPCR), high-throughput sequencing, transcriptomic analysis, bacterial genotype pattern based fingerprinting (DNA fingerprinting), and proteomic analysis.

In certain embodiments of any of the diagnostic methods described herein, the method further comprises determining the level of at least one strain of bacteria selected from the taxa listed in Table 1 or Table 2. Methods of determining the level of at least one strain of bacteria include those known in the art, for example, as described in International Application PCT/US18/17052, which is incorporated herein by reference in its entirety for all purposes.

In certain embodiments, diagnostic methods further comprise (a) determining the level of at least one strain of bacteria from one or more genera selected from *Bifidobacterium, Faecalibacterium, Propionibacterium, Pseudoxanthomonas, Streptomyces, Saccharopolyspora* in the pancreatic microbiota or from one or more species selected from *Bifidobacterium pseudolongum, Faecalibacterium prausnitzii, Bacillus clausii*, and *Propionibacterium acnes* or a closely related OTU within the same genus which has at least 90% sequence identity to 16S rRNA of said species over its entire length or has at least 90% sequence identity to any single V region of 16S rRNA of said species in the pancreatic microbiota of the subject, and (b) comparing the level determined in step (a) to the level of the same bacteria in the pancreatic microbiota of healthy controls, and (c) identifying that the subject is predisposed to a pancreatic cancer or tumor wherein the level of at least one of the strains measured in step (a) is at least 35% lower than in healthy controls. In certain embodiments, diagnostic methods further comprise (a) determining the level of at least one strain of bacteria from one or more genera selected from *Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus,* Tenericutes ML615J-28, and *Ureaplasma* or one or more species selected from *Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis,*

*Parabacteroides distasonis, Prevotella copri, Ruminococcus gnavus*, and TM7 or a closely related OTU within the same genus which has at least 90% sequence identity to 16S rRNA of said species over its entire length or has at least 90% sequence identity to any single V region of 16S rRNA of said species in the gastrointestinal (GI) microbiota of the subject, and (b) comparing the level determined in step (a) to the level of the same bacteria in the gastrointestinal (GI) microbiota of healthy controls, and (c) identifying that the subject is predisposed to a pancreatic cancer or tumor wherein the level of at least one of the strains measured in step (a) is at least 35% lower than in healthy controls. In certain embodiments, in step (c) the subject is identified as predisposed to a pancreatic cancer or tumor wherein the level of at least one of the strains measured in step (a) is at least 50% lower than in healthy controls.

In certain embodiments, diagnostic methods further comprise (d) determining the level of at least one strain of bacteria from one or more genera selected from *Bacteroides, Bifidobacterium, Chryseobacterium, Delftia, Elizabethkingia, Lactobacillus, Mucispirillum, Pseudomonas, Streptococcus, Fusobacterium*, and *Viellonella* or from one or more species selected from *Bacteroides acidifaciens, Bifidobacterium pseudolongum, Elizabethkingia meningoseptica, Lactobacillus reuteri, Mucispirillum schaedleri, Streptococcus anginosus, Porphyromonas* gingiva/is, *Streptococcus mitis, Neisseria elongata, Helicobacter pylori*, and *Veillonella dispar* or a closely related OTU within the same genus which has at least 90% sequence identity to 16S rRNA of said species over its entire length or has at least 90% sequence identity to any single V region of 16S rRNA of said species in the pancreatic microbiota of the subject, and (e) comparing the level determined in step (d) to the level of the same bacteria in the pancreatic microbiota of healthy controls, and (f) identifying that the subject is predisposed to a pancreatic cancer or tumor wherein the level of at least one of the strains measured in step (d) is at least 35% higher than in healthy controls. In certain embodiments, diagnostic methods further comprise (d) determining the level of at least one strain of bacteria from one or more genera selected from *Akkermansia, Bacteroides, Bifidobacterium, Desulfovibrio, Elizabethkingia, Escherichia, Lactobacillus, Mucispirillum, Oxalobacter, Parabacteroides, Peptostreptococcus, Prevotella, Pyramidobacter, Rothia, Streptococcus*, and *Viellonella* or from one or more species selected from *Akkermansia muciniphila, Bacteroides acidifaciens, Bifidobacterium animalis, Bifidobacterium pseudolongum, Desulfovibrio* D168, *Elizabethkingia meningoseptica, Escherichia coli, Lactobacillus reuteri, Mucispirillium schaedleri, Oxalobacter formigenes, Parabacteroides distasoni, Peptostreptococcus anaerobius, Prevotella melaninogenica, Prevotella stercorea, Pyramidobacter piscolens, Rothia mucilaginosa, Streptococcus anginosus*, and *Veillonella dispar* or a closely related OTU within the same genus which has at least 90% sequence identity to 16S rRNA of said species over its entire length or has at least 90% sequence identity to any single V region of 16S rRNA of said species in the gastrointestinal (GI) microbiota of the subject, and (e) comparing the level determined in step (d) to the level of the same bacteria in the gastrointestinal (GI) microbiota of healthy controls, and (f) identifying that the subject is predisposed to a pancreatic cancer or tumor wherein the level of at least one of the strains measured in step (d) is at least 35% higher than in healthy controls. In certain embodiments, in step (f) the subject is identified as predisposed to a pancreatic cancer or tumor wherein the level of at least one of the strains measured in step (d) is at least 50% higher than in healthy controls.

Additional methods include methods of evaluating the microbiome population in a subject or diagnosing an abnormal microbiome development. Methods include monitoring the subject's microbiome after the administration of the compound or composition that inhibit growth and/or activity of one or more strains of fungi by: (a) determining a relative level of one or more strains of fungi in a microbiome sample obtained from the subject, and (b) comparing the relative level(s) determined in step (a) to (i) a predetermined standard value or (ii) to the level(s) of the same taxa or genus in a control subject or (iii) to the average value of level of the same taxa or genus in several control subjects. The subject's sample may be isolated from feces, skin, intestines, intestinal mucosa, oral mucosa, conjunctive mucosa, or nasal mucosa. It may be compared to a control subject.

In certain embodiments of any of the diagnostic methods described above, the method further includes recruiting the subject in a clinical trial.

In certain embodiments of any of the diagnostic methods described above, the method further comprises administering a pancreatic cancer or tumor treatment to the subject. The treatment may comprise any of the treatment methods described above.

In accordance with the present invention there may be numerous tools and techniques within the skill of the art, such as those commonly used in molecular biology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ, each of which is herein incorporated by reference in its entirety for all intended purposes.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Figure 1E:
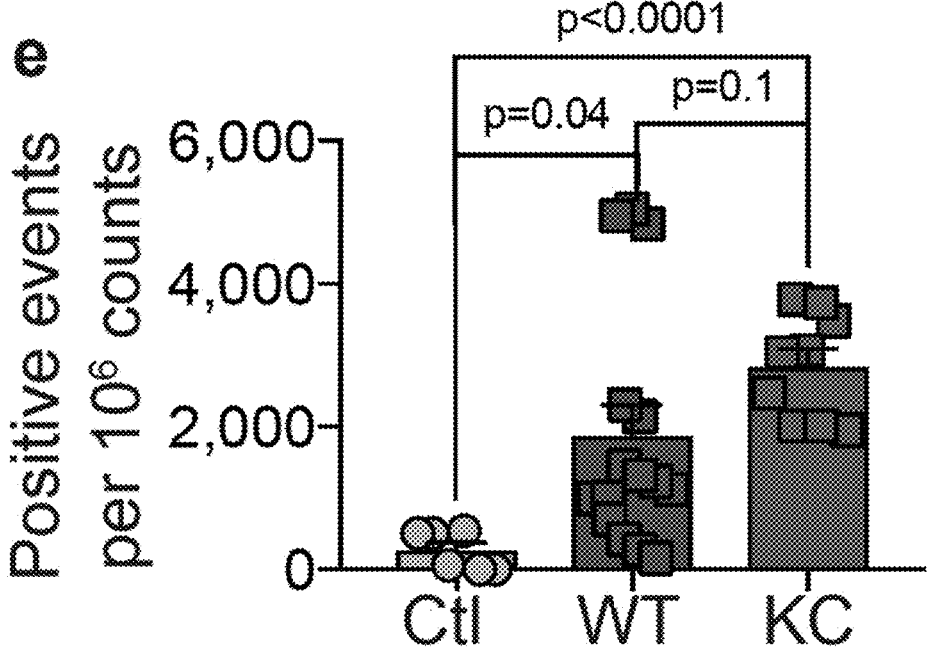

Example 1. Determining the Ability of Bacteria to Access the Pancreas and Affect Pancreatic Oncogenesis In this Example it is shown that there is a marked increase in intratumoral fungi in PDA and in mouse models of this disease (FIGS. 1A-1D). Because there is direct communication between the gut and pancreatic duct via the sphincter of Oddi, it was postulated that endoluminal fungi can access the pancreas. To test this, *Saccharomyces cerevisiae* labeled with GFP was administered to control and tumor-bearing mice via oral gavage. Fungi migrated into the pancreas within 30 min, which suggests that the gut mycobiome can directly influence the pancreatic microenvironment (FIG. 1E).

Figure 1F:
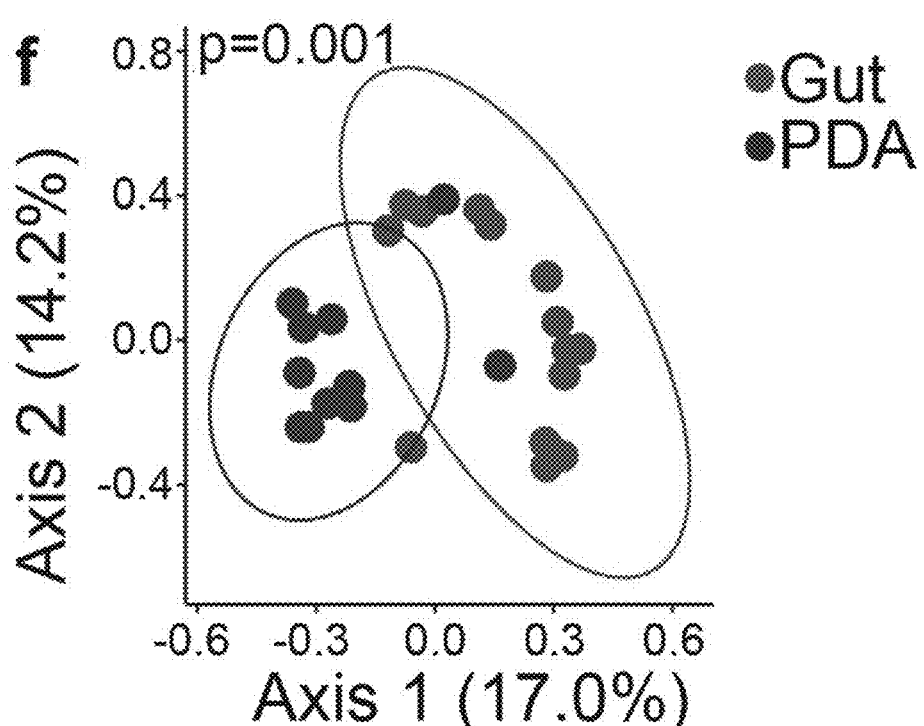
Figure 1G:
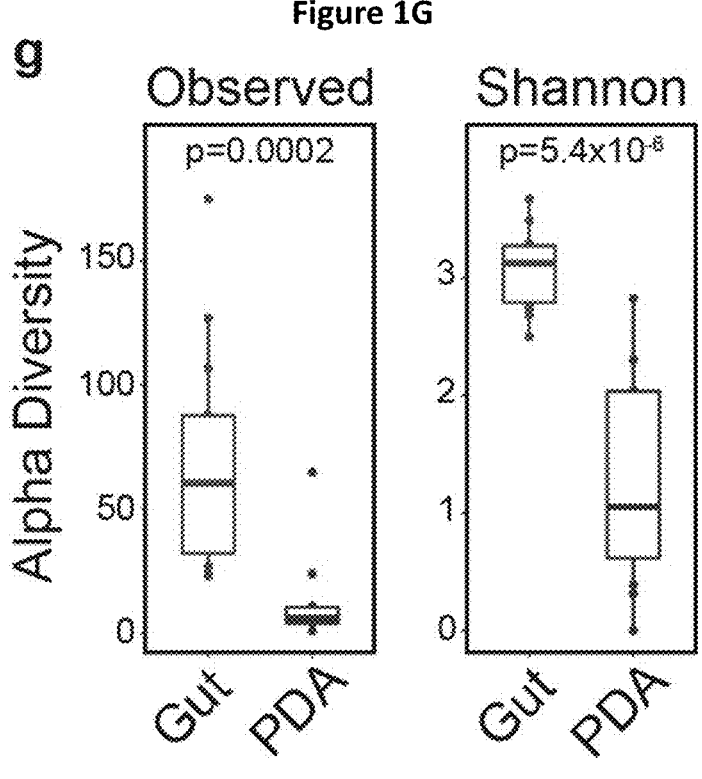
Figure 1H:
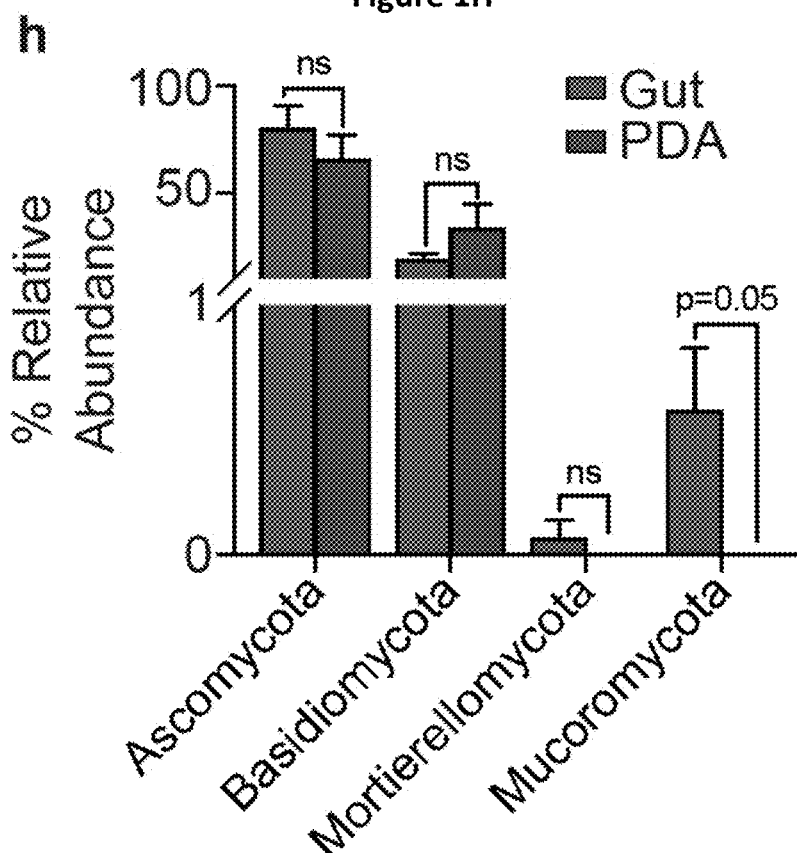
Figure 1I:
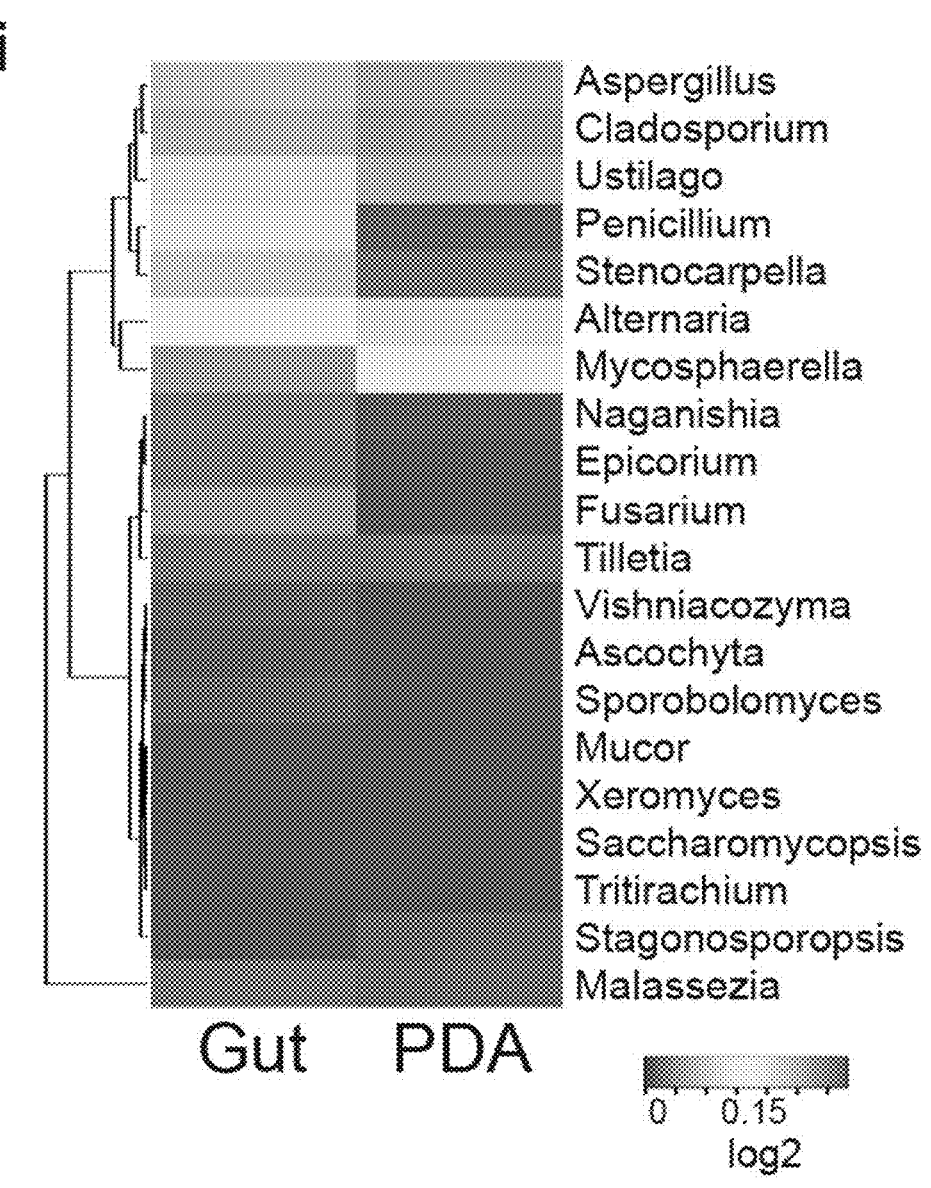
Figure 5:
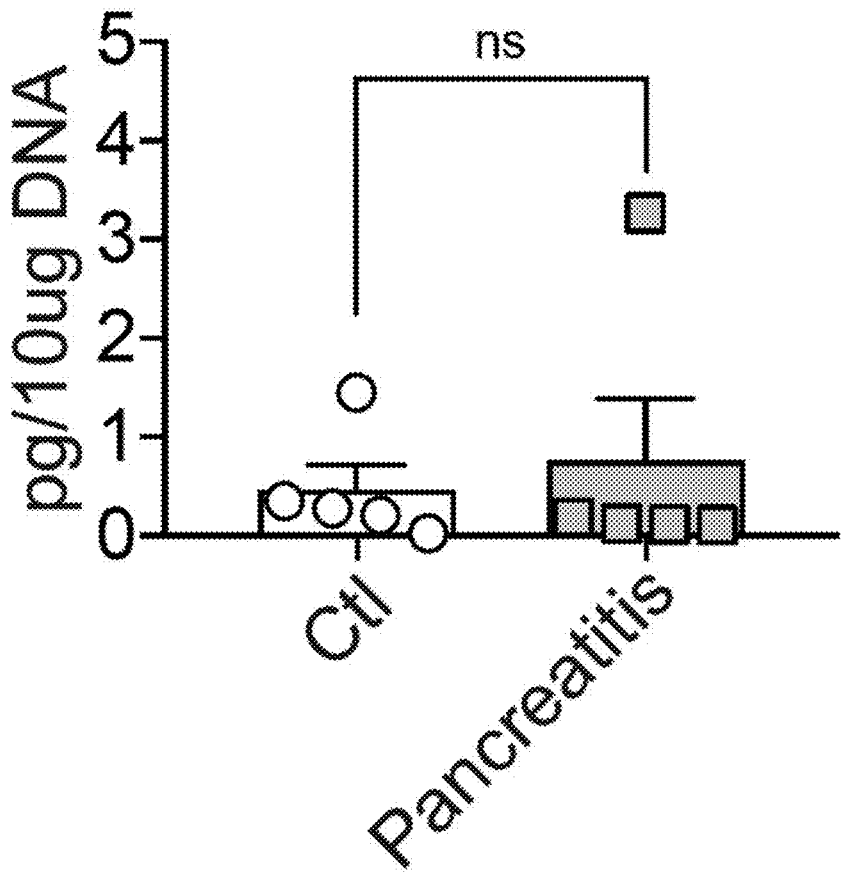
FIG. 5. Fungal infiltration of the pancreas in benign disease. Fungal DNA content was tested using qPCR in pancreata from control (ctl) mice (n=5) and mice induced to develop cerulein-induced pancreatitis (n=5). ns, not significant. Data are mean±s.e.m. Two-tailed Student's t-test.

Next, whether there is evidence of fungal dysbiosis during tumorigenesis was assessed, using p48$^{cre}$;LSL-Kras$^{G12D}$ (p48 is also known as Ptf1a) mice (or KC mice), which express oncogenic Kras in their pancreatic progenitor cells and are a model for the development of slowly progressive PDA[2]. A comparison between the fungal communities of the gut and within the pancreas in 30-week-old KC mice, by principal coordinate analysis (PCoA), suggested that the mycobiomes of the gut and tumors clustered separately (FIG. 1F). Reduced alpha-diversity in the transformed pancreas was also observed compared to in the gut (FIG. 1G). Ascomycota and Basidiomycota were the only phyla that were detected in pancreatic tissue, whereas Mortierellomycota and Mucoromycota were additionally detected in the gut at a low abundance (FIG. 1H). The most-prevalent genus in the pancreata of KC mice was *Malassezia*, at about 20% abundance; this represents a marked increase in relative abundance compared to the presence of this genus in the gut (FIG. 1I). Of note, benign pancreatic inflammation did not increase fungal infiltration into the pancreas (FIG. 5).

Figure 1J:
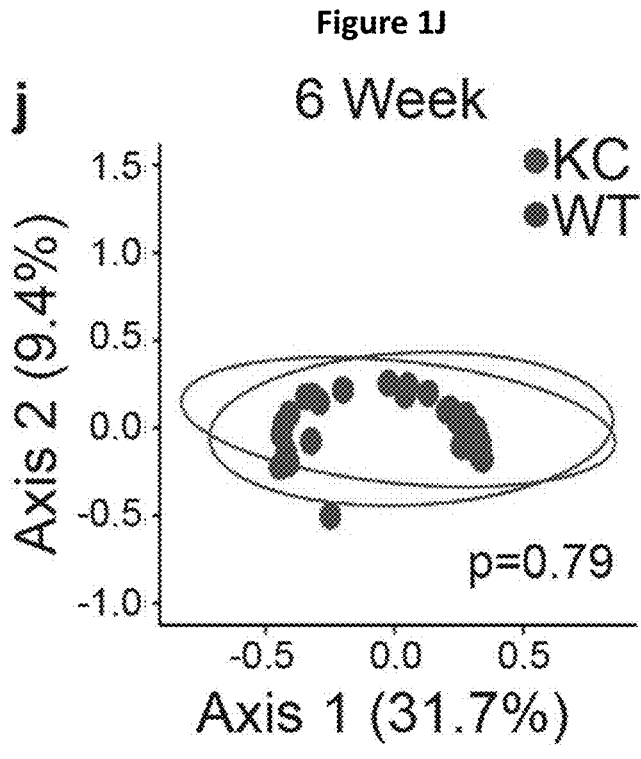
Figure 1K:
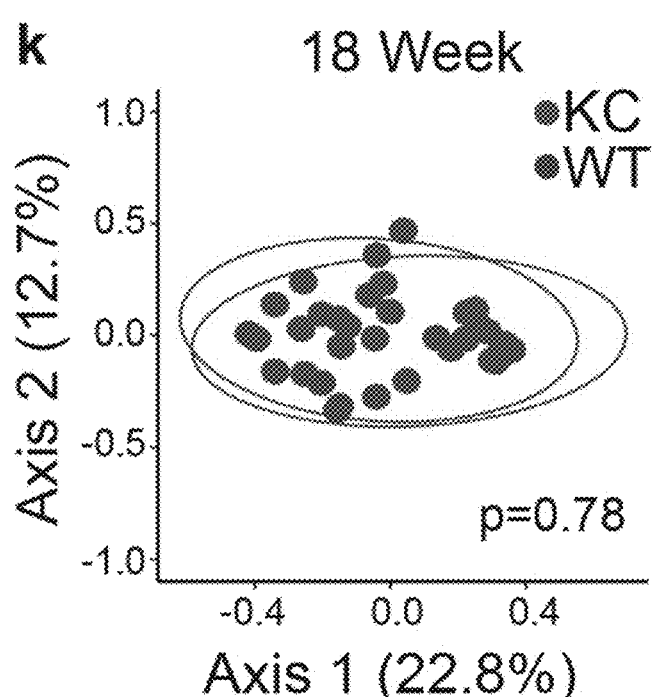
Figure 1L:
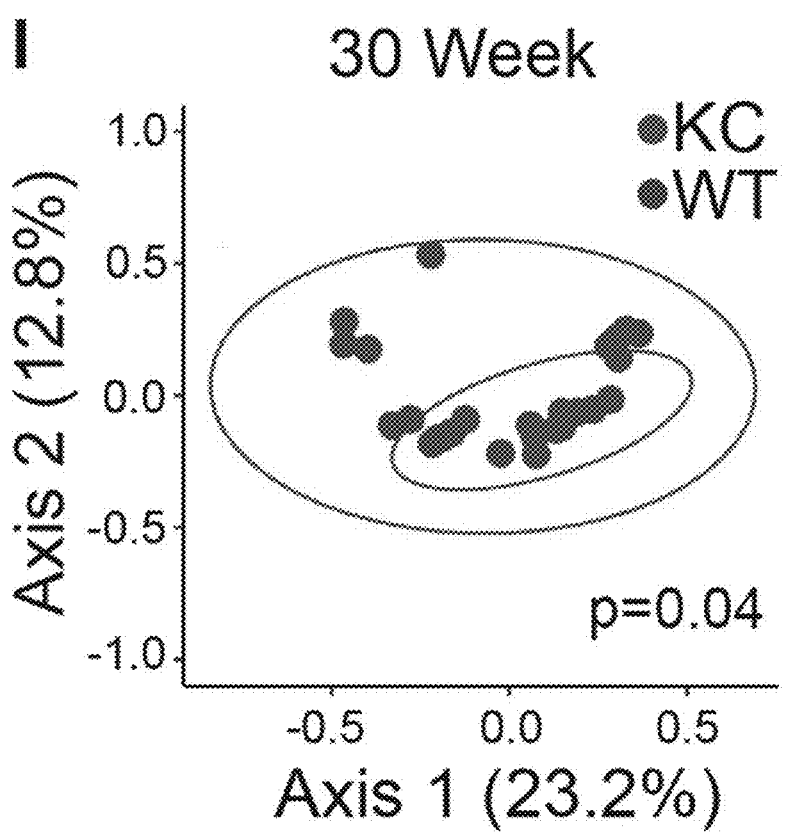
Figure 6:
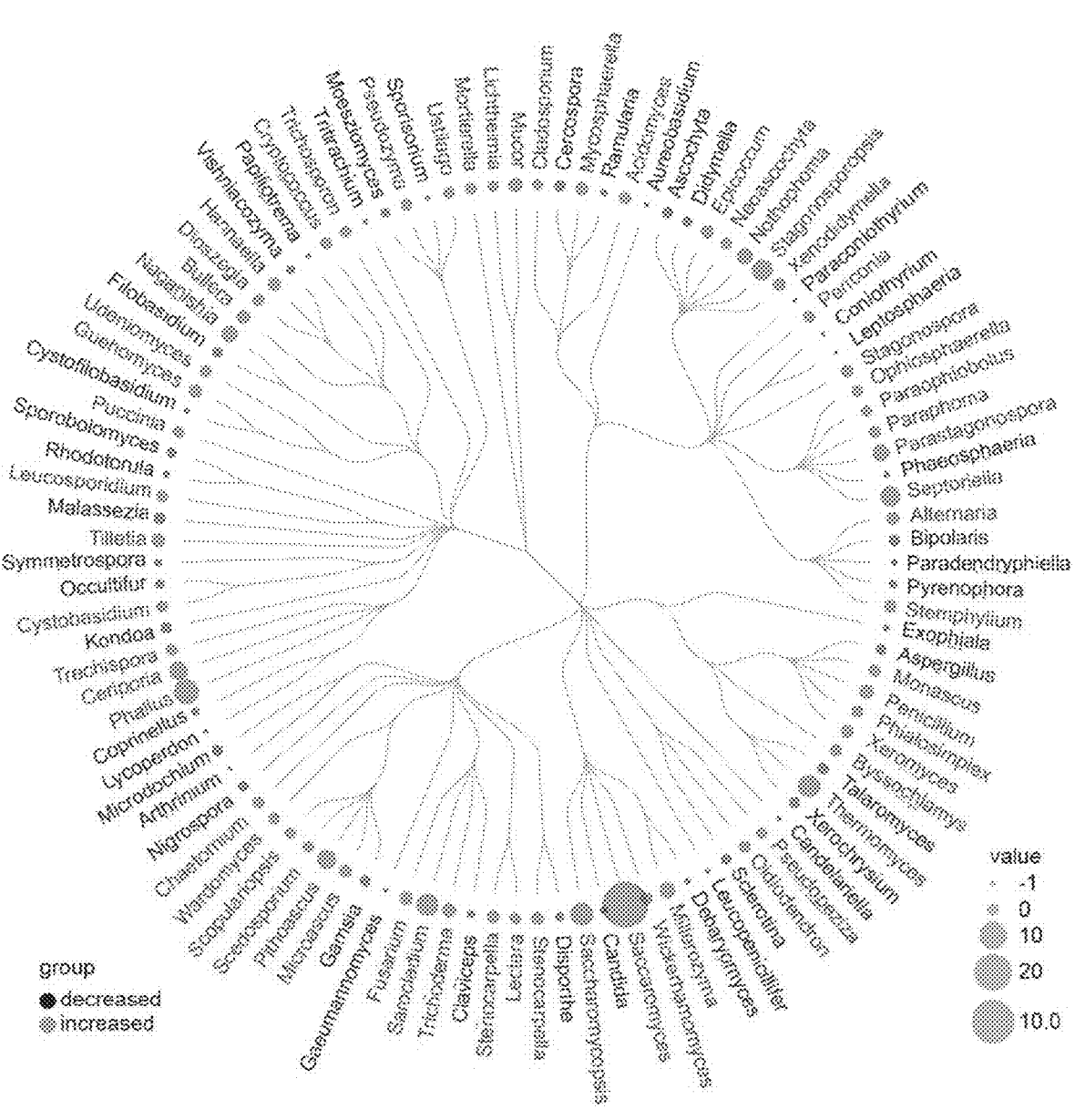
FIG. 6. Dysbiosis of the gut mycobiome in a mouse model of PDA. Hierarchical tree cladogram depicting changes in the taxonomic composition of the mycobiome (assigned to the genus level) in the guts of 30-week-old wild-type (n=12) and KC (n=14) mice, based on the average percent relative abundance of genera as determined by 18S ITS sequencing.

To determine whether the gut mycobiome is reprogrammed during the course of oncogenesis, a longitudinal analysis of fecal samples was performed from KC mice and littermate controls. PCoA suggested that, whereas wild-type and KC mice had similar fungal communities early in life, by 30 weeks of age there were differences in beta-diversity between the gut mycobiomes in the two backgrounds (FIGS. 1J-1L). Accordingly, fungal communities in the gut of KC and wild-type mice differed considerably at 30 weeks (FIG. 6).

Figure 2A:
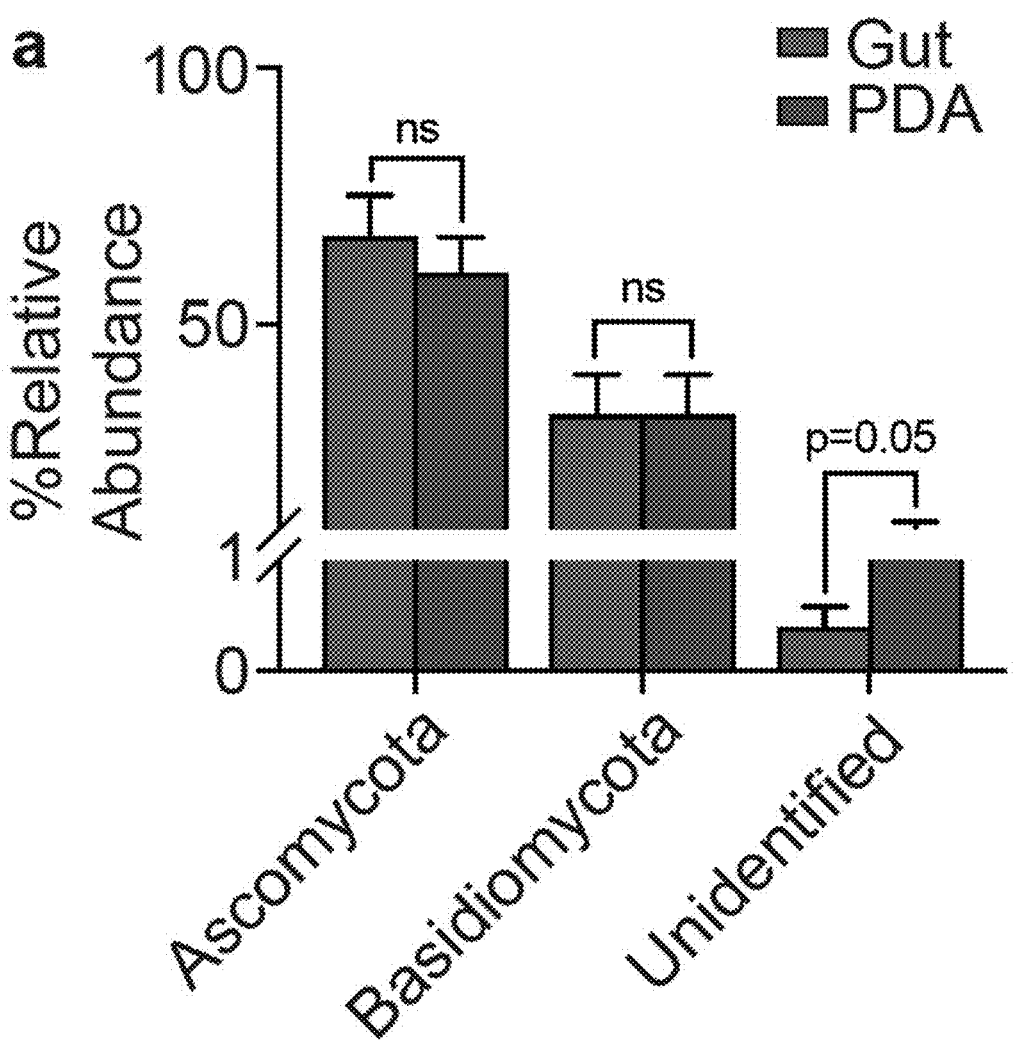
FIGS. 2A-2E. PDA in humans is associated with a distinct mycobiome.
Figure 2B:
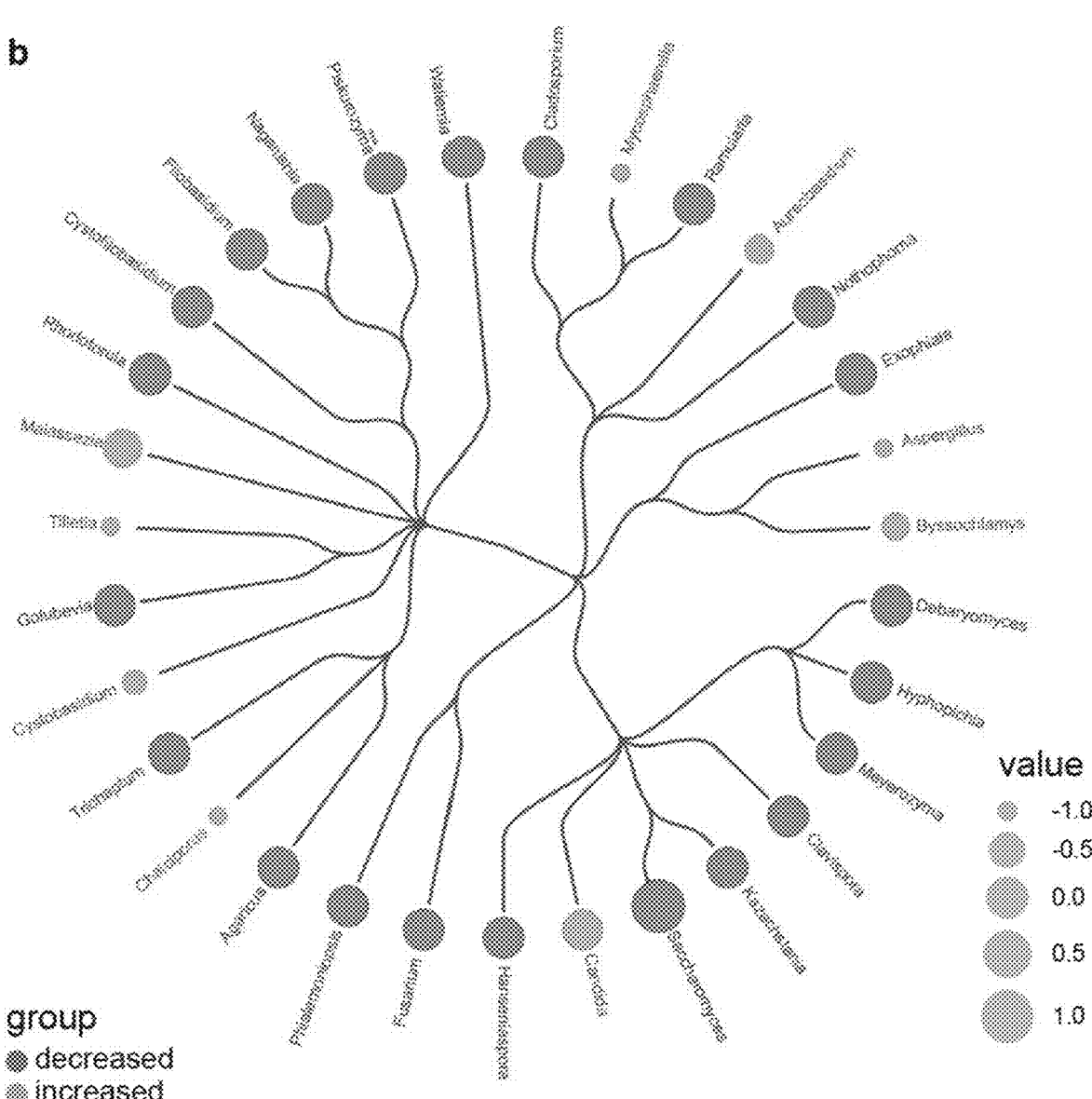
Figure 2C:
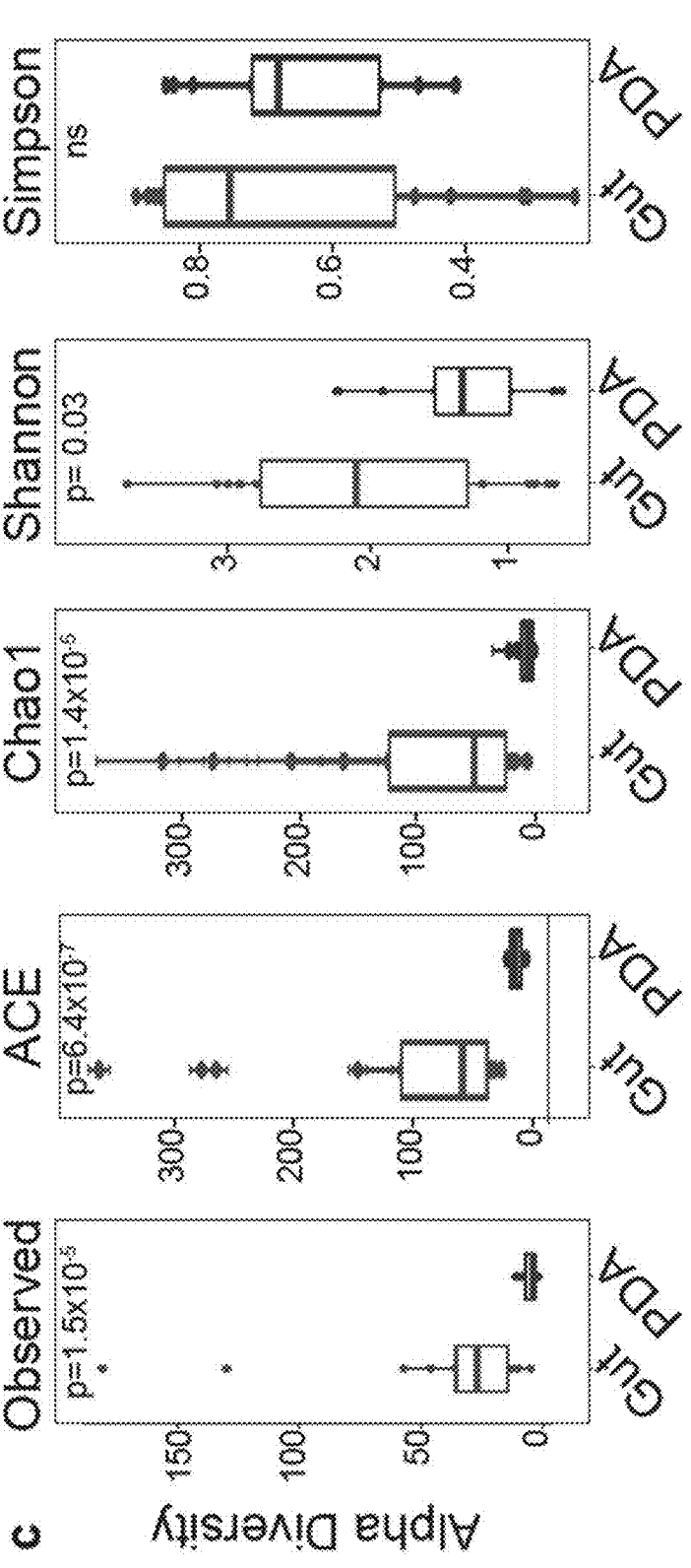
Figure 2D:
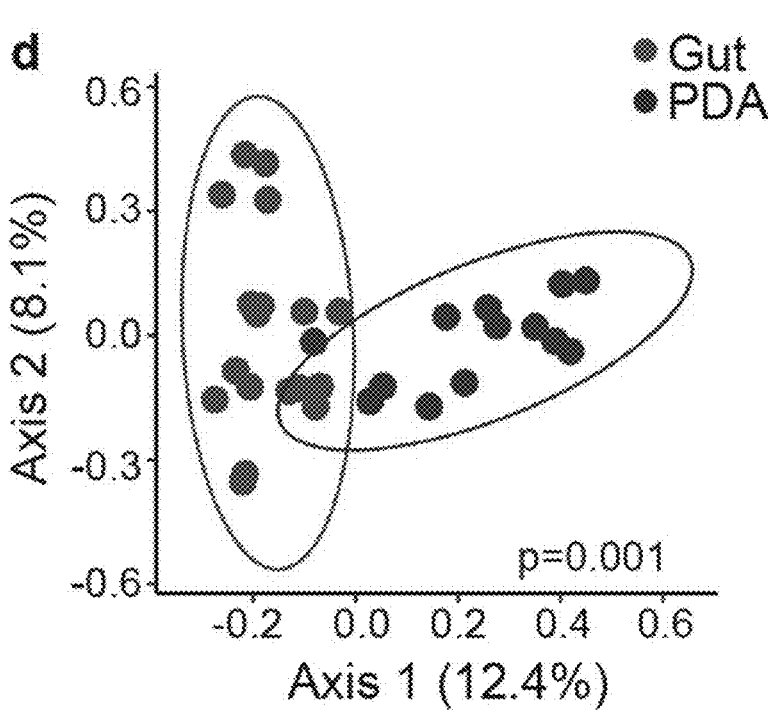
Figure 2E:
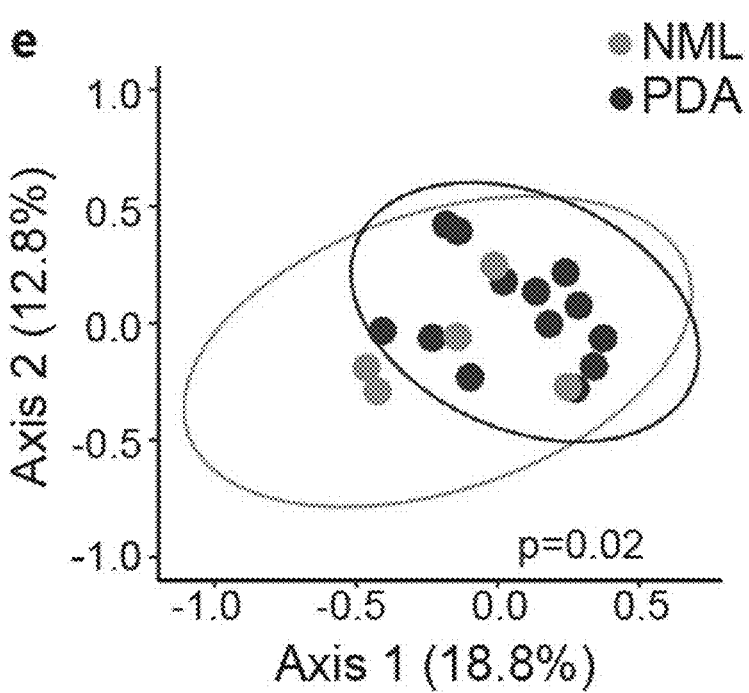

Next, the fecal and tumor mycobiome was analyzed in patients with PDA. As in mice, the Ascomycota and Basidiomycota were the most common phyla in the gut and in tumor tissue of humans (FIG. 2A). At the genus level (and once again parallel to the mice data), *Malassezia* was more prevalent in tumor tissues than in the gut (FIG. 2B). Moreover, alpha-diversity analyses revealed differences between the gut and PDA-tumor tissue in humans (FIG. 2C). PCoA confirmed that there were distinct clusters of fungal communities in the tumor tissue and gut of patients with PDA (FIG. 2D). Furthermore, the mycobiome in pancreata from patients with PDA clustered separately from that in the pancreata of healthy individuals (FIG. 2E). Collectively, these data indicate that the mycobiome of PDA tumors is distinct from that of the gut or healthy pancreas.

Figure 3A:
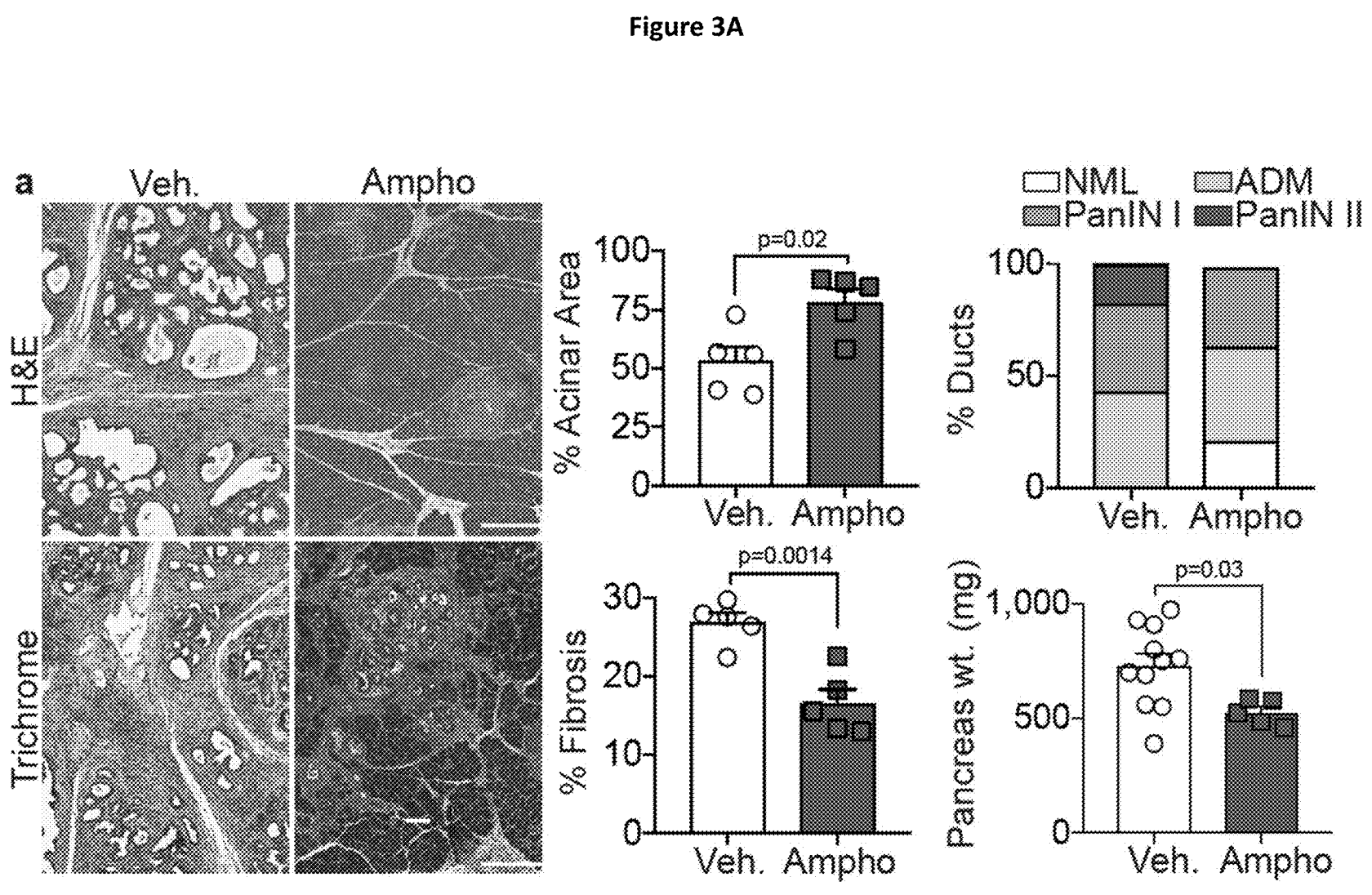
Figure 3B:
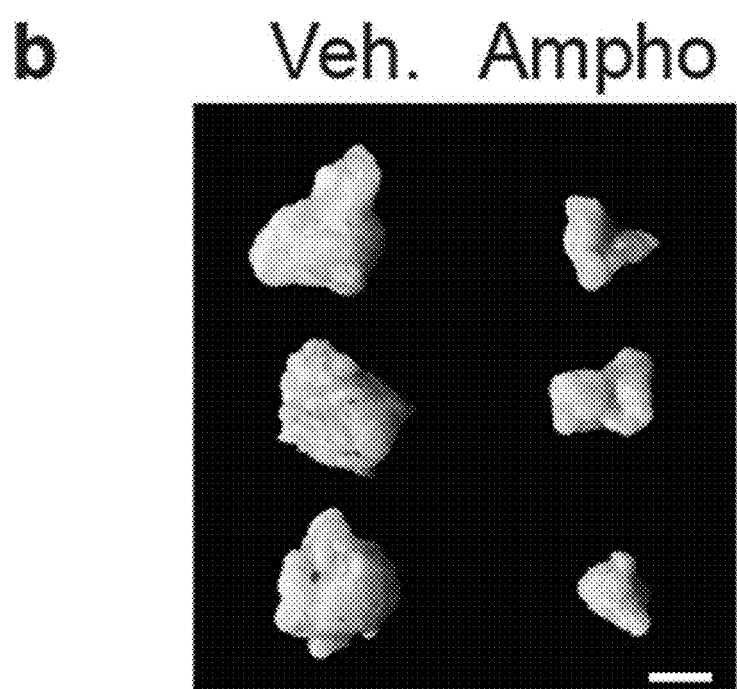
Figure 3B:
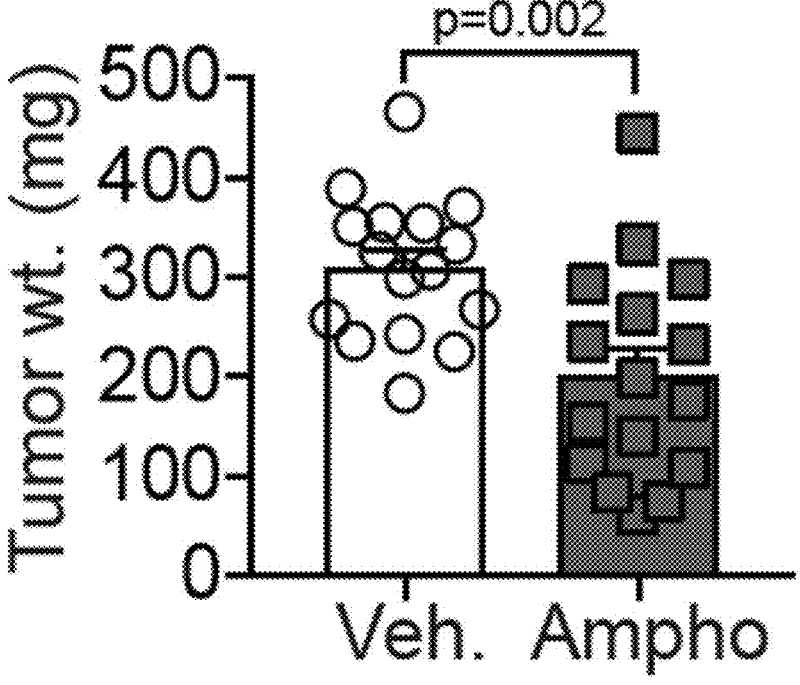
Figure 3C:
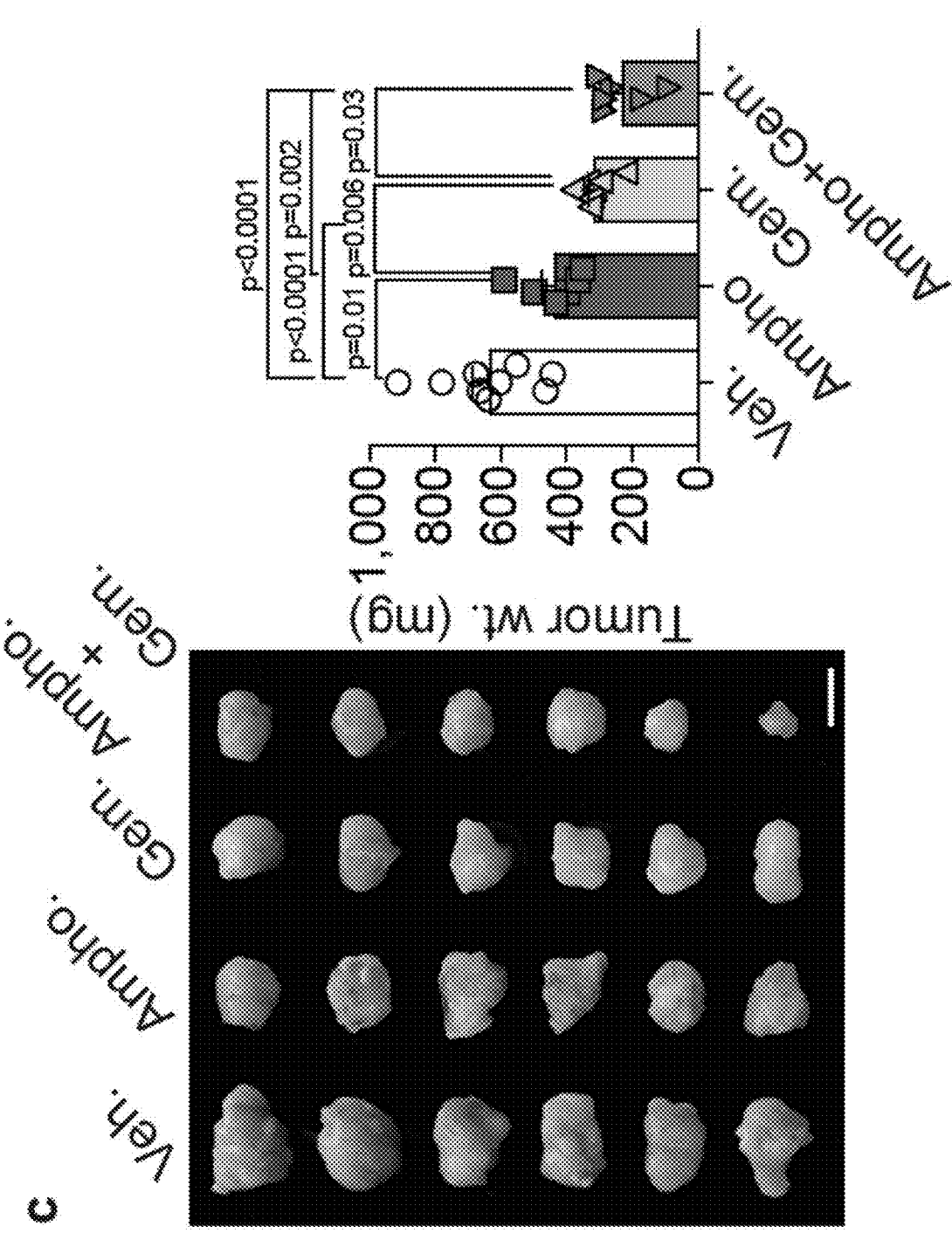
Figure 7A:
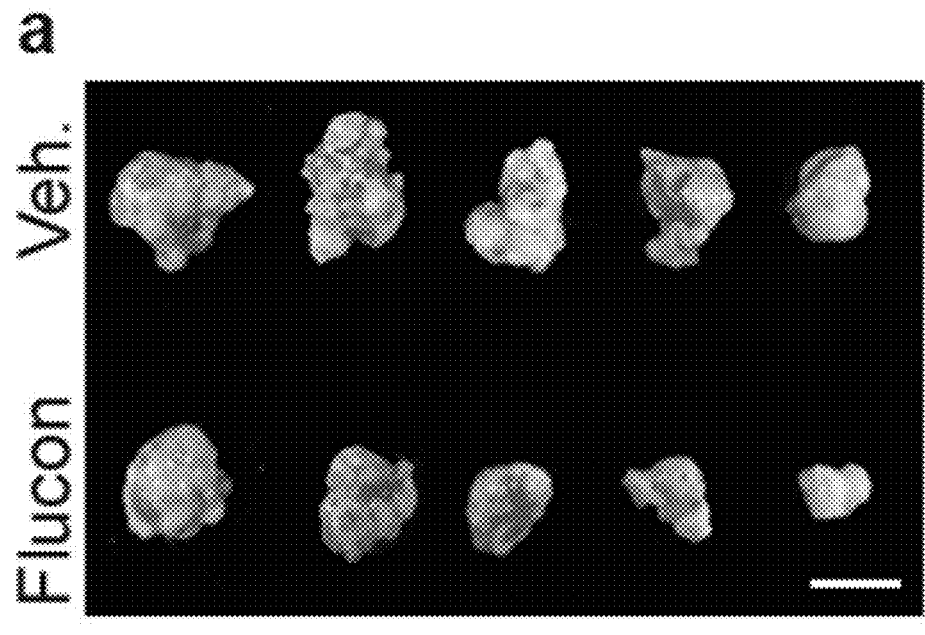
Figure 7A:
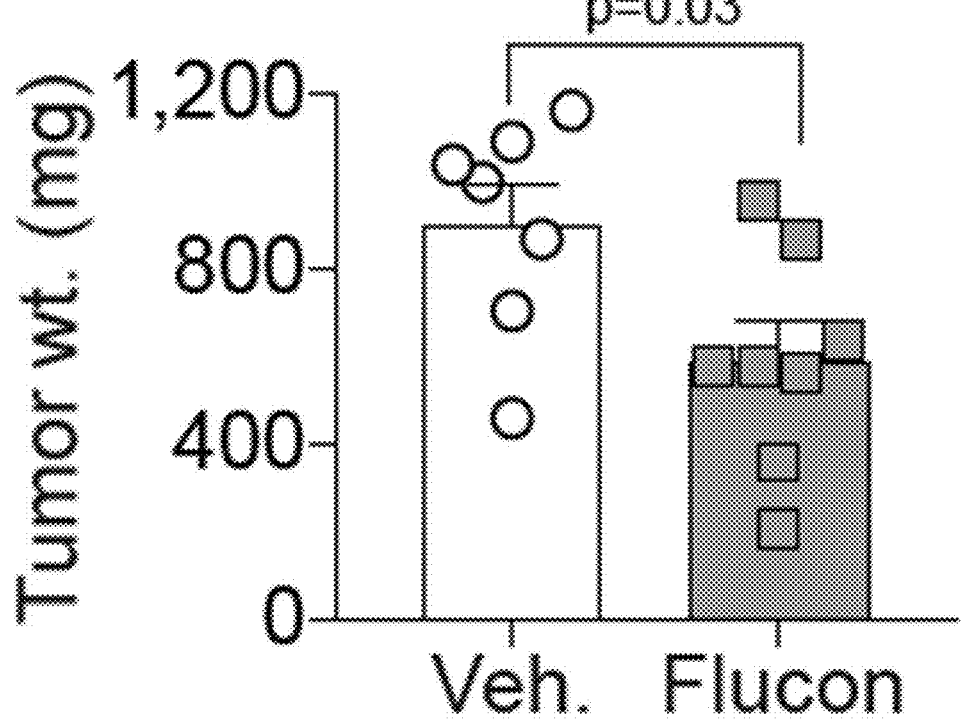
Figure 7B:
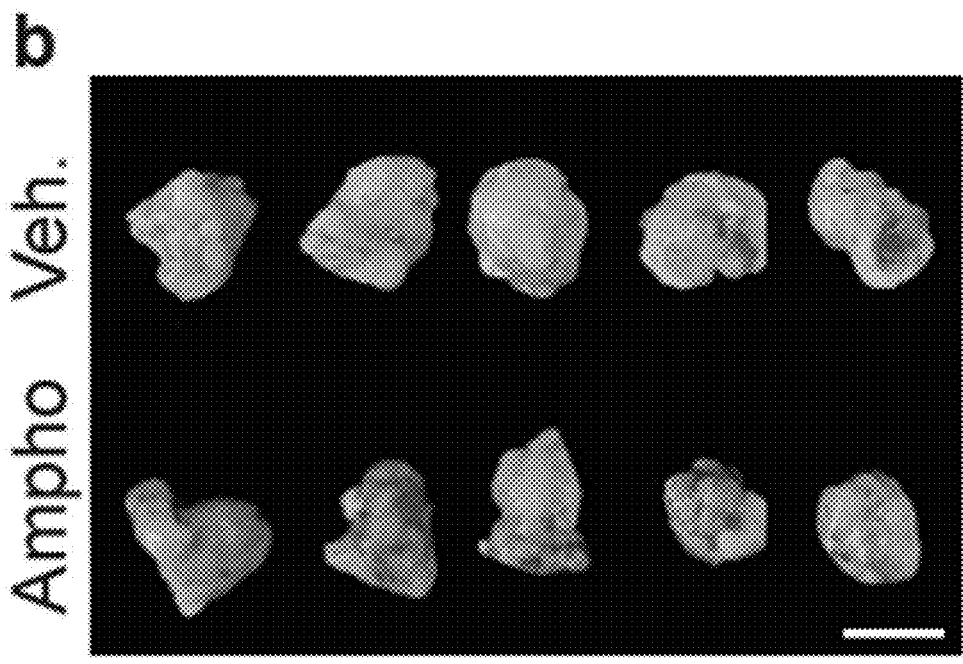
Figure 7B:
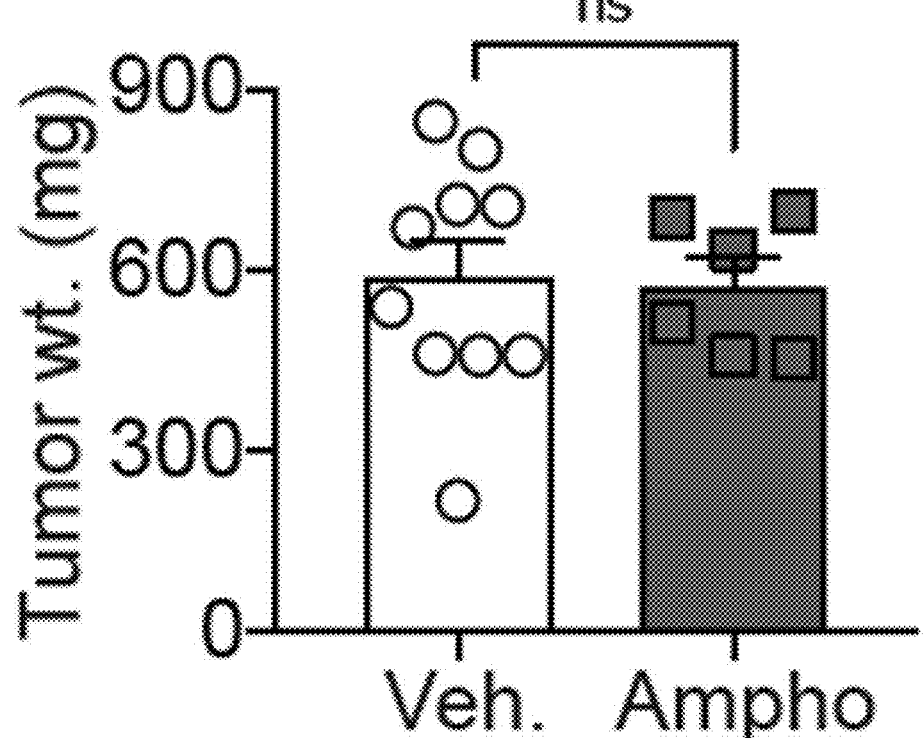
Figure 7C:
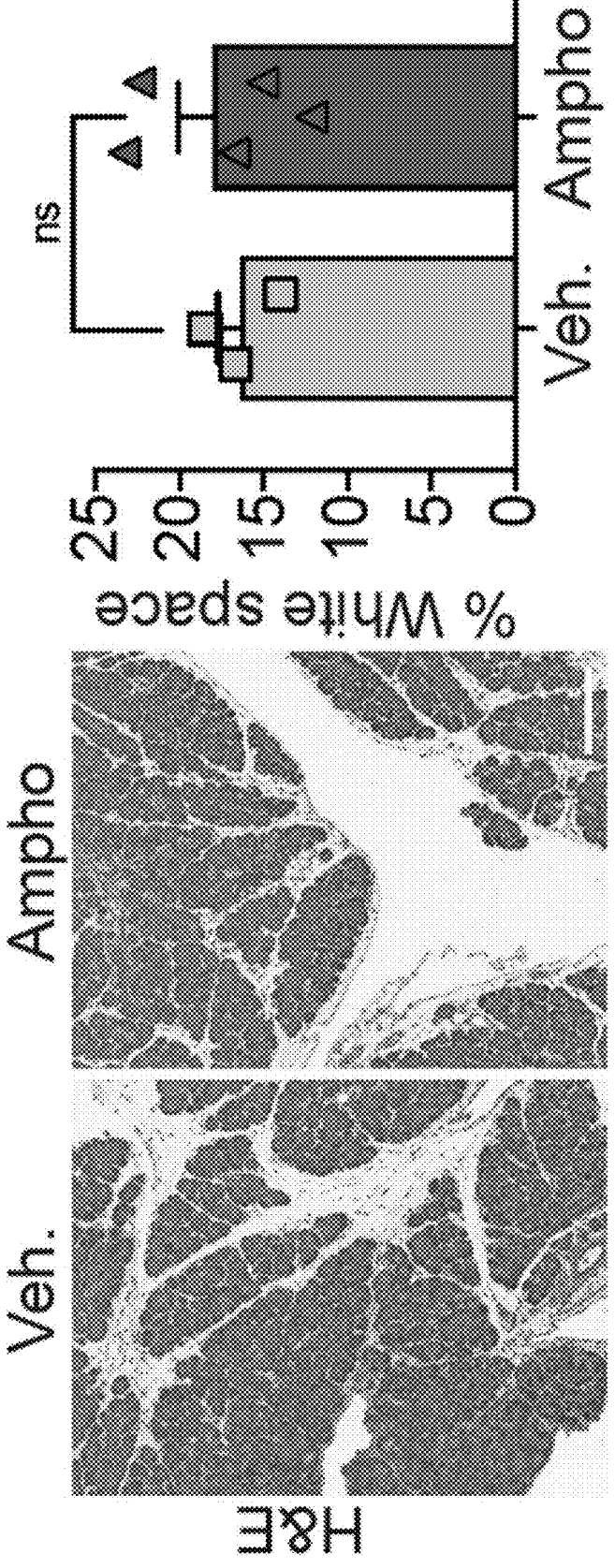
Figure 7D:
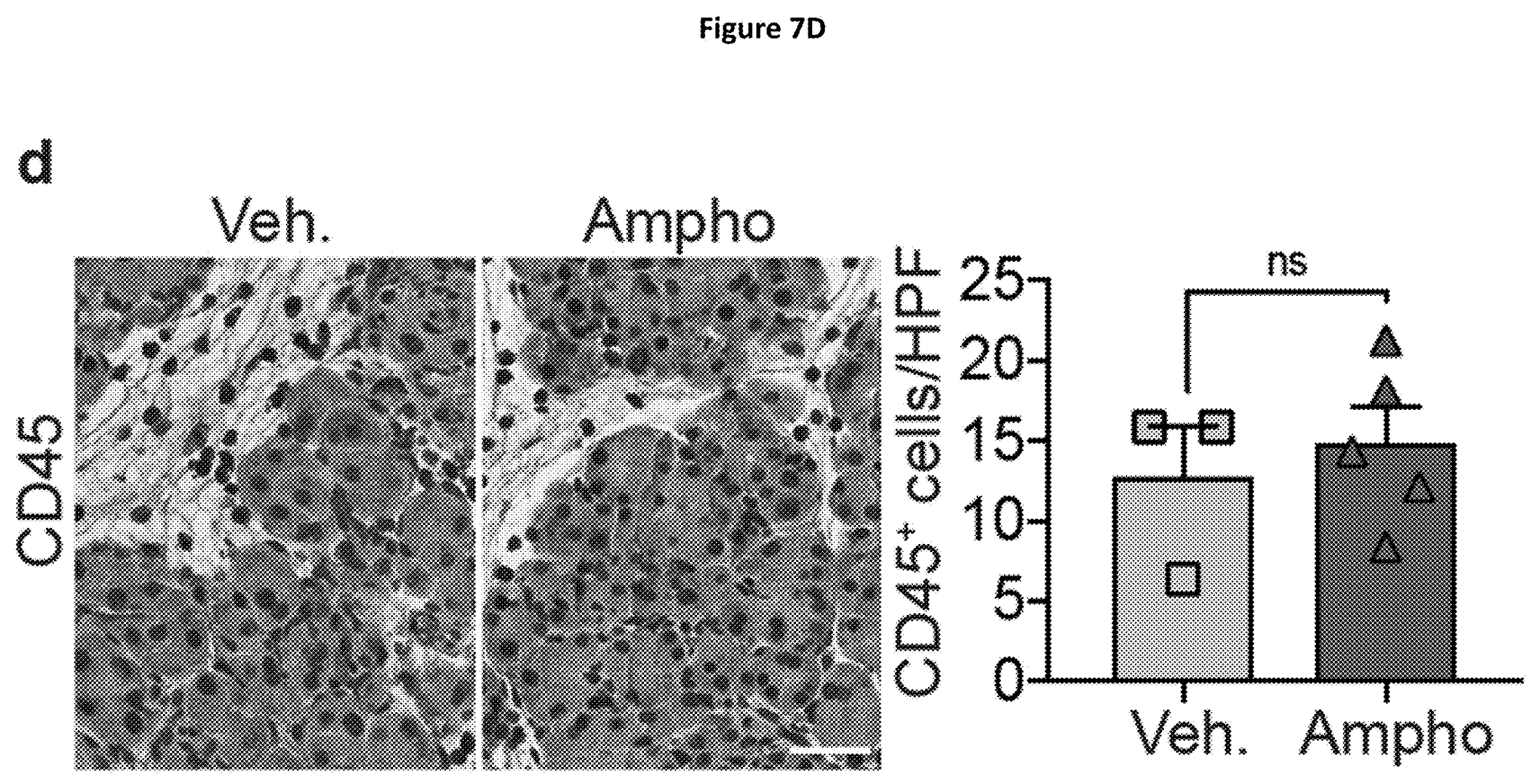
Figure 7E:
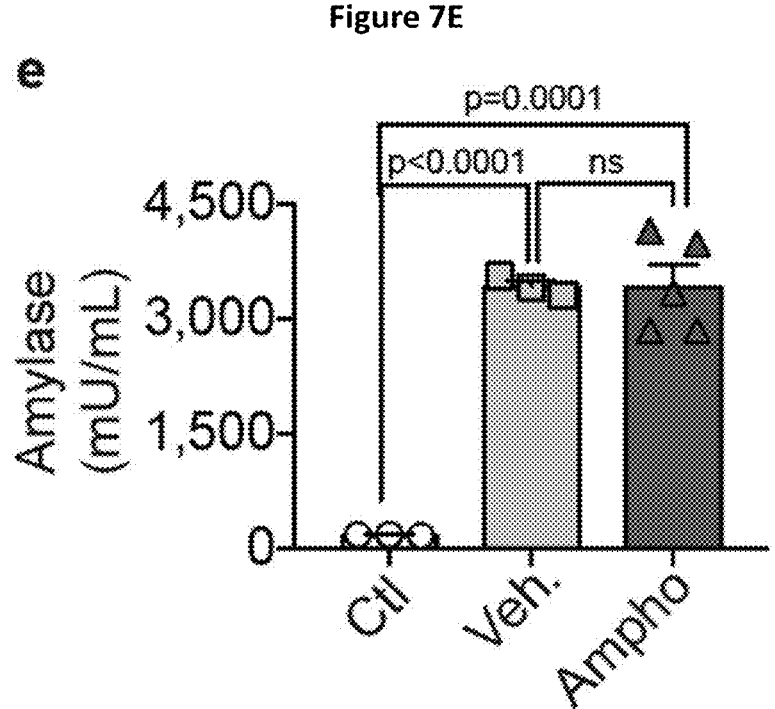

To determine the influence of fungal dysbiosis on the progression of PDA, the mycobiome was ablated using oral administration of amphotericin B in the KC mouse model. Ablation of the mycobiome protected the mice against oncogenic progression (FIG. 3A). Similarly, amphotericin B was protective against progression in an aggressive orthotopic model of PDA that uses tumor cells derived from Pdx1$^{cre}$;Kras$^{G12D}$; Tp53$^{R172H}$ (Tp53 is also known as Trp53) mice (or KPC mice)[3] (FIG. 3B). Ablation of the mycobiome potentiated the effect of chemotherapy based on gemcitabine (FIG. 3C). Of note, treatment with fluconazole was also protective against progression (FIG. 7A). However, treatment with antifungal agents did not offer protection against tumor growth in germ-free mice (FIG. 7B). Further, consistent with absence of increased fungal infiltration in pancreatitis, treatment with antifungal agents did not ameliorate benign pancreatic inflammation (FIGS. 7C-7E).

Figure 3D:
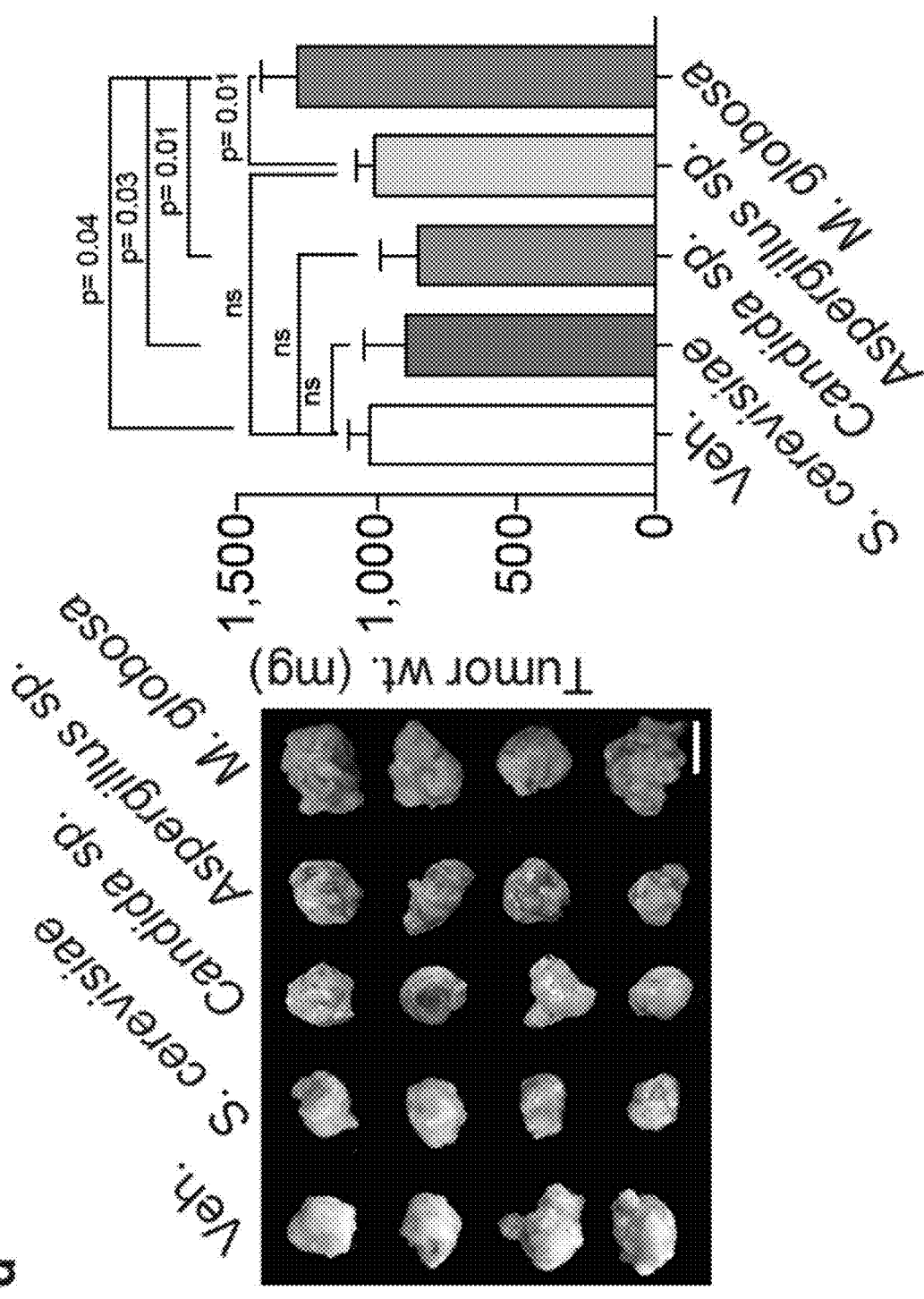
Figure 7F:
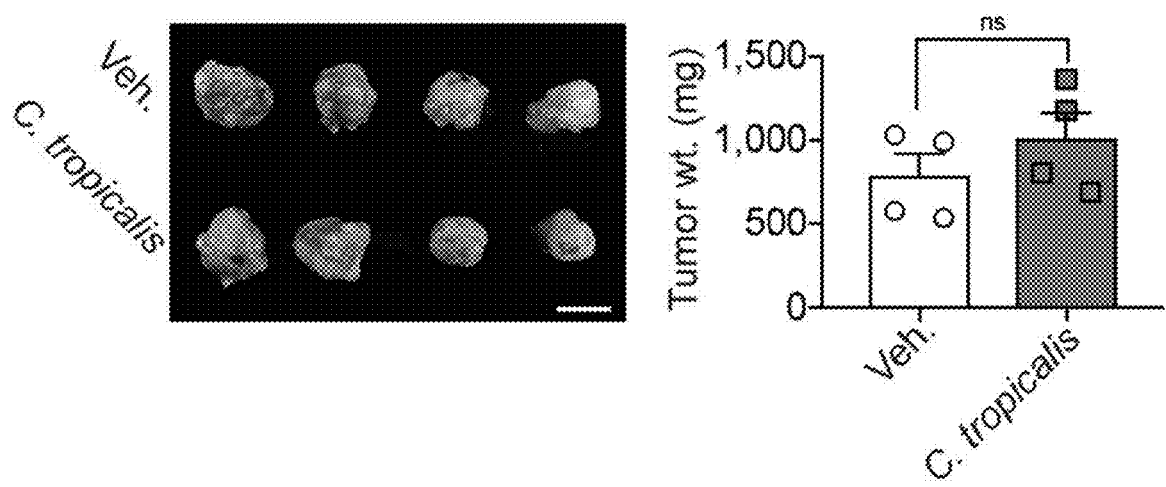

To confirm that fungal dysbiosis accelerates the progression of PDA, mice treated with amphotericin B were repopulated with *Malassezia globosa*, which is present at an increased abundance in PDA and in mouse models of this cancer (FIGS. 1L, 2B). Of note, the *M. globosa* ATCC strain used in the repopulation experiments had 100% sequence identity to the *Malassezia* taxon that was the most abundant in PDA (FIGS. 9A-9D). Control mice were repopulated with *Candida* sp., *S. cerevisiae* or *Aspergillus* sp. or treated with vehicle. Of these, only *M. globosa* accelerated the growth of PDA tumors; the other taxa, and vehicle treatment, had no effect (FIG. 3D). Repopulation with *Candida tropicalis* also did not accelerate the growth of PDA tumors (FIG. 7F).

Figure 4A:
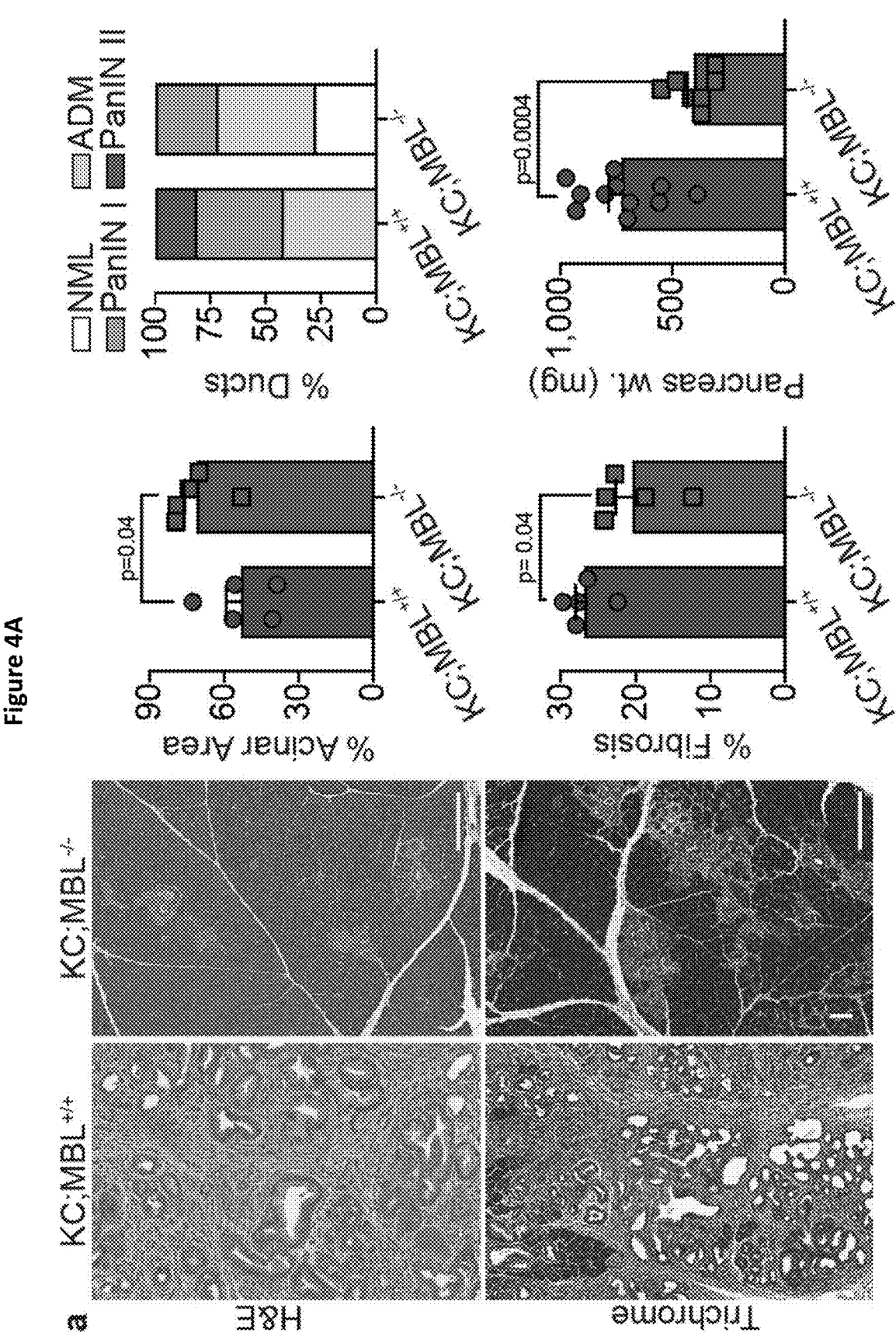
Figure 4B:
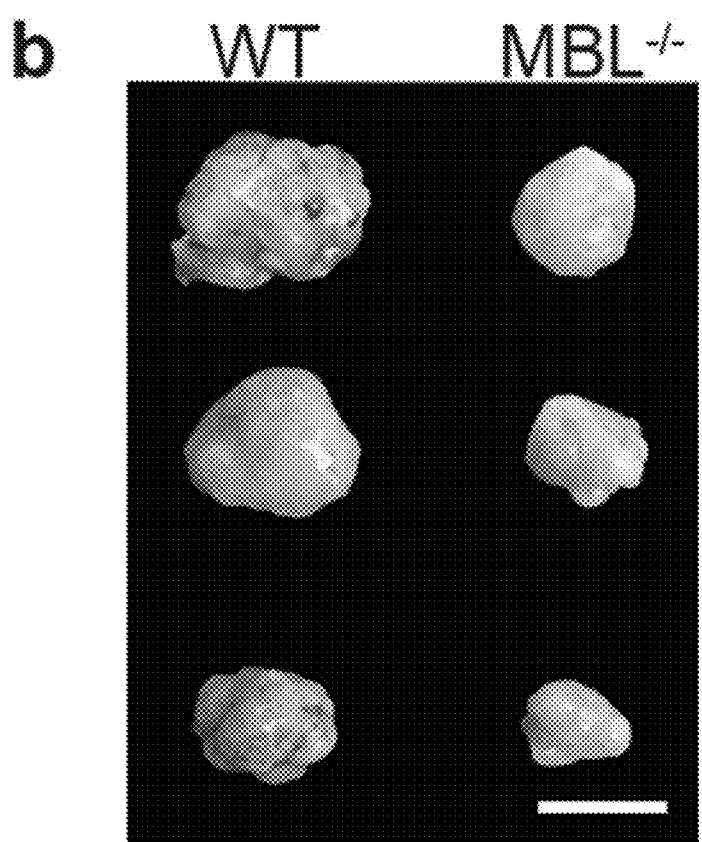
Figure 4B:
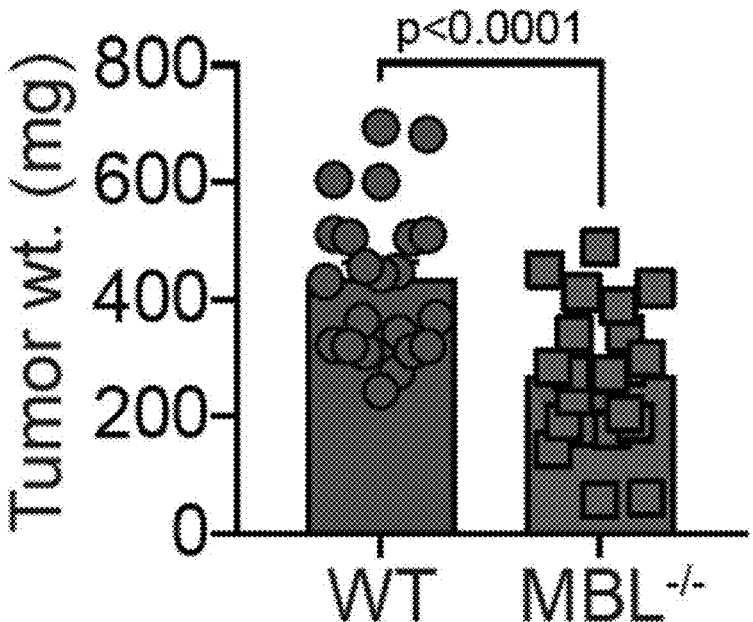
Figure 4C:
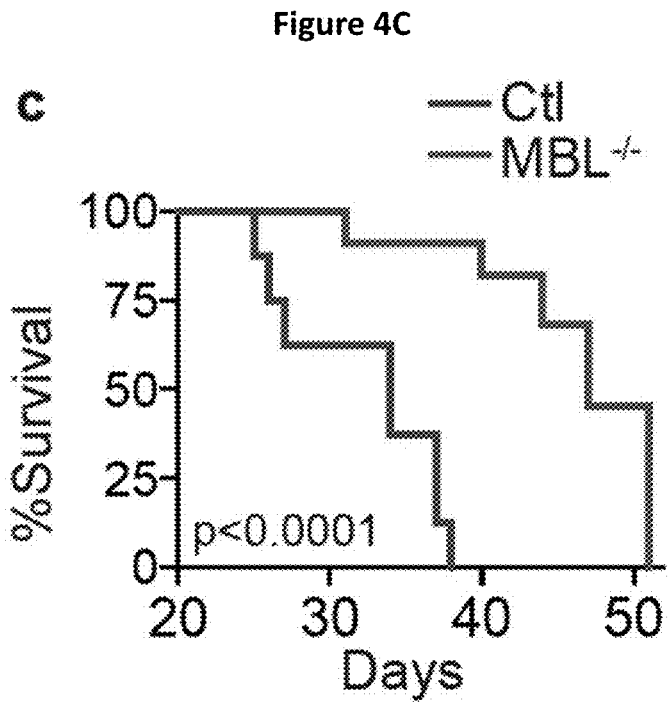
Figure 8A:
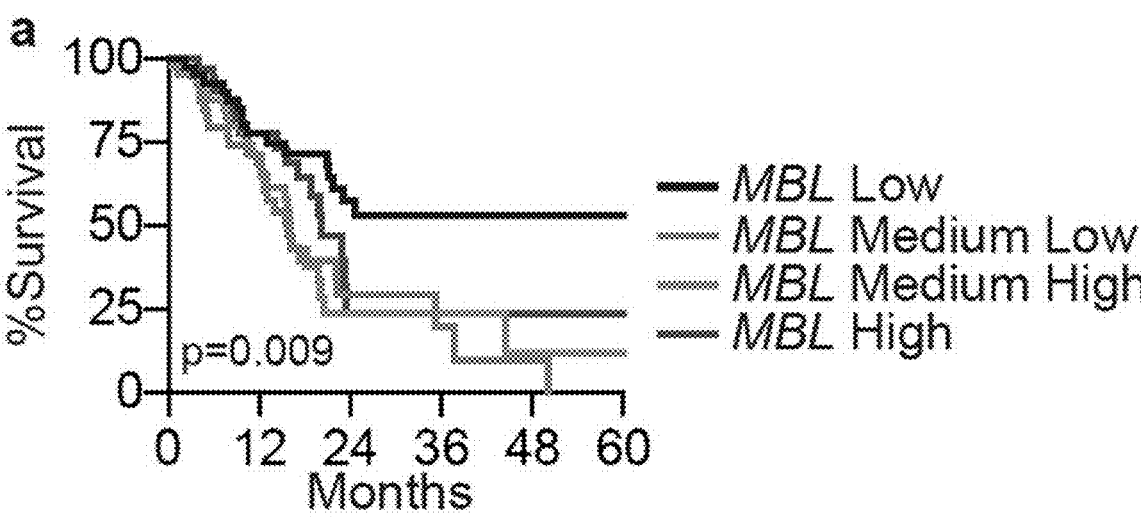
Figure 8A:
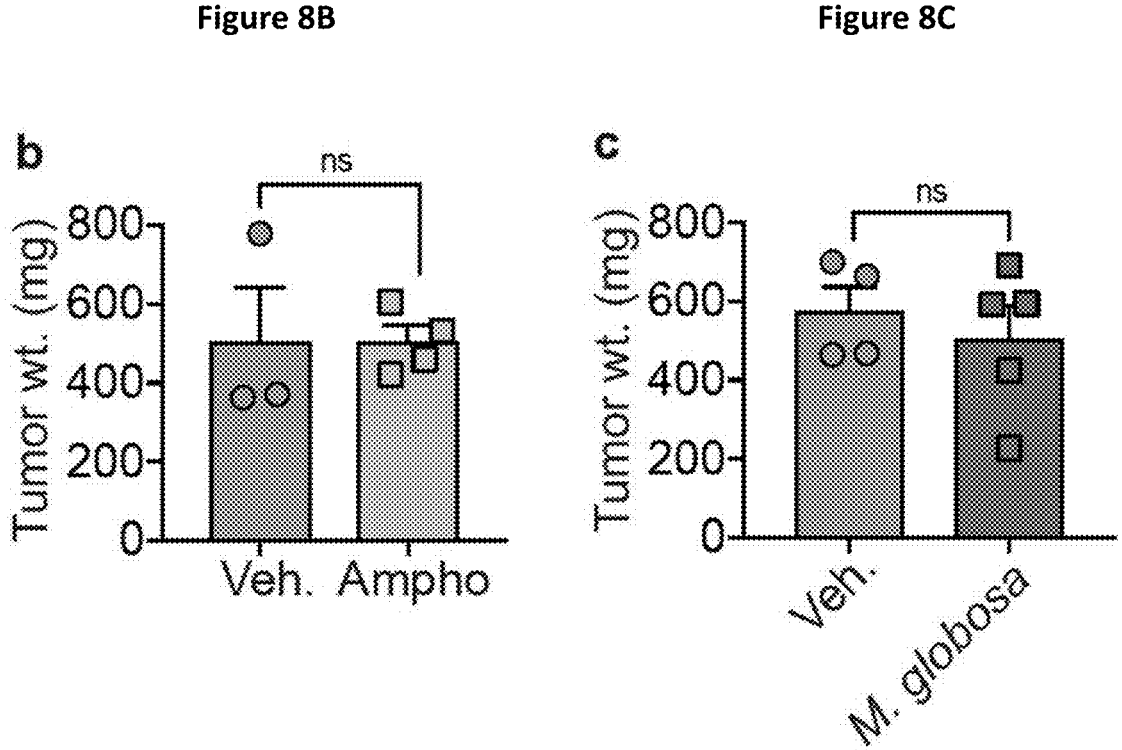

MBL is a mannose-binding lectin that recognizes fungal pathogens and activates the lectin pathway of the complement cascade[4]. Expression of MBL was associated with reduced survival in patients with PDA, on the basis of transcriptomic data from The Cancer Genome Atlas (TCGA) (FIG. 8A). It was postulated that fungi may promote tumorigenesis via activation of MBL. Accordingly, MBL-null KC mice exhibited delayed oncogenic progression (FIG. 4A). Deletion of Mbl was also protective against the growth of orthotopic tumors from KPC mice, and resulted in extended survival of the mice (FIGS. 4B, 4C). Moreover, treatment with amphotericin B did not provide protection against tumor growth in MBL-null mice (FIG. 8B). Similarly, *Malassezia*—which binds C-type lectin receptors[5]— did not accelerate tumor progression in MBL-null mice (FIG. 8C).

Figure 4D:
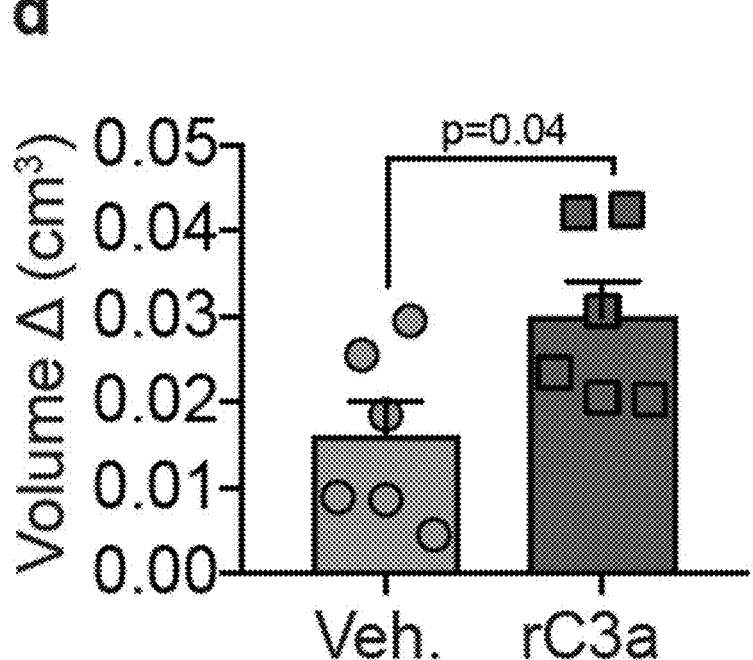
Figure 4E:
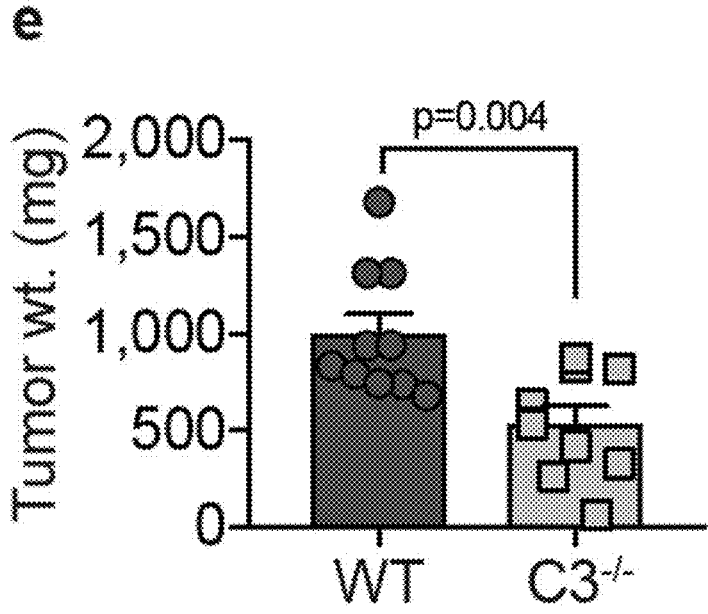
Figure 4F:
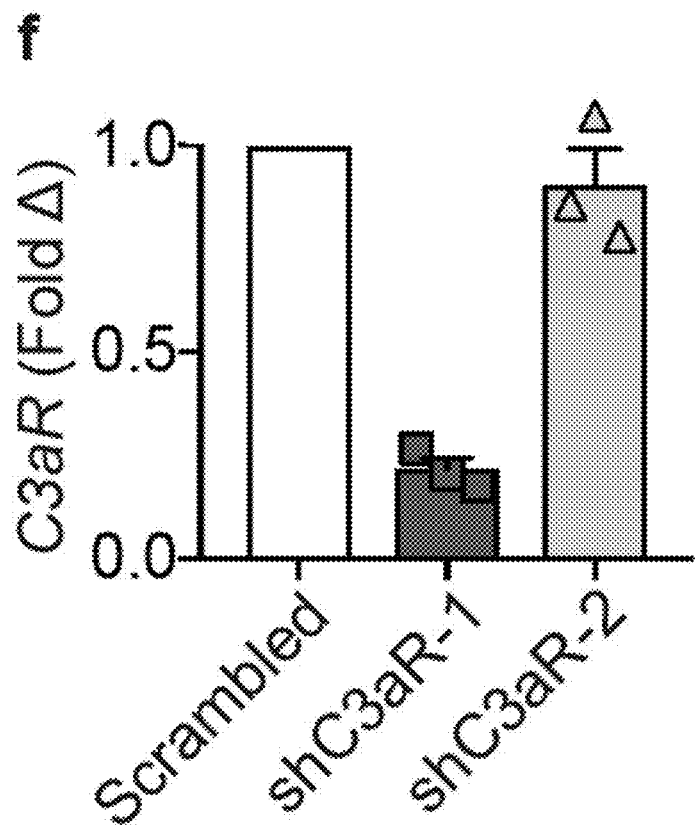
Figure 4G:
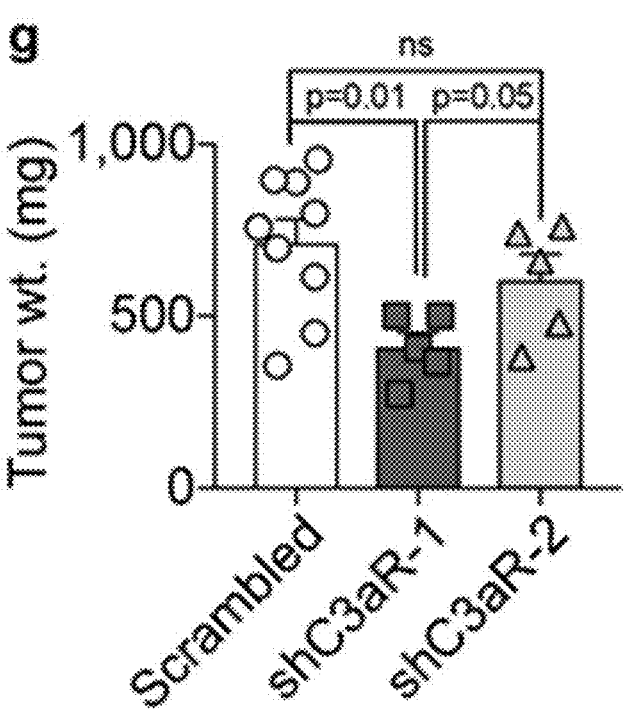
Figure 4H:
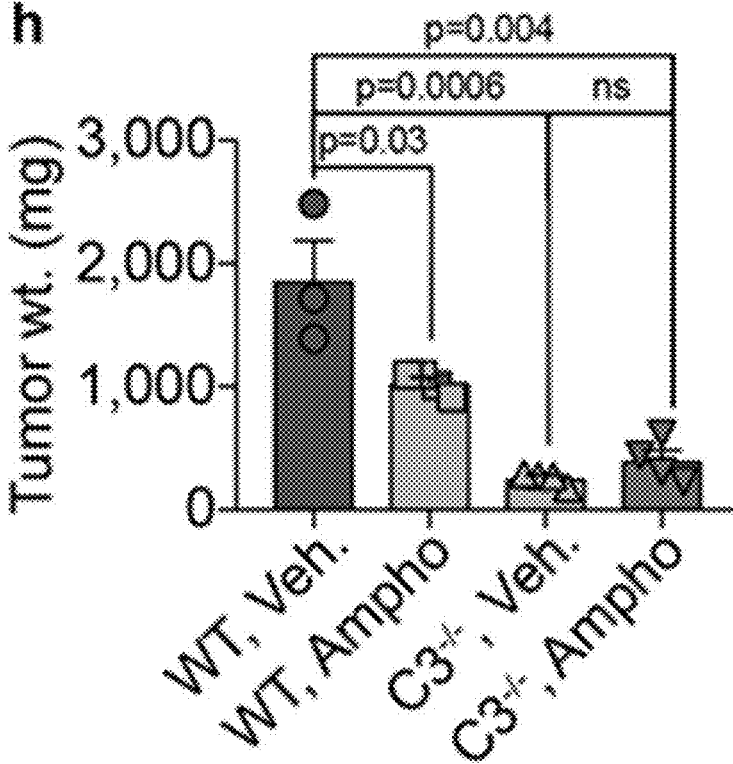
Figure 8D:
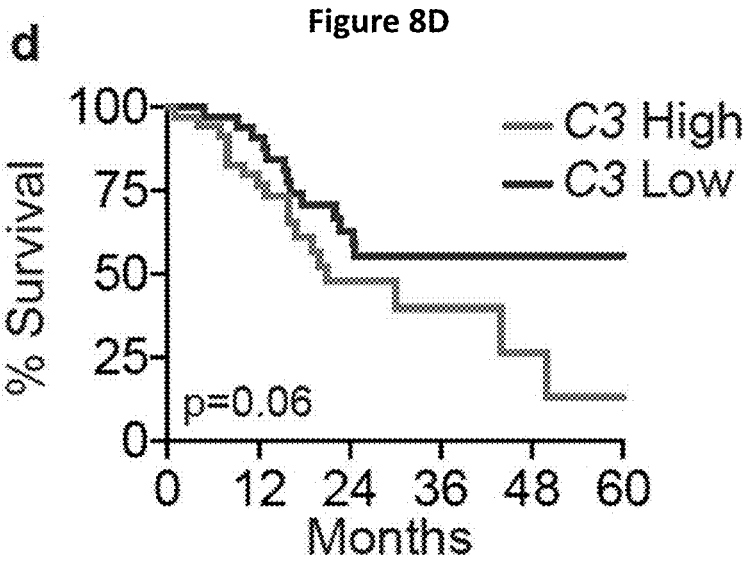
Figure 8E:
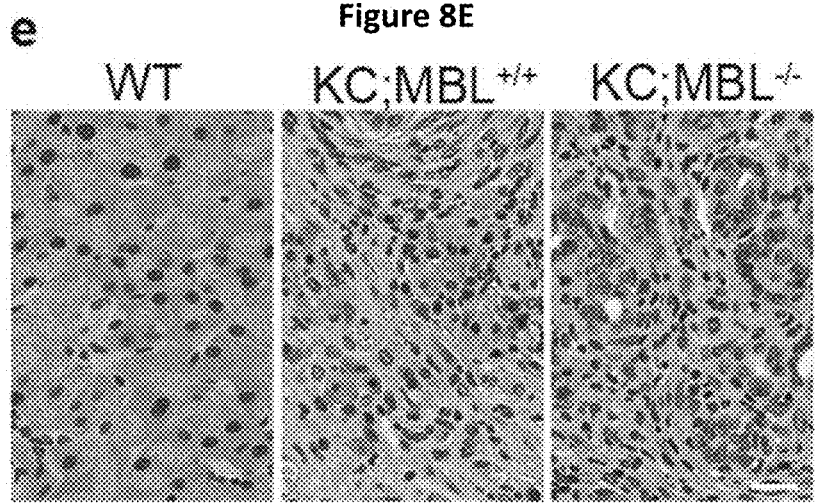
Figure 8F:
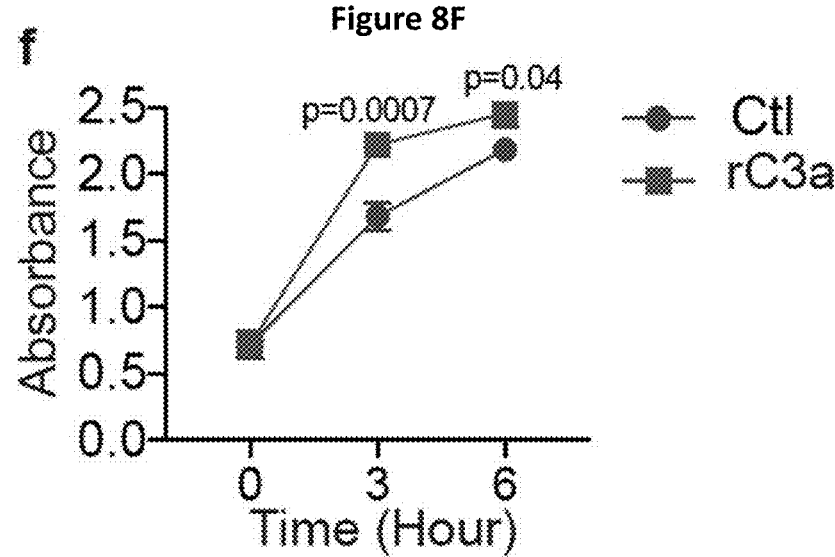

The C3 complement cascade has previously been investigated in PDA and other cancers, and is potently oncogenic through diverse mechanisms that include increasing the proliferation motility and invasiveness of tumor cells, and corrupting adaptive immune responses[6,7]. Because MBL initiates the lectin pathway of the complement cascade that triggers C3 convertase, it was postulated that the fungus-MBL axis promotes the progression of PDA via complement activation. Similar to MBL, the expression of C3 was associated with a trend towards reduced survival in patients with PDA (FIG. 8D). Robust expression of C3a was found in the pancreata of KC mice, and this was nearly absent in wild-type or MBL-null KC mice (FIG. 8E). Consistent with the hypothesis, recombinant C3a accelerated the proliferation of KPC cells in vitro (FIG. 8F) and the growth of KPC tumors in vivo (FIG. 4D), whereas C3-deficient mice were protected against PDA progression (FIG. 4E). Similarly, knockdown of C3aR in PDA cells (FIG. 4F) mitigated tumor growth (FIG. 4G). Moreover, it was found that targeting the mycobiome had no additional effect in C3-deficient animals (FIG. 4H). In aggregate, these data indicate that the pancreatic mycobiome requires the MBL-C3 axis to promote tumor growth.

Figure 4I:
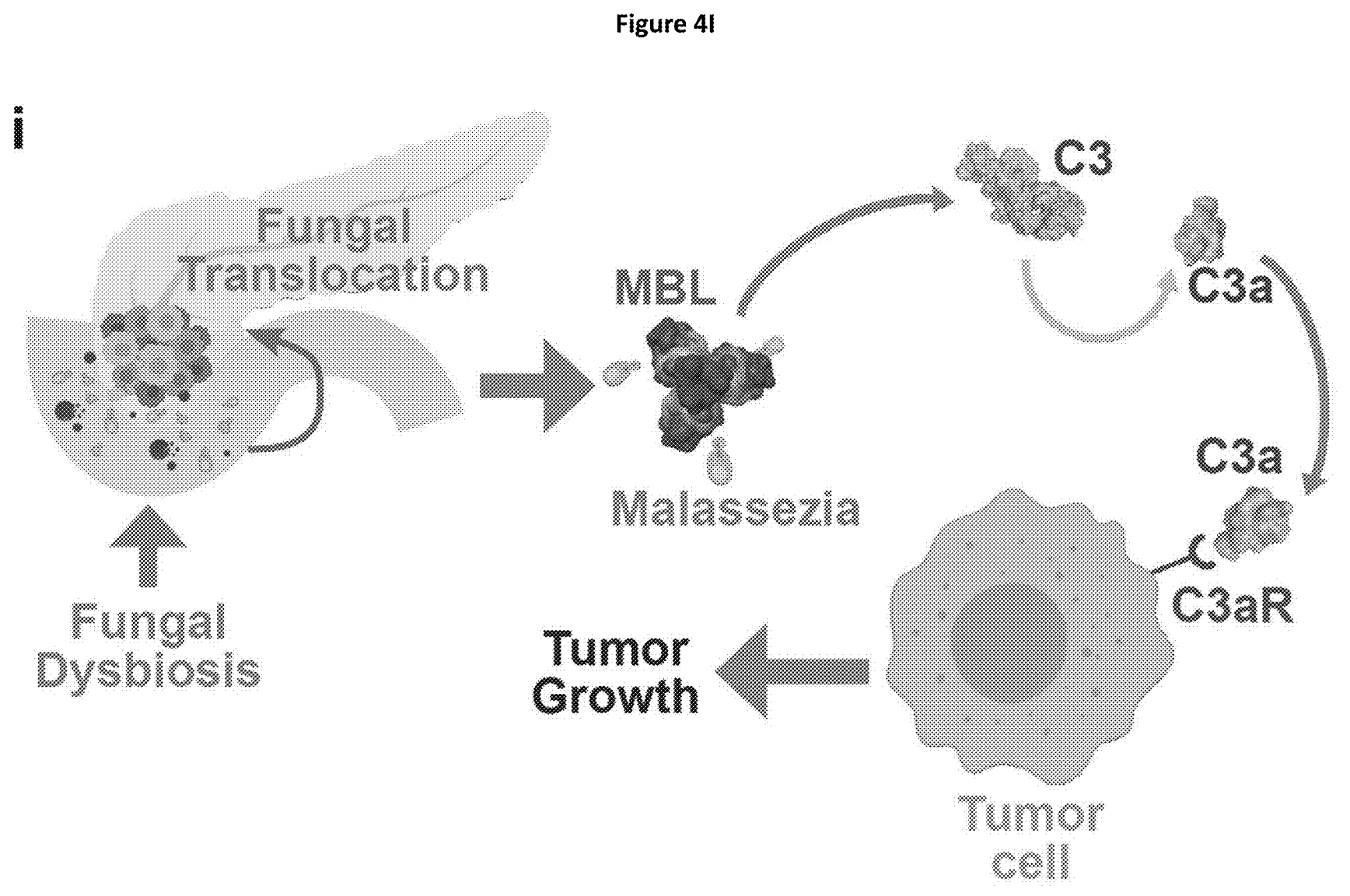

In summary, it was found that fungi migrate from the gut to the pancreas, and PDA tumors contain a marked expansion in the pancreatic mycobiome. The composition of the PDA mycobiome was distinct from that of the gut or normal pancreas, and was enriched forMalassezia species in both mice and humans. Ablation of the mycobiome was protective against progression of PDA, and repopulation with species of *Malassezia*—but not with other commensal fungi—accelerated oncogenesis. Whether the reprogramming of the mycobiome is a cause or consequence of oncogenesis is difficult to answer fully. However, the fungal adoptivetransfer and fungal-ablation experiments suggest that particular species of fungi are sufficient to promote the progression of PDA. It is likely that inflammation induced by oncogeneic Kras leads to fungal dysbiosis, which in turn promotes tumor progression via the activation of the MBL-C3 cascade (FIG. 4I).

Methods

Mice and Tumor Models

KC mice, which develop spontaneous pancreatic neoplasia by targeted expression of mutant Kras in the pancreas[2], were a gift from D. Bar-Sagi. C57BL/6, MBL-null and C3[-/-] mice were originally purchased from Jackson Laboratories and were bred in-house. Littermates were used as controls. Mice were housed in specific-pathogen-free conditions and fed standard mouse chow. In select experiments, C57BL/6 mice generated and housed in a germ-free facility were used. Longitudinal cohort studies were conducted to monitor microbial communities throughout experiments, by serially collecting fecal specimens from littermate wild-type and KC mice. For orthotopic-tumor experiments, 8-10-week-old mice were used. Both male and female mice were used, but mice were sex- and age-matched within each experiment. Mice were administered intrapancreatic injections of FC1242 tumor cells, derived from the pancreata of KPC mice ($10^5$ cells in Matrigel; BD Biosciences), and killed three weeks after injection. The development of the FC1242 cell line has previously been reported[9]. Cells tested negative for mycoplasma within the past two months. In select experiments, mice were treated with intraperitoneal injection of gemcitabine (1.2 mg twice weekly; MedChemExpress). In other experiments, mice received a single intratumoral injection of recombinant mouse C3a (40 µg/kg; R&D) on day 14 after injections of orthotopic tumors. Mice with pancreatic tumors were monitored regularly for distention of the abdomen, reduced feeding, weight loss, dehydration, hunched posture or poor grooming habits. On detection of signs or symptoms of distress, or when tumor size was estimated by palpation to exceed 15% of the normal body weight, mice were euthanized. Pancreatitis was induced using a regimen of 7 hourly intraperitoneal injections of cerulein (50 µg/kg; Sigma-Aldrich) for 3 consecutive days, before mice were killed 12 h later. Levels of serum amylase activity in mouse serum were measured using the colorimetric mouse amylase assay kit (ab102523, Abcam), according to the manufacturer protocols. Proliferation of KPC tumor cells in vitro was assessed using the 2,3-bis(2-methoxy-4-nitro-5-sulfophenyl)-5-[(phenylamino) carbonyl]-2H-tetrazolium hydroxide (XTT) assay (Sigma-Aldrich). Recombinant mC3a (5 nM; R&D) was added to selected wells.

Antifungal Treatment and Fungal-Transfer Experiments

To ablate the mycobiome in mice, amphotericin B (1 mg/ml; MP Biomedicals) was administered to mice by oral gavage daily for five consecutive days, in addition to adding amphotericin B (0.5 µg/ml) to drinking water for the duration of the experiment[10]. Controls were gavaged with PBS. Orthotopic PDA-tumor cells were administered, or pancreatitis was initiated, three weeks after the start of treatment with amphotericin B. Alternatively, mice were treated with fluconazole (0.5 mg/ml; MP Biomedicals) for three weeks before tumor implantation, using the same regimen". For species-specific repopulation experiments, *M. globosa* (MYA-4612, $1\times10^8$ colony-forming units (CFU) per milliliter), *S. cerevisiae* (7752, $1\times10^8$ CFU/ml), *C. tropicalis* (MYA-3404, $1\times10^8$ CFU/ml; all ATCC), *Candida* sp. (clinical isolate; $1\times10^8$ CFU/ml) or *Aspergillus* sp. (clinical isolate; $1\times10^6$ CFU/ml) were used to orally gavage mice, after fungal ablation with amphotericin B. Orthotopic PDA cells were administered to recipient mice seven days after repopulation. To assess fungal translocation to the pancreas, $1\times10^8$ CFU of GFP-labeled *S. cerevisiae* (ATCC MYA-2011) were introduced via oral gavage, and pancreatic samples were examined at 30 min by flow cytometry. All experiments were approved and in compliance with the New York University School of Medicine Institutional Animal Care and Use Committee.

C3aR Knockdown

Lentiviral transfer plasmids against C3aR SHCLNG-NM_009779 (TRCN0000027362; CCAGAAAGCAATTC-TACTGAT (SEQ ID NO: 1) and TRCN0000027385; CCCGTATTTGTATACCGTGAT (SEQ ID NO: 2)) were transformed into Stbl3 bacteria. Plasmids were purified using MaxiPrep Kit (Qiagen) and DNA concentration was evaluated by Nanodrop (Thermo Fisher Scientific). The transfer plasmids were co-transfected into HEK293FT cells with packaging plasmids PLP1, PLP2 and VSVG. To evaluate lentivirus concentration, titration of the ability of virus to induce puromycin-resistant colonies was performed in the HEK293FT cell line. Next, KPC tumor cells were transduced for 48 h, followed by selection with puromycin (2 µg/ul) for 10 days. The efficacy of C3aR knockdown was confirmed by qPCR.

qPCR

Real-time qPCR was performed in duplicate for each sample, using the BioRad Real-Time PCR System (BioRad). Each reaction mixture contained 10 µl of SYBR Green Master Mix (Applied Biosystems), 0.5 µl of forward and reverse primers (Invitrogen) and 3 µl of cDNA (corresponding to 50 ng of RNA). The qPCR conditions were: 50° C. for 2 min, 95° C. for 10 min, followed by 40 cycles at 95° C. for 15 s and 60° C. for 1 min. The amplification of specific transcripts was confirmed by melting-curve profiles, generated at the end of the PCR program. The expression levels of target genes were normalized to the expression of GAPDH or Gapdh (internal control) and calculated on the basis of the comparative cycle threshold method ($2^{-\Delta\Delta C_t}$). The C3aR primer sequences used in the study were: forward, TAACCAGATGAGCACCACCA (SEQ ID NO: 3) and reverse, TGTGAATGTTGTGTGCATTG (SEQ ID NO: 4).

Histology, Immunohistochemistry and Microscopy

For histological analysis, pancreatic specimens were fixed with 10% buffered formalin, dehydrated in ethanol, embedded with paraffin and stained with H&E or Gomori Trichrome. The percentage of preserved acinar area and fibrosis were calculated, as previously described[1]. The fraction and number of ducts that contained any grade of PanIN lesions were measured by examining 10 H&E-stained high-power fields (40× magnification) per slide. PanINs were graded according to established criteria[12]. In PanIN I ducts, the normal cuboidal pancreatic epithelial cells transition to columnar architecture, and can gain polyploid morphology. PanIN II lesions are associated with a loss of polarity. PanIN III lesions (or in-situ carcinoma) show cribriform morphology, the budding off of cells and luminal necrosis with marked cytological abnormalities, without invasion beyond the basement membrane. The characteristics of control KC mice have previously been detailed[13]. Pancreatic oedema was calculated by measuring intralobular white space on H&E sections. Immunohistochemistry was performed using antibodies directed against CD45 (30-F11, BD Biosciences), C3a (JF10-30, Novus), and DAPI (no. H-1200; Vector Laboratories). For paraffin-embedded slides, samples were dewaxed in ethanol, followed by antigen retrieval with 0.01 M sodium citrate with 0.05% Tween.

FISH

The D223 28S rRNA gene probe labeled with the 5' Cy3 fluorophore (extinction wavelength, 555 nm and emission wavelength, 570 nm; Molecular Probes) was used to detect the fungal colonization within human and mouse pancreatic tissues by FISH. Fluorescence microscopic analysis was conducted with Nikon Eclipse 90i confocal microscope (Nikon) using a Cy3-labeled-probe at 350 pmol/ml, as previously described[1].

Human Sample Collection and Data from TCGA

Human fecal samples and specimens of pancreatic tissue were collected under sterile conditions from healthy volunteers and patients undergoing surgery for PDA or for pancreatic endocrine tumors (benign disease) at NYU Langone Medical Center. Donors were de-identified. Samples were stored at −80° C. until analysis. Patients who had received antibiotic or antifungal treatment within the past three months were excluded. Human specimens were collected in compliance with the policies and approval of NYU School of Medicine's Institutional Review Board, and conducted in accordance with the Declaration of Helsinki, the Belmont Report and US Common Rule. Data on gene expression in human tissues was derived from TCGA (portal.gdc.cancer U.S. government website). Survival was measured according to the Kaplan-Meier method, and analyzed using the log-rank test.

Extraction and Sequencing of Fungal DNA

Samples of pancreatic tissue were suspended in 500 μl sterile PBS, and pretreated by vortexing and sonication, followed by overnight treatment with proteinase K (2.5 μg/ml; Thermo Fisher) at 55° C. Total microbial genomic DNA was purified from tissue and fecal samples using the MoBio Power kit, as per the manufacturer's instructions (MoBio Laboratories). DNA was quantified for concentration and purity using the NanoDrop 2000 spectrophotometer (Thermo Fisher) and stored at −20° C. For the preparation and sequencing of a high-throughput ITS library, the ITS1 region of the 18S rRNA gene was amplified from the genomic DNA of mice or of human fecal samples and samples of pancreatic tissue, according to the modified Illumina metagenomics protocol (part no. 15044223 rev. B). The purified DNA was quantified fluorometrically by Quant-iT PicoGreen assay (Molecular Probes) in a SpectraMax M5 microplate reader (Molecular Devices), and the concentration was adjusted to 10 ng/μl for all sequencing assays. PCR was initially performed using the primer set ITS1F (5'-CTTGGTCATTTAGAGGAAGTAA-3' (SEQ ID NO: 5)) and ITS2 (5'-GCTGCGTTCTTCATCGATGC-3' (SEQ ID NO: 6))[14]; each with overhang adaptor sequences (IDT) using 2× Kapa HiFi Hotstart ReadyMix DNA polymerase (KapaBiosystems). Samples were amplified in duplicates and purified using AMPure XP beads. Amplification was performed at 95° C. (5 min), with 25 cycles of 95° C. (1 min), 53° C. (45 s), 72° C. (1 min) and a final extension of 72° C. (10 min). Dual indices from Illumina Nextera XT index kits (Illumina) were added to target amplicons in a second PCR using the 2× Kapa HiFi Hotstart ReadyMix DNA polymerase. PCR conditions were 95° C. (5 min), with 10 cycles of 95° C. (1 min), 53° C. (45 s), 72° C. (1 min) and a final extension of 72° C. (10 min). After each PCR cycle, purified libraries of AMPure XP beads were checked for purity by Nanodrop, quantified by PicoGreen assay and sizes were confirmed on agarose gels. Negative controls were included in all sequencing runs. Equimolar amounts of the generated libraries were combined and quantified fluorometrically. The pooled amplicon library was denatured, diluted and sequenced on an Illumina MiSeq platform using MiSeq Reagent Kit v.3 (600 cycles) following the 2× 300-bp paired-end sequencing protocol.

Bioinformatics and Statistical Analyses

The Illumina-generated fungal ITS sequence data were processed using QIIME (v.1.9.1), and the reads were demultiplexed, quality-filtered and clustered into OTUs using default parameters[15]. To maintain consistency, read 1 was used for the analyses, as previously described[14]. Before demultiplexing, the 5' primers of a total 16,647,630 R1 reads were trimmed using cutadapt (v.1.12), and sequences that were shorter than 100 bases or sequences including asparagine were discarded. The reads were filtered by quality at 20, using multiple_split_libraries_fastq.py (q=19; defaults were used for the other parameters). The 1,989,618 quality reads (mean 8,575; n=166) were then processed with QIIME. Chimeric sequences were removed using VSEARCH (v.2.4.3) with UNITE UCHIME reference dataset (v.7.2). OTUs were picked using the open-reference OUT picking method, with default parameters, against the UNITE reference database (v.7.2) to assign taxonomy using pick_open_reference_otus.py[16]. There were 126,862 OTUs, corresponding to 1,856,993 reads (about 93.57% of the total reads), that did not align to fungi; these OTUs were excluded from the downstream analyses. OTUs that were unidentified in UNITE database were blasted to NCBI, and the taxonomy information of the best hit (similarity or coverage>97%) for each OTU was re-assigned. A total of 127,646 sequence reads were clustered into 1,899 OTUs (corresponding to 86,640 reads) for longitudinal fecal samples from mice; 390 OTUs (corresponding to 25,021 reads) for tissue samples from mice; 2,980 OTUs (corresponding to 15,349 reads) for fecal samples from humans; and 311 OTUs (corresponding to 636 reads) for tissue samples from humans. Sequence data were analyzed at various levels of phylogenetic affiliations. Low-abundance OTUs in <2 samples, and samples identified as outliers, were removed. Distinctions in the composition of the mycobiomes between cohorts and within samples over time were tested for significance using a Mann-Whitney U test. Alpha-diversity and beta-diversity were computed and plotted in Phyloseq. PCoA was performed on Bray-Curtis dissimilarity indices, and a one-way PERMANOVA was used to test for significant differences between cohorts (Adonis, R package Vegan v.2.4.5). P values<0.05 were considered to be significant.

Quality Control

For quality control, best practices for microbiome- and mycobiome-based studies were used, as previously described[1]. All the samples were collected using sterile techniques. All PCR reagents were regularly checked for environmental contaminants using ITS universal primers. All qPCR reactions had appropriate controls (without template) to exclude DNA contaminants. To control for the quality of the sequencing, both predetermined mock communities (such as C. tropicalis) and 'negative' (reagent-only) controls were used, to check background contamination and the rate of sequencing errors. Both of these controls were included in each of the sequencing runs. The quality of the sequencing was further confirmed by including community controls composed of predetermined ratios of DNA from a mixture of three fungal species.

REFERENCES

1. Pushalkar, S. et al. The pancreatic cancer microbiome promotes oncogenesis by induction of innate and adaptive immune suppression. *Cancer Discov.* 8, 403-416 (2018).

2. Hingorani, S. R. et al. Preinvasive and invasive ductal pancreatic cancer and its early detection in the mouse. *Cancer Cell* 4, 437-450 (2003).
3. Hingorani, S. R. et al. Trp53$^{R172H}$ and Kras$^{G12D}$ cooperate to promote chromosomal instability and widely metastatic pancreatic ductal adenocarcinoma in mice. *Cancer Cell* 7, 469-483 (2005).
4. van Asbeck, E. C., Hoepelman, A. I., Scharringa, J., Herpers, B. L. & Verhoef, J. Mannose binding lectin plays a crucial role in innate immunity against yeast by enhanced complement activation and enhanced uptake of polymorphonuclear cells. *BMC Microbiol.* 8, 229 (2008).
5. Ishikawa, T. et al. Identification of distinct ligands for the C-type lectin receptors mincle and dectin-2 in the pathogenic fungus *Malassezia. Cell Host Microbe* 13, 477-488 (2013).
6. Afshar-Kharghan, V. The role of the complement system in cancer. *J. Clin. Invest.* 127, 780-789 (2017).
7. Cho, M. S. et al. Autocrine effects of tumor-derived complement. *Cell Reports* 6, 1085-1095 (2014).
8. Sam, Q. H., Chang, M. W. & Chai, L. Y. The fungal mycobiome and its interaction with gut bacteria in the host. *Int. J. Mol. Sci.* 18, 330 (2017).
9. Zambirinis, C. P. et al. TLR9 ligation in pancreatic stellate cells promotes tumorigenesis. *J. Exp. Med.* 212, 2077-2094 (2015).
10. Reikvam, D. H. et al. Depletion of murine intestinal microbiota: effects on gut mucosa and epithelial gene expression. *PLoS ONE* 6, e17996 (2011).
11. Skalski, J. H. et al. Expansion of commensal fungus *Wallemia mellicola* in the gastrointestinal mycobiota enhances the severity of allergic airway disease in mice. *PLoS Pathog.* 14, e1007260 (2018).
12. Hruban, R. H. et al. Pancreatic intraepithelial neoplasia: a new nomenclature and classification system for pancreatic duct lesions. *Am. J. Surg. Pathol.* 25, 579-586 (2001).
13. Seifert, L. et al. The necrosome promotes pancreatic oncogenesis via CXCL1 and Mincle-induced immune suppression. *Nature* 532, 245-249 (2016).

14. Walters, W. et al. Improved bacterial 16S rRNA gene (V4 and V4-5) and fungal internal transcribed spacer marker gene primers for microbial community surveys. *mSystems* 1, e00009-15 (2015).
15. Navas-Molina, J. A. et al. Advancing our understanding of the human microbiome using QIIME. *Methods Enzymol.* 531, 371-444 (2013).
16. Caporaso, J. G. et al. QIIME allows analysis of high-throughput community sequencing data. *Nat. Methods* 7, 335-336 (2010).
17. Kamada, N., Seo, S.-U., Chen, G. Y. & Nunez, G. Role of the gut microbiota in immunity and inflammatory disease. *Nat Rev Immunol* 13, 321-335 (2013).
18. Schwabe, R. F. & Jobin, C. The microbiome and cancer. *Nature reviews. Cancer* 13, 800-812 (2013).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

LIST OF SEQUENCES

SEQ ID NO: 1 TRCN0000027362
CCAGAAAGCAATTCTACTGAT
SEQ ID NO: 2 TRCN0000027385
CCCGTATTTGTATACCGTGAT
SEQ ID NO: 3 C3aR primer forward
TAACCAGATGAGCACCACCA
SEQ ID NO: 4 C3aR primer reverse
TGTGAATGTTGTGTGCATTG
SEQ ID NO: 5 ITS1F
CTTGGTCATTTAGAGGAAGTAA
SEQ ID NO: 6 ITS2
GCTGCGTTCTTCATCGATGC

What is claimed is:

1. A method for treating pancreatic ductal adenocarcinoma in a subject in need thereof, said method comprising administering to the subject an effective amount of an antifungal compound or composition, wherein the antifungal compound or composition inhibits growth of one or more strains of fungi from the species *Malassezia globosa* in the pancreatic and/or gastrointestinal microbiota of the subject, further comprising determining the level of at least one strain of fungi from the species *Malassezia globosa* in the pancreatic and/or gastrointestinal microbiota of the subject, wherein the antifungal compound or composition comprises amphotericin B or fluconazole.

2. The method of claim 1, wherein the subject has a functional mannose-binding lectin (MBL)-C3 convertase complement axis.

3. The method of claim 1, wherein the subject is human.

4. The method of claim 1, further comprising comparing the level of the at least one strain of fungi from the species *Malassezia globosa* in the pancreatic and/or gastrointestinal microbiota of the subject to the level of the same fungi in a control pancreatic and/or gastrointestinal microbiota.

5. The method of claim 1, wherein the subject displays an increase in at least one strain of fungi from the species *Malassezia globosa* in the pancreatic microbiota as compared to a control pancreatic microbiota.

6. The method of claim 1, wherein the subject displays an increase in at least one strain of fungi from the species *Malassezia globosa* in the gastrointestinal microbiota as compared to a control gastrointestinal microbiota.

7. The method of claim 1, wherein the antifungal compound is administered orally or intravenously from about 0.05 mg/ml to about 10 mg/ml per day.

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccagaaagca attctactga t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cccgtatttg tataccgtga t                                              21

<210> SEQ ID NO 3
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
taaccagatg agcaccacca                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtgaatgtt gtgtgcattg                                                    20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttggtcatt tagaggaagt aa                                                 22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctgcgttct tcatcgatgc                                                    20

<210> SEQ ID NO 7
<211> LENGTH: 275
<212> TYPE: DNA
<213> ORGANISM: Malassezia globosa

<400> SEQUENCE: 7
aagtcgtaac aaggtttctg taggtgaacc tgcagaagga tcattagtga agattcaagg        60
gccagccata cagacgtaca ataagtgtgt ctctggcggc tcgtatccac tatacatcca       120
taaacccgtg tgcactgtta aggagtaaga aagaagggga gggagagagt gcatgtgctt       180
tgcatataac tctctctctt tctcttcctt tctctctctg gttaattaca caaactcgta       240
tggatttgta tgaacgtgag atatatcgtt ggacc                                  275

<210> SEQ ID NO 8
<211> LENGTH: 278
<212> TYPE: DNA
<213> ORGANISM: Malassezia globosa

<400> SEQUENCE: 8
aagtcgtaac aaggtttctg taggtgaacc tgcagaagga tcattagtga agattcaagg        60
gccagccata cagacgtaca acaagtgtgt ctctggcggc tcgcatccca ctatacatcc       120
```

-continued

```
ataaacccgt gtgcacagtt gtaggagtga gaaagaaggg agagagtgcg tgtgttttgc      180
ataactctct ctcgctttct ctctccgatt cattacaaac tcgtatggat ttgtatgaac      240
gtgagatata tcgttggacc gtcactggcc aacaaatg                              278

<210> SEQ ID NO 9
<211> LENGTH: 278
<212> TYPE: DNA
<213> ORGANISM: Malassezia globosa

<400> SEQUENCE: 9
aagtcgtaac aaggtttctg taggtgaacc tgcagaagga tcattagtga agattcaagg       60
gccagccata cagacgtaca ataagtgtgt ctctggcggc tcgtatccac tatacatcca      120
taaacccgtg tgcactgtta aggagtaaga aagaagggga gggagagagt gcatgtgctt      180
tgcatataac tctctctctt tctcttcctt tctctctctg gttaattaca caaactcgta      240
tggatttgta tgaacgtgag atatatcgtt ggaccgtc                              278

<210> SEQ ID NO 10
<211> LENGTH: 279
<212> TYPE: DNA
<213> ORGANISM: Malassezia globosa

<400> SEQUENCE: 10
aagtcgtaac aaggtttctg taggtgaacc tgcagaagga tcattagtga agattcaagg       60
gccagccata cagacgtaca ataagtgtgt ctctggcggc tcgcatccac tatacatcca      120
taaacccgtg tgcactgttc taaggagtaa gaaagaagaa gagagagtgc atgtgctttg      180
catataactc tctcactctc tttctctctc cggttaatta caaactcgta tggatttgta      240
tgaacgtgag atatatcgtt ggaccgtcac tggccaaca                             279
```